(12) United States Patent
DeFonzo et al.

(10) Patent No.: US 9,226,738 B2
(45) Date of Patent: Jan. 5, 2016

(54) VASCULAR HOLE CLOSURE DELIVERY DEVICE

(75) Inventors: Stephan A. DeFonzo, Wayne, PA (US); James S. Tarmin, Philadelphia, PA (US); Thanu Anidharan, Downingtown, PA (US)

(73) Assignee: Rex Medical, L.P., Conshohocken, PA (US)

( * ) Notice: Subject to any disclaimer, the term of this patent is extended or adjusted under 35 U.S.C. 154(b) by 911 days.

(21) Appl. No.: 13/437,146

(22) Filed: Apr. 2, 2012

(65) Prior Publication Data
US 2012/0232583 A1 Sep. 13, 2012

Related U.S. Application Data

(63) Continuation-in-part of application No. 13/274,402, filed on Oct. 17, 2011, now Pat. No. 8,491,629, which is a continuation-in-part of application No. 12/854,988, filed on Aug. 12, 2010, now abandoned, which is a continuation-in-part of application No. 12/358,411, filed on Jan. 23, 2009, now Pat. No. 8,070,772.

(60) Provisional application No. 61/509,829, filed on Jul. 20, 2011, provisional application No. 61/409,599, filed on Nov. 3, 2010, provisional application No. 61/241,555, filed on Sep. 11, 2009, provisional application No. 61/066,072, filed on Feb. 15, 2008.

(51) Int. Cl.
*A61B 17/00* (2006.01)
*A61B 17/04* (2006.01)

(52) U.S. Cl.
CPC ......... *A61B 17/0057* (2013.01); *A61B 17/0401* (2013.01); *A61B 2017/00004* (2013.01); *A61B 2017/00623* (2013.01); *A61B 2017/00659* (2013.01); *A61B 2017/0409* (2013.01); *A61B 2017/0456* (2013.01); *A61B 2017/0459* (2013.01)

(58) Field of Classification Search
CPC .................................................. A61B 17/0057
USPC ................. 606/151–154, 157, 213, 215, 216, 606/218–221
See application file for complete search history.

(56) References Cited

U.S. PATENT DOCUMENTS 2,024,871 A 12/1935 Parsons
2,398,220 A 4/1946 Gelpcke
(Continued)

FOREIGN PATENT DOCUMENTS

DE 19604817 8/1997
EP 0637431 2/1995
(Continued)

*Primary Examiner* — Dianne Dornbusch
(74) *Attorney, Agent, or Firm* — Neil D. Gershon

(57) ABSTRACT

A surgical delivery instrument for delivering a vascular hole closure device having a hole covering member. The delivery instrument comprises a housing, a plunger and an advancer movable within the housing, the advancer having a first portion and a distal portion hingedly connected to the first portion and forming a casing for supporting the hole covering member. Distal movement of the advancer pivots the casing from an angled position to a more linear position to change the orientation of the covering member from a transverse position to a more aligned position. The plunger is advanceable to advance the covering member into the vessel.

20 Claims, 40 Drawing Sheets

(56) References Cited

U.S. PATENT DOCUMENTS

| | | |
|---|---|---|
| 2,413,142 A | 12/1946 | Jones et al. |
| 3,467,089 A | 9/1969 | Hasson |
| 3,516,403 A | 6/1970 | Cournut |
| 3,527,223 A | 9/1970 | Shein |
| 3,675,648 A | 7/1972 | Pharriss et al. |
| 3,842,827 A | 10/1974 | Jacobs |
| 3,874,388 A | 4/1975 | King et al. |
| 3,913,573 A | 10/1975 | Gutnick |
| 3,937,217 A | 2/1976 | Kosonen |
| 3,958,576 A | 5/1976 | Komiya |
| 3,976,079 A | 8/1976 | Samuels et al. |
| 4,007,743 A | 2/1977 | Blake |
| 4,031,569 A | 6/1977 | Jacob |
| 4,117,838 A | 10/1978 | Hasson |
| 4,286,497 A | 9/1981 | Shamah |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,532,926 A | 8/1985 | O'Holla |
| 4,610,671 A | 9/1986 | Luther |
| 4,615,514 A | 10/1986 | Hamlin |
| 4,638,803 A | 1/1987 | Rand |
| 4,665,906 A | 5/1987 | Jervis |
| 4,676,245 A | 6/1987 | Fukuda |
| 4,705,040 A | 11/1987 | Mueller et al. |
| 4,744,364 A | 5/1988 | Kensey |
| 4,796,612 A | 1/1989 | Reese |
| 4,836,204 A | 6/1989 | Landymore et al. |
| 4,890,612 A | 1/1990 | Kensey |
| 4,917,089 A | 4/1990 | Sideris |
| 4,924,866 A | 5/1990 | Yoon |
| 4,971,068 A | 11/1990 | Sahi |
| 5,009,663 A | 4/1991 | Broome |
| 5,021,059 A | 6/1991 | Kensey et al. |
| 5,047,047 A | 9/1991 | Yoon |
| 5,061,274 A | 10/1991 | Kensey |
| 5,108,420 A | 4/1992 | Marks |
| 5,108,421 A | 4/1992 | Fowler |
| 5,123,913 A | 6/1992 | Wilk et al. |
| 5,123,914 A | 6/1992 | Cope |
| 5,171,252 A | 12/1992 | Friedland |
| 5,171,259 A | 12/1992 | Inoue |
| 5,192,300 A | 3/1993 | Fowler |
| 5,192,301 A | 3/1993 | Kamiya et al. |
| 5,192,302 A | 3/1993 | Kensey et al. |
| 5,219,359 A | 6/1993 | McQuilkin et al. |
| 5,222,974 A | 6/1993 | Kensey et al. |
| 5,246,441 A | 9/1993 | Ross et al. |
| 5,269,809 A | 12/1993 | Hayhurst et al. |
| 5,279,572 A | 1/1994 | Hokama |
| 5,282,827 A | 2/1994 | Kensey et al. |
| 5,292,332 A | 3/1994 | Lee |
| 5,306,254 A | 4/1994 | Nash et al. |
| 5,312,435 A | 5/1994 | Nash et al. |
| 5,318,040 A | 6/1994 | Kensey et al. |
| 5,334,210 A | 8/1994 | Gianturco |
| 5,350,399 A | 9/1994 | Erlebacher et al. |
| 5,350,400 A | 9/1994 | Esposito et al. |
| 5,370,661 A | 12/1994 | Branch |
| 5,372,146 A | 12/1994 | Branch |
| 5,385,554 A | 1/1995 | Brimhall |
| RE34,866 E * | 2/1995 | Kensey et al. ............... 606/213 |
| 5,391,183 A | 2/1995 | Janzen et al. |
| 5,409,444 A | 4/1995 | Kensey et al. |
| 5,411,520 A | 5/1995 | Nash et al. |
| 5,433,727 A | 7/1995 | Sideris |
| 5,441,517 A | 8/1995 | Kensey et al. |
| 5,443,481 A | 8/1995 | Lee |
| 5,451,235 A | 9/1995 | Lock et al. |
| 5,474,557 A | 12/1995 | Mai |
| 5,478,352 A | 12/1995 | Fowler |
| 5,478,353 A | 12/1995 | Yoon |
| 5,486,195 A | 1/1996 | Myers et al. |
| 5,507,754 A | 4/1996 | Green et al. |
| 5,520,691 A | 5/1996 | Branch |
| 5,531,759 A | 7/1996 | Kensey et al. |
| 5,540,716 A | 7/1996 | Hlavacek |
| 5,545,178 A | 8/1996 | Kensey et al. |
| 5,549,617 A | 8/1996 | Green et al. |
| 5,549,633 A | 8/1996 | Evans et al. |
| 5,591,204 A | 1/1997 | Janzen et al. |
| 5,593,422 A | 1/1997 | Muijs Van de Moer et al. |
| 5,620,461 A | 4/1997 | Muijs Van De Moer et al. |
| 5,630,833 A | 5/1997 | Katsaros et al. |
| 5,634,936 A | 6/1997 | Linden et al. |
| 5,643,317 A | 7/1997 | Pavcnik et al. |
| 5,649,959 A | 7/1997 | Hannam et al. |
| 5,658,313 A | 8/1997 | Thal |
| 5,662,681 A * | 9/1997 | Nash et al. ............... 606/213 |
| 5,674,231 A | 10/1997 | Green et al. |
| 5,676,689 A | 10/1997 | Kensey et al. |
| 5,690,674 A | 11/1997 | Diaz |
| 5,700,277 A | 12/1997 | Nash et al. |
| 5,702,421 A | 12/1997 | Schneidt |
| 5,707,393 A | 1/1998 | Kensey et al. |
| 5,709,707 A | 1/1998 | Lock et al. |
| 5,725,498 A | 3/1998 | Janzen et al. |
| 5,728,132 A | 3/1998 | Van Tassel et al. |
| 5,728,133 A | 3/1998 | Kontos |
| 5,735,875 A | 4/1998 | Bonutti et al. |
| 5,741,223 A | 4/1998 | Janzen |
| 5,741,297 A | 4/1998 | Simon |
| 5,766,206 A | 6/1998 | Wijkamp et al. |
| 5,769,894 A | 6/1998 | Ferragamo |
| 5,782,600 A | 7/1998 | Walsh |
| 5,782,860 A | 7/1998 | Epstein et al. |
| 5,782,861 A | 7/1998 | Cragg et al. |
| 5,810,845 A | 9/1998 | Yoon |
| 5,810,846 A | 9/1998 | Virnich et al. |
| 5,810,884 A | 9/1998 | Kim |
| 5,814,056 A | 9/1998 | Prosst et al. |
| 5,820,628 A | 10/1998 | Middleman et al. |
| 5,861,003 A | 1/1999 | Latson et al. |
| 5,893,856 A | 4/1999 | Jacob et al. |
| 5,910,155 A | 6/1999 | Ratcliff et al. |
| 5,916,235 A | 6/1999 | Guglielmi |
| 5,916,236 A | 6/1999 | Muijs Van de Moer et al. |
| 5,919,207 A | 7/1999 | Taheri |
| 5,928,266 A | 7/1999 | Kontos |
| 5,964,782 A | 10/1999 | Lafontaine et al. |
| 5,976,159 A | 11/1999 | Bolduc et al. |
| 5,976,174 A | 11/1999 | Ruiz |
| 5,984,933 A | 11/1999 | Yoon |
| 5,984,949 A | 11/1999 | Levin |
| 5,989,268 A | 11/1999 | Pugsley, Jr. et al. |
| 6,001,110 A | 12/1999 | Adams |
| 6,007,563 A | 12/1999 | Nash et al. |
| 6,010,517 A | 1/2000 | Baccaro |
| 6,015,417 A | 1/2000 | Reynolds, Jr. |
| 6,024,756 A | 2/2000 | Huebsch et al. |
| 6,033,427 A | 3/2000 | Lee |
| 6,045,551 A | 4/2000 | Bonutti |
| 6,048,357 A | 4/2000 | Kontos |
| 6,048,358 A | 4/2000 | Barak |
| 6,056,768 A | 5/2000 | Cates et al. |
| 6,063,085 A | 5/2000 | Tay et al. |
| 6,063,106 A | 5/2000 | Gibson |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,110,207 A | 8/2000 | Eichhorn et al. |
| 6,113,611 A | 9/2000 | Allen et al. |
| 6,117,159 A | 9/2000 | Huebsch et al. |
| 6,117,161 A | 9/2000 | Li et al. |
| 6,120,524 A | 9/2000 | Taheri |
| 6,126,675 A | 10/2000 | Shchervinsky et al. |
| 6,136,010 A * | 10/2000 | Modesitt et al. ............... 606/144 |
| 6,139,564 A | 10/2000 | Teoh |
| 6,152,948 A | 11/2000 | Addis |
| 6,162,240 A | 12/2000 | Cates et al. |
| 6,171,320 B1 | 1/2001 | Monassevitch |

(56) References Cited

U.S. PATENT DOCUMENTS

| | | |
|---|---|---|
| 6,171,329 B1 | 1/2001 | Shaw et al. |
| 6,174,322 B1 | 1/2001 | Schneidt |
| 6,179,863 B1 | 1/2001 | Kensey et al. |
| 6,197,042 B1 | 3/2001 | Ginn et al. |
| 6,206,893 B1 | 3/2001 | Klein et al. |
| 6,206,907 B1 | 3/2001 | Marino et al. |
| 6,228,096 B1 | 5/2001 | Marchand |
| 6,231,561 B1 | 5/2001 | Frazier et al. |
| 6,231,592 B1 | 5/2001 | Bonutti et al. |
| 6,251,122 B1 | 6/2001 | Tsukernik |
| 6,261,309 B1 | 7/2001 | Urbanski |
| 6,264,673 B1 | 7/2001 | Egnelöv |
| 6,270,515 B1 | 8/2001 | Linden et al. |
| 6,277,140 B2 | 8/2001 | Ginn et al. |
| 6,290,674 B1 * | 9/2001 | Roue et al. ............. 604/107 |
| 6,293,961 B2 | 9/2001 | Schwartz et al. |
| 6,328,727 B1 | 12/2001 | Frazier et al. |
| 6,334,865 B1 | 1/2002 | Redmond et al. |
| 6,336,914 B1 | 1/2002 | Gillespie, III |
| 6,342,064 B1 | 1/2002 | Koike et al. |
| 6,346,117 B1 | 2/2002 | Greenhalgh |
| 6,348,053 B1 | 2/2002 | Cachia |
| 6,350,270 B1 | 2/2002 | Roue |
| 6,350,274 B1 | 2/2002 | Li |
| 6,355,052 B1 | 3/2002 | Neuss et al. |
| 6,368,341 B1 | 4/2002 | Abrahamson |
| 6,368,343 B1 | 4/2002 | Bonutti et al. |
| 6,391,037 B1 | 5/2002 | Greenhalgh |
| 6,391,048 B1 | 5/2002 | Ginn et al. |
| 6,409,739 B1 | 6/2002 | Nobles et al. |
| 6,414,664 B1 | 7/2002 | Conover et al. |
| 6,419,669 B1 | 7/2002 | Frazier et al. |
| 6,425,911 B1 | 7/2002 | Akerfeldt |
| 6,436,088 B2 | 8/2002 | Frazier et al. |
| 6,440,152 B1 * | 8/2002 | Gainor et al. ............. 606/213 |
| 6,447,042 B1 | 9/2002 | Jin |
| 6,447,524 B1 | 9/2002 | Knodel et al. |
| 6,451,030 B2 * | 9/2002 | Li et al. ............. 606/139 |
| 6,468,293 B2 | 10/2002 | Bonutti et al. |
| 6,482,179 B1 | 11/2002 | Chu et al. |
| 6,491,714 B1 | 12/2002 | Bennett |
| 6,500,184 B1 | 12/2002 | Chan et al. |
| 6,503,266 B1 | 1/2003 | Sjögren |
| 6,508,828 B1 | 1/2003 | Akerfeldt |
| 6,537,299 B1 | 3/2003 | Hogendijk et al. |
| 6,547,806 B1 | 4/2003 | Ding |
| 6,569,185 B2 | 5/2003 | Ungs |
| 6,569,187 B1 | 5/2003 | Bonutti et al. |
| 6,585,748 B1 | 7/2003 | Jeffree |
| 6,585,750 B2 | 7/2003 | Bonutti et al. |
| 6,596,012 B2 | 7/2003 | Akerfeldt |
| 6,626,937 B1 | 9/2003 | Cox |
| 6,635,073 B2 | 10/2003 | Bonutti |
| 6,648,903 B1 | 11/2003 | Pierson, III |
| 6,663,653 B2 | 12/2003 | Akerfeldt |
| 6,663,655 B2 | 12/2003 | Ginn et al. |
| 6,676,685 B2 | 1/2004 | Pedros et al. |
| 6,682,489 B2 | 1/2004 | Tenerz |
| 6,699,263 B2 | 3/2004 | Cope |
| 6,712,836 B1 | 3/2004 | Berg et al. |
| 6,712,837 B2 | 3/2004 | Akerfeldt |
| 6,749,621 B2 | 6/2004 | Pantages et al. |
| 6,749,622 B2 | 6/2004 | McGuckin, Jr. et al. |
| 6,764,500 B2 | 7/2004 | Muijs van de Moer et al. |
| 6,766,186 B1 | 7/2004 | Hoyns et al. |
| 6,786,915 B2 | 9/2004 | Akerfeldt et al. |
| 6,790,220 B2 | 9/2004 | Morris |
| 6,846,316 B2 | 1/2005 | Abrams |
| 6,855,153 B2 | 2/2005 | Saadat |
| 6,860,895 B1 | 3/2005 | Akerfeldt |
| 6,863,680 B2 | 3/2005 | Ashby |
| 6,909,130 B2 | 6/2005 | Yoda et al. |
| 6,929,655 B2 | 8/2005 | Egnelöv |
| 6,932,835 B2 | 8/2005 | Bonutti et al. |
| 6,939,363 B2 | 9/2005 | Akerfeldt |
| 6,949,107 B2 | 9/2005 | McGuckin, Jr. et al. |
| 6,960,224 B2 | 11/2005 | Marino et al. |
| 6,972,027 B2 * | 12/2005 | Fallin et al. ............. 606/232 |
| 6,984,219 B2 | 1/2006 | Ashby et al. |
| 6,997,940 B2 | 2/2006 | Bonutti |
| 7,008,440 B2 | 3/2006 | Sing et al. |
| 7,008,442 B2 | 3/2006 | Brightbill |
| 7,025,756 B2 | 4/2006 | Frazier et al. |
| 7,025,776 B1 | 4/2006 | Houser et al. |
| 7,033,380 B2 | 4/2006 | Schwartz et al. |
| 7,033,393 B2 | 4/2006 | Gainor et al. |
| 7,048,748 B1 | 5/2006 | Ustuner |
| 7,048,755 B2 | 5/2006 | Bonutti et al. |
| 7,083,635 B2 | 8/2006 | Ginn |
| 7,087,073 B2 | 8/2006 | Bonutti |
| 7,094,209 B2 | 8/2006 | Egnelöv |
| 7,115,110 B2 | 10/2006 | Frazier et al. |
| 7,135,032 B2 | 11/2006 | Akerfeldt |
| 7,147,652 B2 | 12/2006 | Bonutti et al. |
| 7,150,757 B2 | 12/2006 | Fallin et al. |
| 7,153,323 B1 | 12/2006 | Teoh et al. |
| 7,169,168 B2 | 1/2007 | Muijs Van de Moer et al. |
| 7,175,648 B2 | 2/2007 | Nakao |
| 7,235,091 B2 | 6/2007 | Thornes |
| 7,267,679 B2 | 9/2007 | McGuckin, Jr. et al. |
| 7,285,097 B2 | 10/2007 | Tenerz |
| 7,288,105 B2 | 10/2007 | Oman et al. |
| 7,316,706 B2 | 1/2008 | Bloom et al. |
| 7,329,270 B2 | 2/2008 | Akerfeldt |
| 7,341,595 B2 | 3/2008 | Hinchliffe et al. |
| 7,361,183 B2 | 4/2008 | Ginn |
| 7,468,068 B2 | 12/2008 | Kolster |
| 7,488,340 B2 | 2/2009 | Kauphusman et al. |
| 7,530,990 B2 | 5/2009 | Perriello et al. |
| 7,566,339 B2 | 7/2009 | Fallin et al. |
| 7,582,105 B2 | 9/2009 | Kolster |
| 7,594,923 B2 | 9/2009 | Fallin et al. |
| 7,597,705 B2 | 10/2009 | Forsberg et al. |
| 7,618,438 B2 | 11/2009 | White et al. |
| 7,621,937 B2 | 11/2009 | Pipenhagen et al. |
| 7,625,352 B1 | 12/2009 | Ashby et al. |
| 7,637,921 B2 | 12/2009 | Akerfeldt |
| 7,654,963 B2 | 2/2010 | Egnelöv |
| 7,658,751 B2 * | 2/2010 | Stone et al. ............. 606/232 |
| 7,662,160 B2 | 2/2010 | Bojarski et al. |
| 7,662,161 B2 | 2/2010 | Briganti et al. |
| 7,666,199 B2 | 2/2010 | McIntyre |
| 7,717,929 B2 | 5/2010 | Fallman |
| 7,736,378 B2 * | 6/2010 | Maahs et al. ............. 606/232 |
| 7,758,594 B2 | 7/2010 | Lamson et al. |
| 7,775,988 B2 | 8/2010 | Pijls |
| 7,780,699 B2 | 8/2010 | Zhu |
| 7,824,417 B2 | 11/2010 | Magnusson |
| 7,846,180 B2 | 12/2010 | Cerier |
| 7,931,670 B2 | 4/2011 | Fiehler |
| 7,931,671 B2 | 4/2011 | Tenerz |
| 7,938,846 B2 | 5/2011 | Akerfeldt |
| 7,967,840 B2 | 6/2011 | Chanduszko |
| 8,016,857 B2 | 9/2011 | Sater |
| 8,088,143 B2 | 1/2012 | Akerfeldt |
| 8,105,352 B2 | 1/2012 | Egnelöv |
| 8,118,831 B2 | 2/2012 | Egnelöv |
| 8,118,832 B1 | 2/2012 | Morris |
| 8,267,959 B2 | 9/2012 | Fällman |
| 8,308,762 B2 | 11/2012 | Mahlin et al. |
| 8,348,971 B2 | 1/2013 | Khanna et al. |
| 8,382,793 B2 | 2/2013 | Egnelöv |
| 8,398,675 B2 | 3/2013 | Egnelöv |
| 8,444,673 B2 | 5/2013 | Thielen et al. |
| RE44,297 E | 6/2013 | Akerfeldt |
| 8,469,944 B2 | 6/2013 | Mahlin |
| 8,647,365 B2 | 2/2014 | Tegels |
| 8,652,166 B2 * | 2/2014 | Åkerfeldt ............. 606/213 |
| 2002/0082622 A1 | 6/2002 | Kane |
| 2002/0095179 A1 | 7/2002 | Tenerz et al. |
| 2002/0165561 A1 | 11/2002 | Ainsworth et al. |
| 2002/0165572 A1 | 11/2002 | Saadat |
| 2003/0009180 A1 | 1/2003 | Hinchliffe et al. |
| 2003/0050665 A1 | 3/2003 | Ginn |

(56) References Cited

U.S. PATENT DOCUMENTS

| | | |
|---|---|---|
| 2003/0055451 A1 | 3/2003 | Jones et al. |
| 2003/0088256 A1 | 5/2003 | Conston et al. |
| 2003/0088269 A1 | 5/2003 | Ashby |
| 2003/0105487 A1 | 6/2003 | Benz et al. |
| 2003/0130694 A1 | 7/2003 | Bojarski et al. |
| 2003/0144695 A1* | 7/2003 | McGuckin et al. ............ 606/213 |
| 2003/0187473 A1 | 10/2003 | Berenstein et al. |
| 2003/0191495 A1 | 10/2003 | Ryan et al. |
| 2004/0002764 A1 | 1/2004 | Gainor et al. |
| 2004/0010287 A1 | 1/2004 | Bonutti |
| 2004/0039413 A1 | 2/2004 | Akerfeldt |
| 2004/0093025 A1 | 5/2004 | Egnelov |
| 2004/0133236 A1 | 7/2004 | Chanduszko |
| 2004/0133238 A1* | 7/2004 | Cerier ........................ 606/232 |
| 2004/0143294 A1 | 7/2004 | Corcoran et al. |
| 2004/0153103 A1 | 8/2004 | Schwartz et al. |
| 2004/0158287 A1 | 8/2004 | Cragg et al. |
| 2004/0176800 A1 | 9/2004 | Paraschac et al. |
| 2004/0230223 A1 | 11/2004 | Bonutti et al. |
| 2005/0033326 A1* | 2/2005 | Briganti et al. ............... 606/151 |
| 2005/0059982 A1* | 3/2005 | Zung et al. .................... 606/144 |
| 2005/0065547 A1 | 3/2005 | Marino et al. |
| 2005/0070957 A1 | 3/2005 | Das |
| 2005/0075654 A1 | 4/2005 | Kelleher |
| 2005/0085852 A1* | 4/2005 | Ditter ............................ 606/213 |
| 2005/0085855 A1 | 4/2005 | Forsberg |
| 2005/0090859 A1 | 4/2005 | Ravlkumar |
| 2005/0096696 A1 | 5/2005 | Forsberg |
| 2005/0096697 A1* | 5/2005 | Forsberg et al. ............. 606/213 |
| 2005/0107807 A1 | 5/2005 | Nakao |
| 2005/0125030 A1* | 6/2005 | Forsberg et al. ............. 606/213 |
| 2005/0125031 A1 | 6/2005 | Pipenhagen et al. |
| 2005/0125032 A1 | 6/2005 | Whisenant et al. |
| 2005/0169974 A1 | 8/2005 | Tenerz |
| 2005/0192627 A1 | 9/2005 | Whisenant et al. |
| 2005/0192630 A1 | 9/2005 | Maas et al. |
| 2005/0267524 A1 | 12/2005 | Chanduszko |
| 2005/0283193 A1 | 12/2005 | Tullberg |
| 2006/0069408 A1 | 3/2006 | Kato |
| 2006/0100665 A1 | 5/2006 | Von Oepen et al. |
| 2006/0106418 A1 | 5/2006 | Seibold et al. |
| 2006/0135991 A1 | 6/2006 | Kawaura et al. |
| 2006/0142797 A1 | 6/2006 | Egnelov |
| 2006/0155327 A1 | 7/2006 | Briganti |
| 2006/0167495 A1 | 7/2006 | Bonutti et al. |
| 2006/0173492 A1 | 8/2006 | Akerfeldt |
| 2006/0212073 A1 | 9/2006 | Bonutti et al. |
| 2006/0217760 A1 | 9/2006 | Widomski et al. |
| 2006/0217765 A1 | 9/2006 | Bonutti et al. |
| 2006/0241695 A1 | 10/2006 | Bonutti et al. |
| 2006/0265009 A1 | 11/2006 | Bonutti |
| 2006/0271105 A1 | 11/2006 | Foerster et al. |
| 2006/0276871 A1 | 12/2006 | Lamson et al. |
| 2007/0010851 A1 | 1/2007 | Chanduszko et al. |
| 2007/0010857 A1 | 1/2007 | Sugimoto et al. |
| 2007/0060858 A1 | 3/2007 | Sogard et al. |
| 2007/0073322 A1* | 3/2007 | Mikkaichi et al. ............ 606/153 |
| 2007/0149987 A1 | 6/2007 | Wellman et al. |
| 2007/0149998 A1 | 6/2007 | Wicks et al. |
| 2007/0149999 A1 | 6/2007 | Szabo et al. |
| 2007/0150002 A1 | 6/2007 | Szabo et al. |
| 2007/0156175 A1 | 7/2007 | Weadock et al. |
| 2007/0185532 A1 | 8/2007 | Stone et al. |
| 2007/0239208 A1 | 10/2007 | Crawford |
| 2007/0239209 A1 | 10/2007 | Fallman |
| 2007/0244518 A1 | 10/2007 | Callaghan |
| 2007/0255316 A1 | 11/2007 | McIntyre |
| 2008/0071310 A1 | 3/2008 | Hoffman et al. |
| 2008/0082128 A1 | 4/2008 | Stone |
| 2008/0114395 A1 | 5/2008 | Mathisen |
| 2008/0140092 A1 | 6/2008 | Stone et al. |
| 2009/0030450 A1 | 1/2009 | Preinitz |
| 2009/0036919 A1 | 2/2009 | Preinitz |
| 2009/0036920 A1 | 2/2009 | Preinitz |
| 2009/0043333 A1 | 2/2009 | Preinitz |
| 2009/0177225 A1 | 7/2009 | Nunez et al. |
| 2009/0210004 A1 | 8/2009 | McGuckin, Jr. et al. |
| 2009/0216267 A1 | 8/2009 | Willard et al. |
| 2009/0234377 A1 | 9/2009 | Mahlin |
| 2009/0248064 A1 | 10/2009 | Preinitz |
| 2009/0326460 A1* | 12/2009 | Beardsley ................ 604/164.01 |
| 2010/0312224 A1 | 12/2010 | Atthoff |
| 2011/0270307 A1 | 11/2011 | Szabo |
| 2012/0078294 A1 | 3/2012 | Tarmin et al. |

FOREIGN PATENT DOCUMENTS

| | | |
|---|---|---|
| EP | 0920842 | 6/1999 |
| EP | 1671591 | 6/2006 |
| EP | 1671592 | 6/2006 |
| EP | 2055236 | 5/2009 |
| EP | 2294986 | 3/2011 |
| EP | 2412317 | 2/2012 |
| WO | WO 94/28800 | 12/1994 |
| WO | 9520916 | 8/1995 |
| WO | WO 95/32670 | 12/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | WO 01/40348 | 11/2000 |
| WO | WO 00/78226 | 12/2000 |
| WO | WO-2004/012601 | 2/2004 |
| WO | WO 2004/098418 | 11/2004 |
| WO | 2004112864 | 12/2004 |
| WO | WO 2006/093970 | 9/2006 |

\* cited by examiner

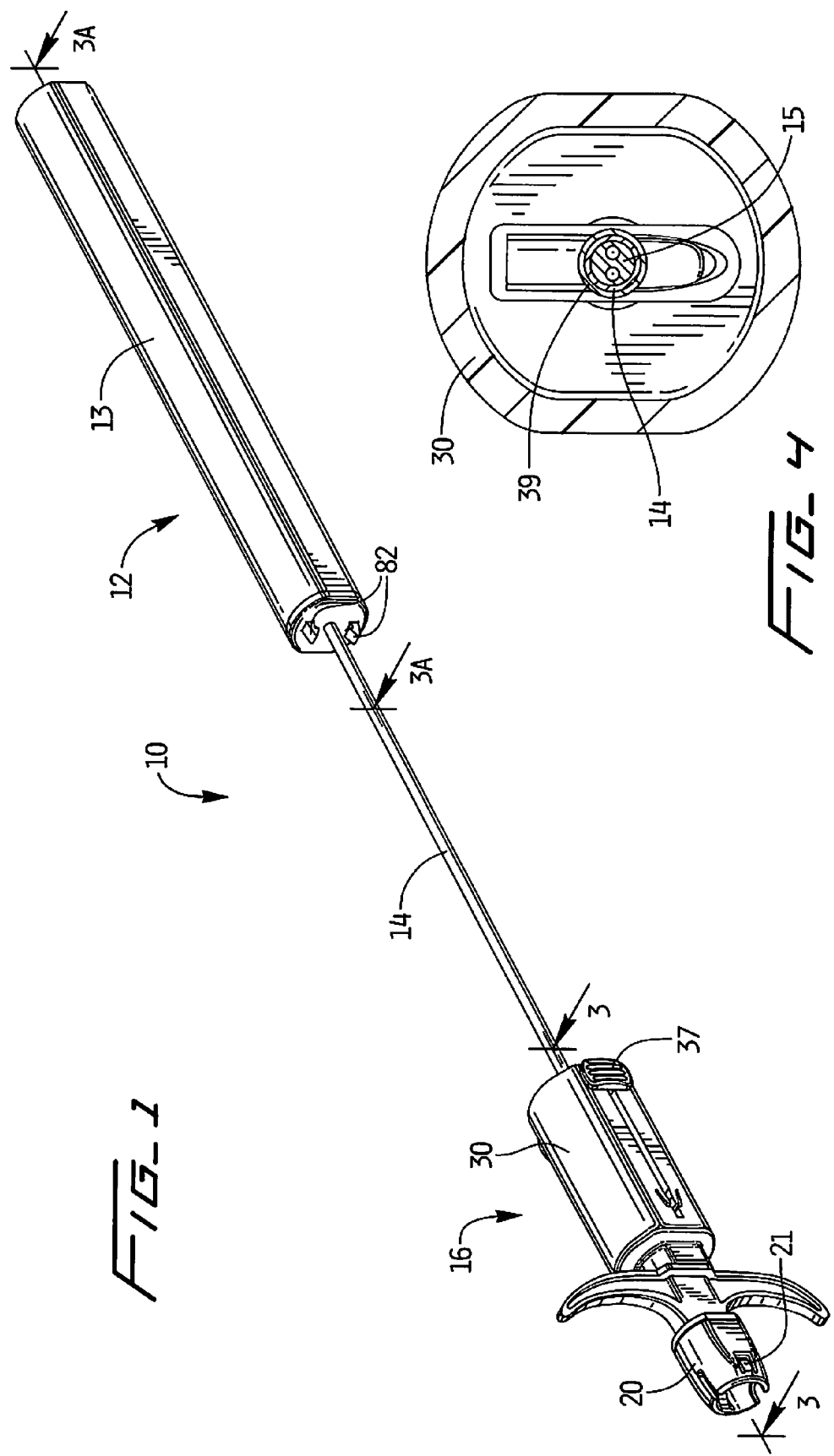

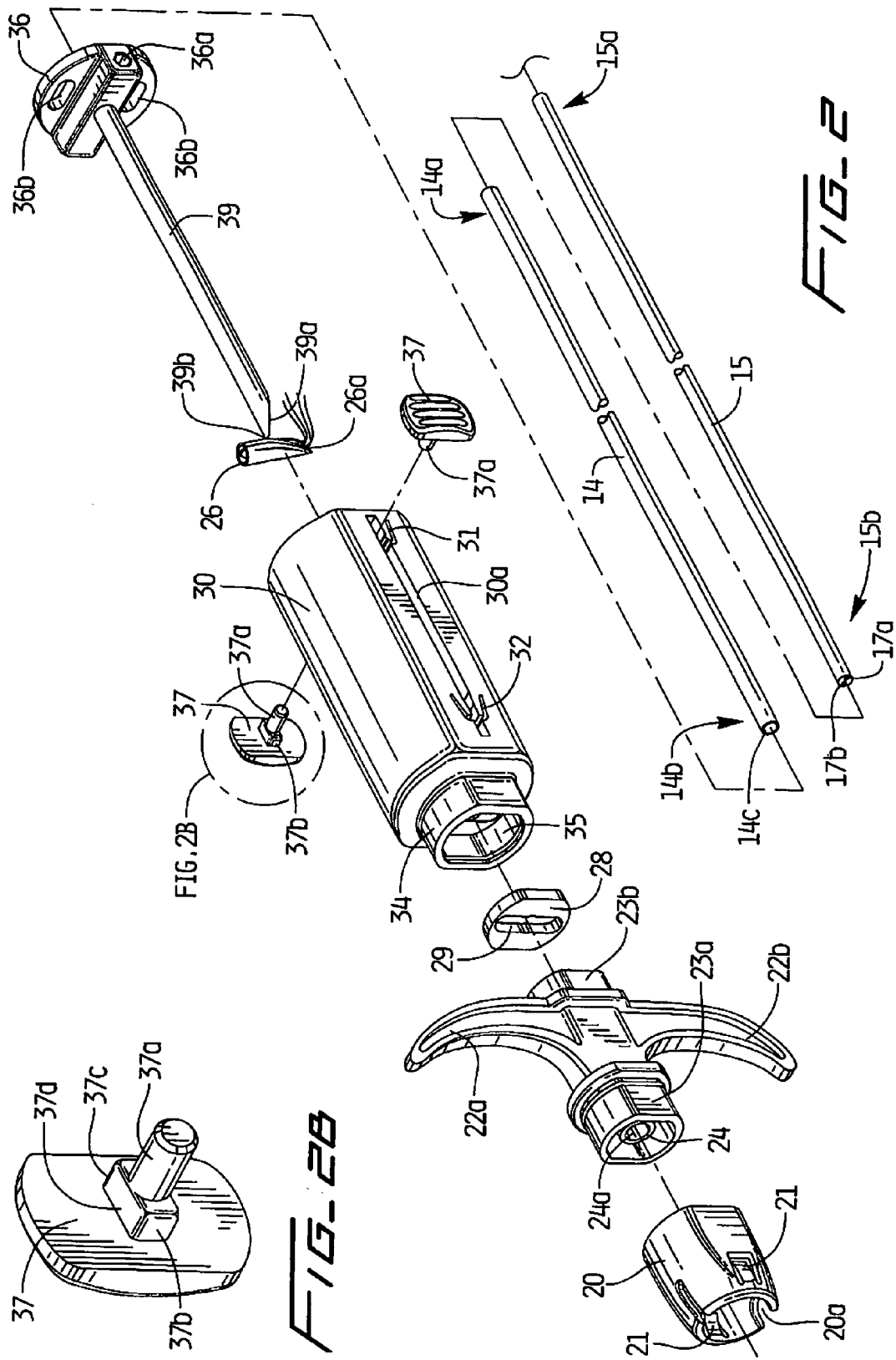

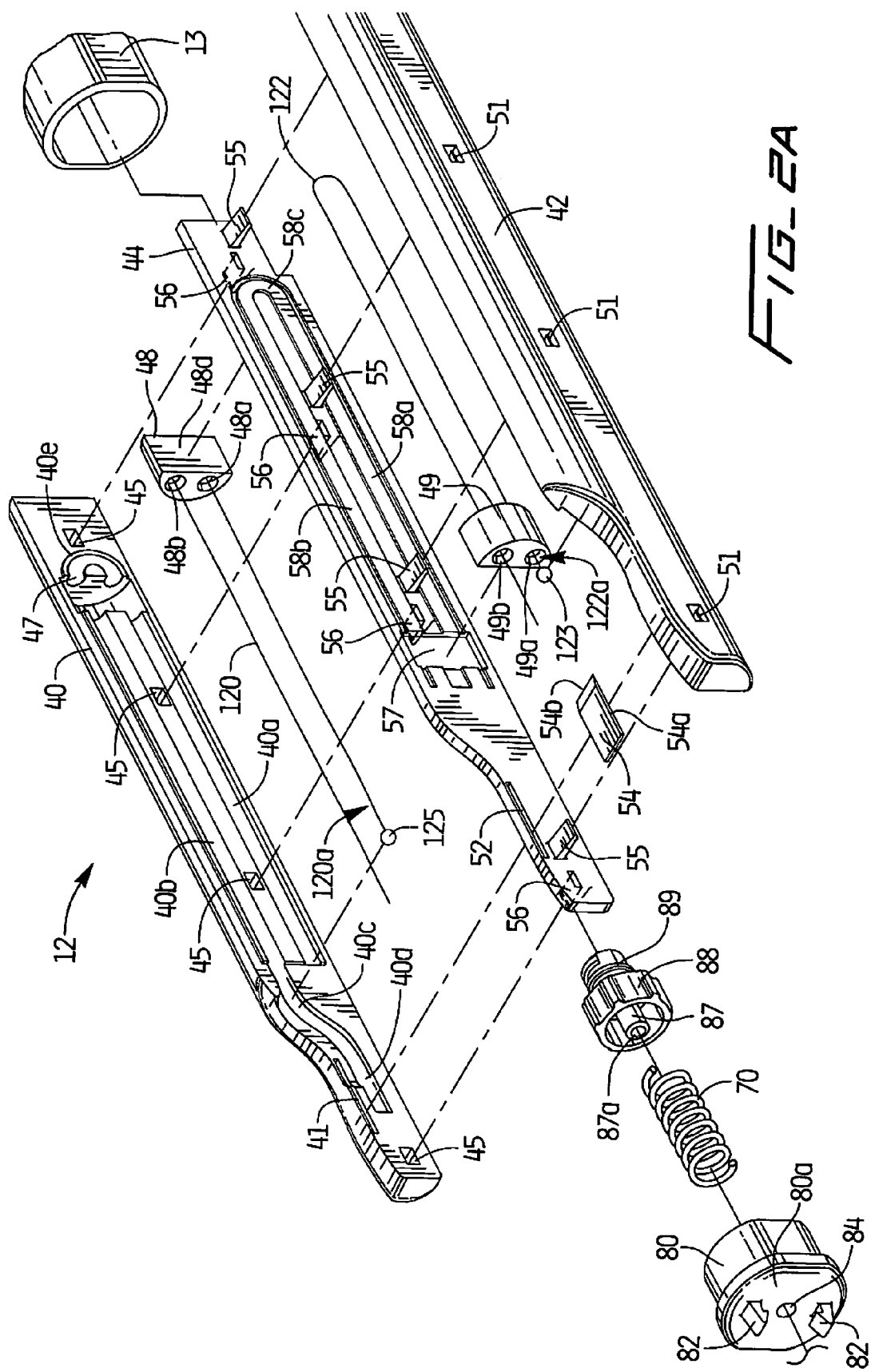
FIG_2A

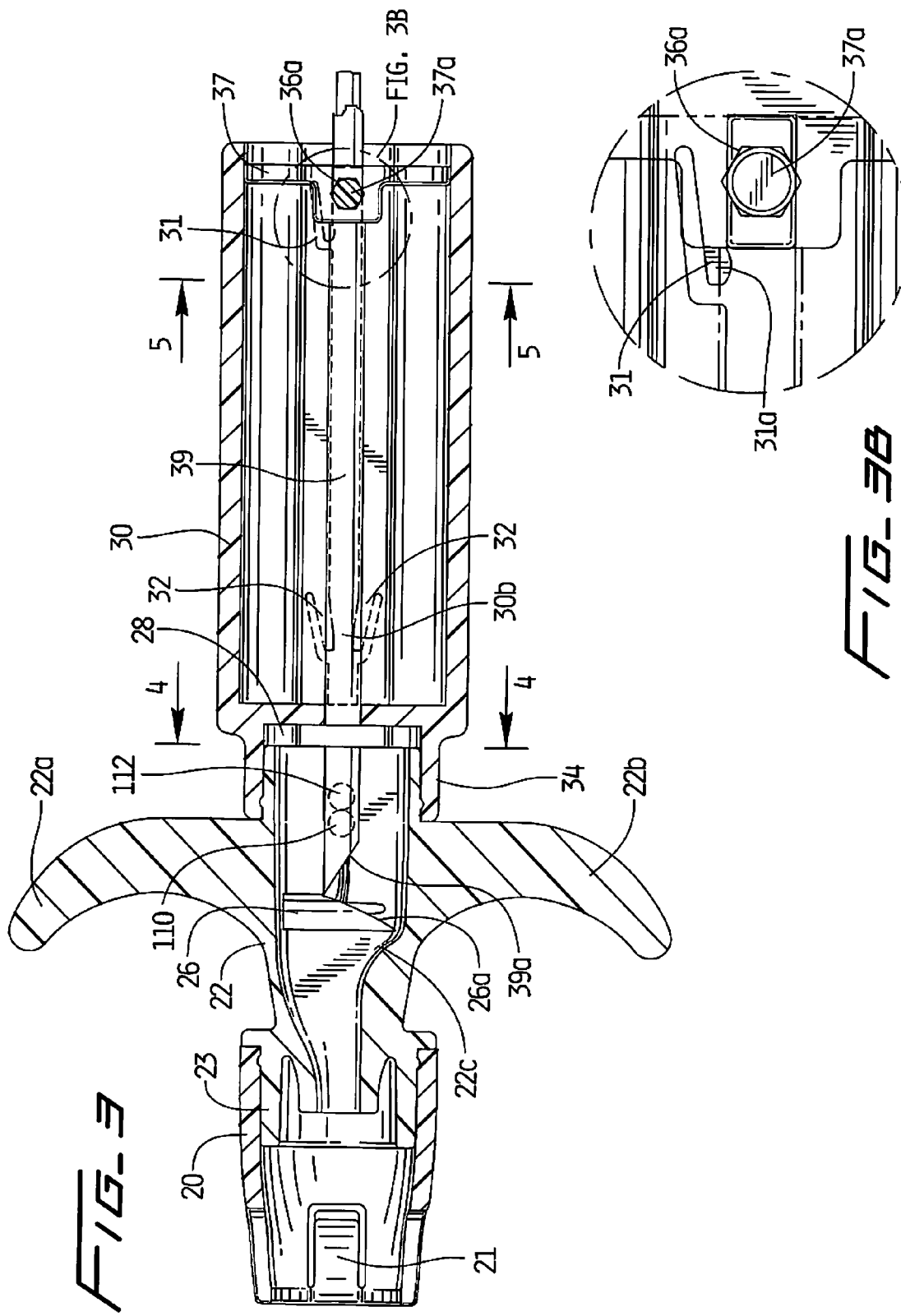

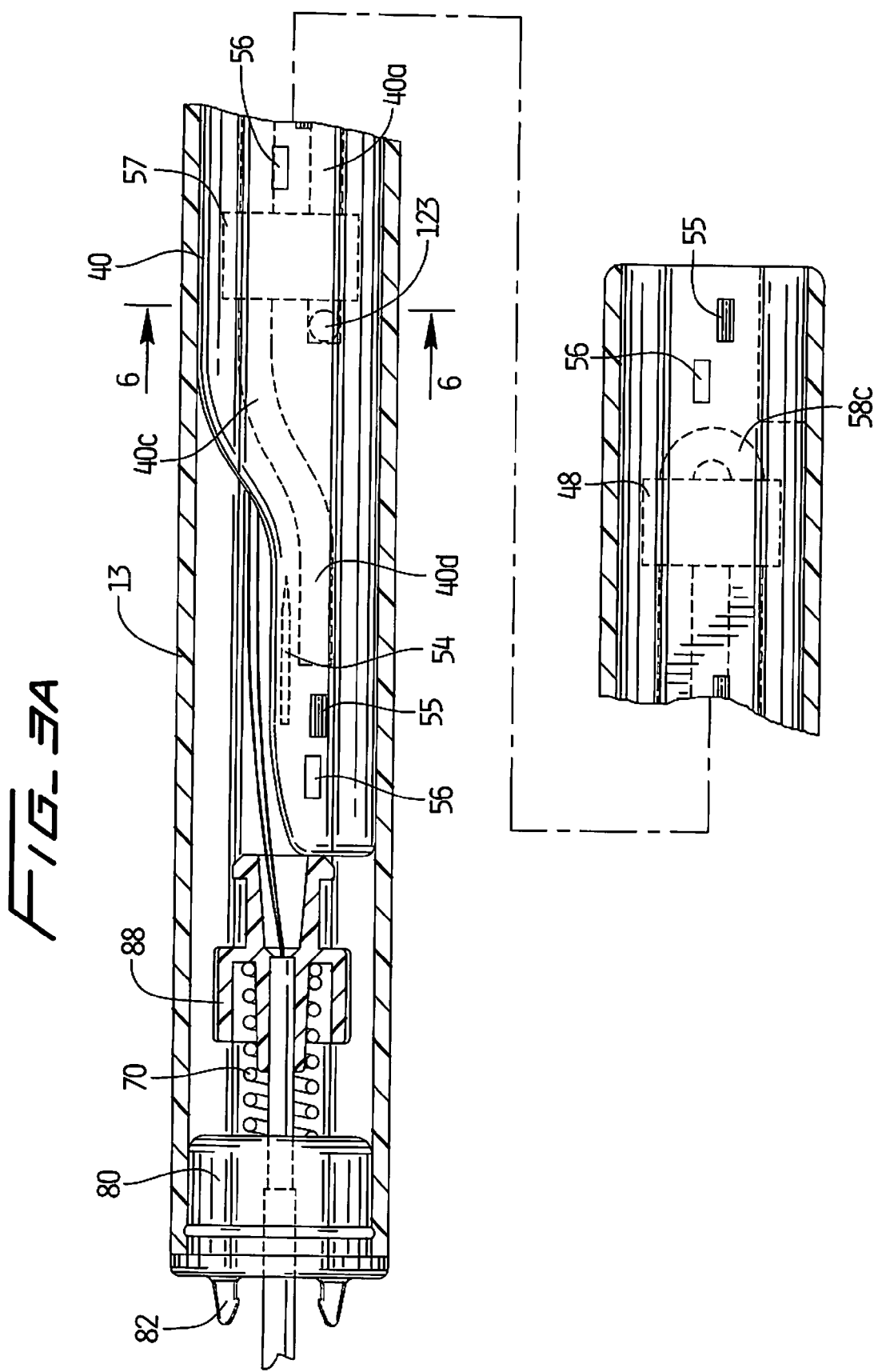

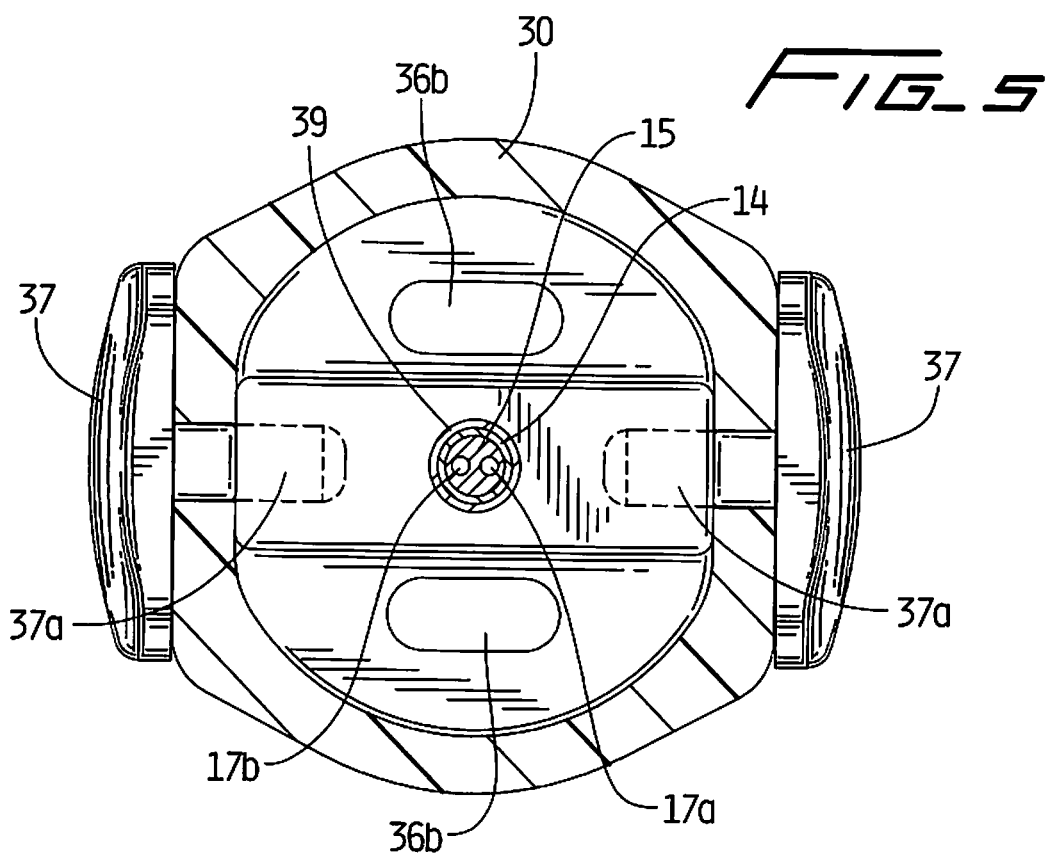
FIG_5
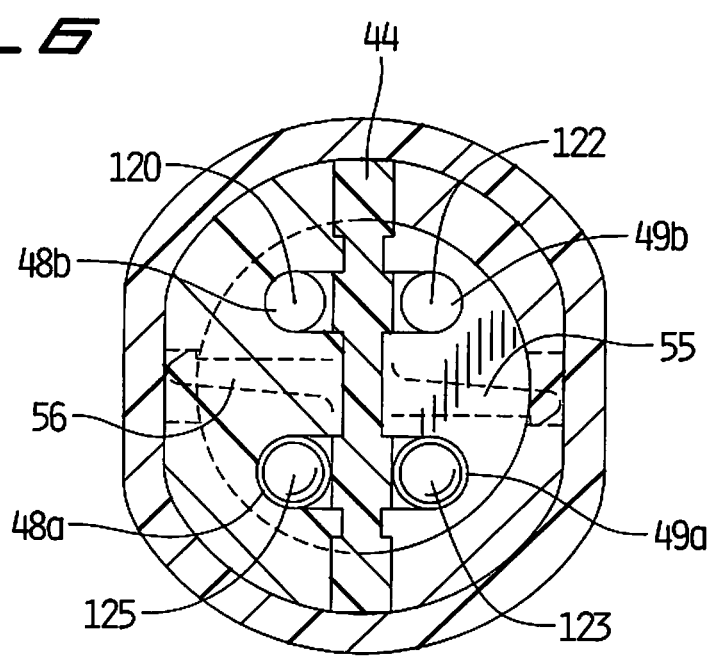
FIG_6

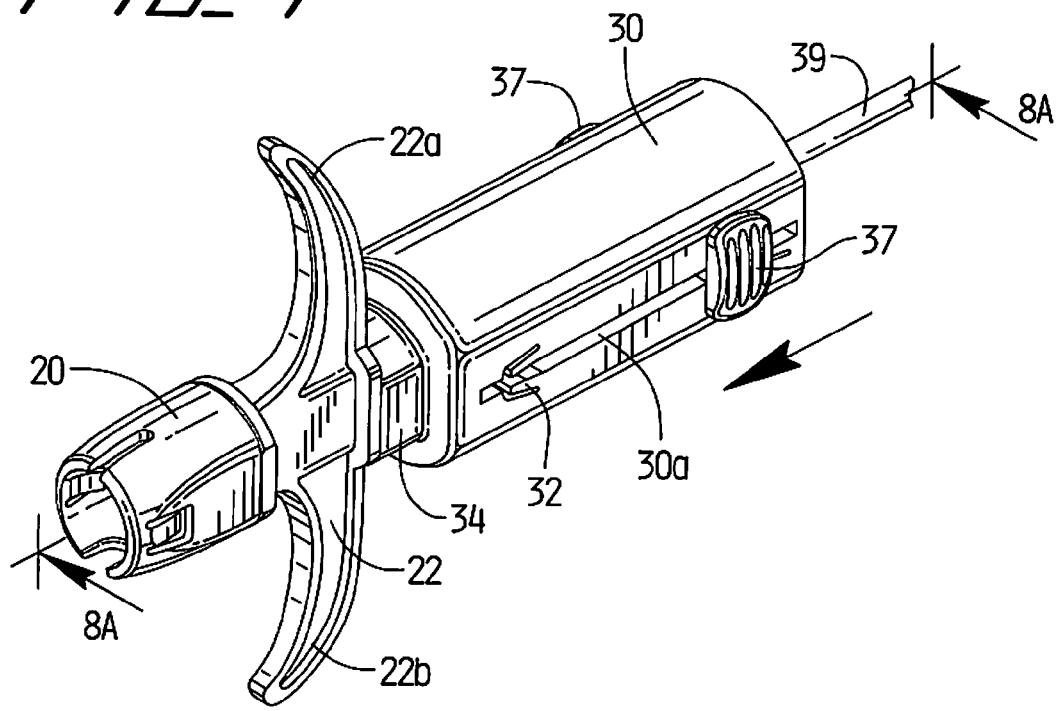
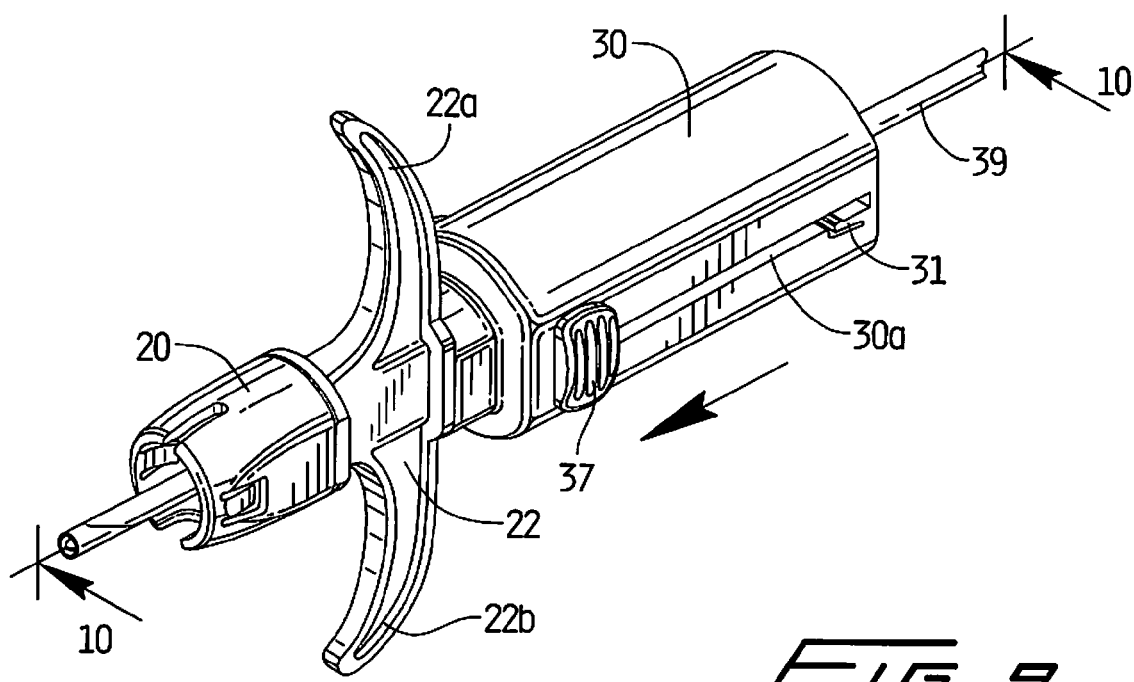

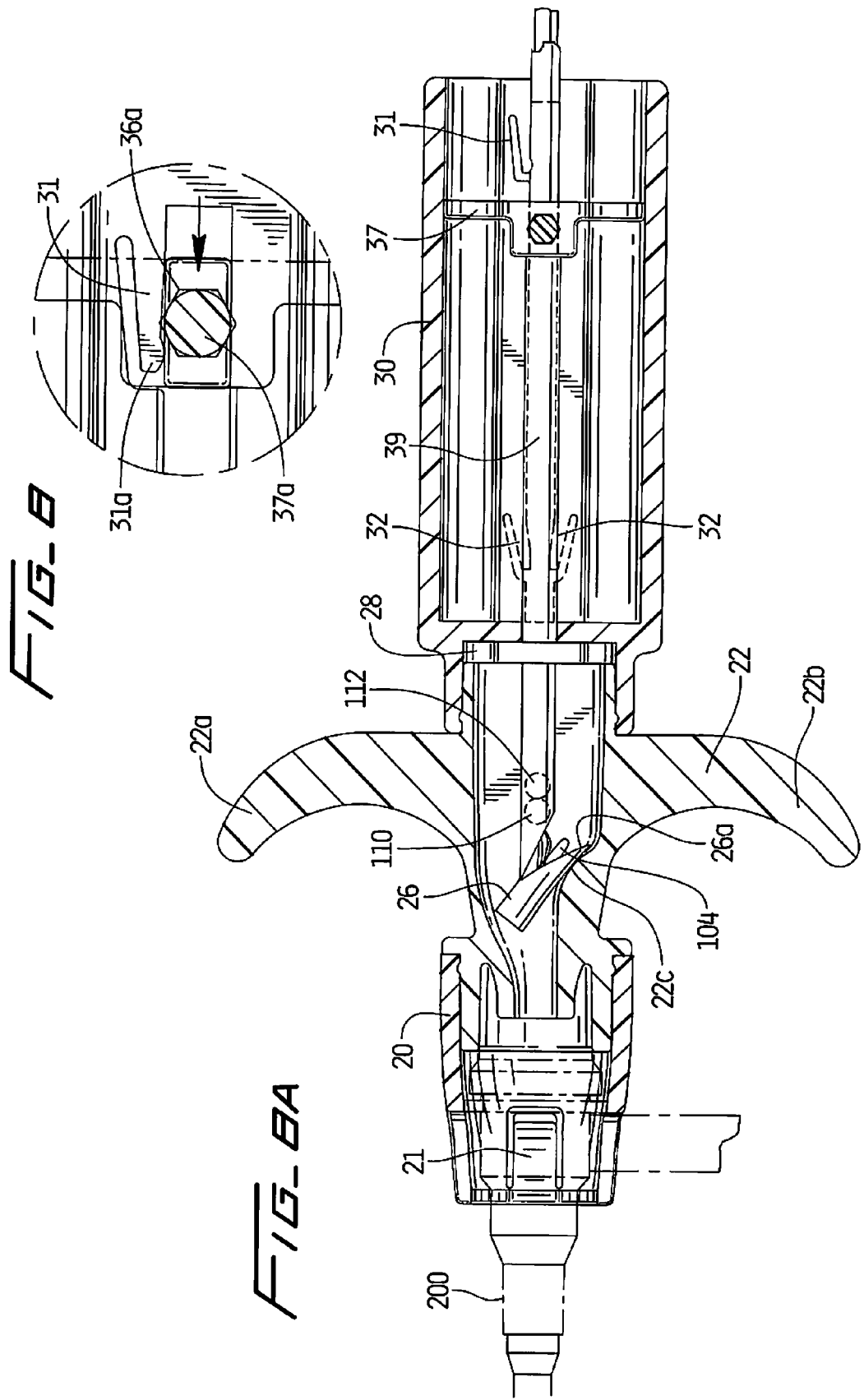

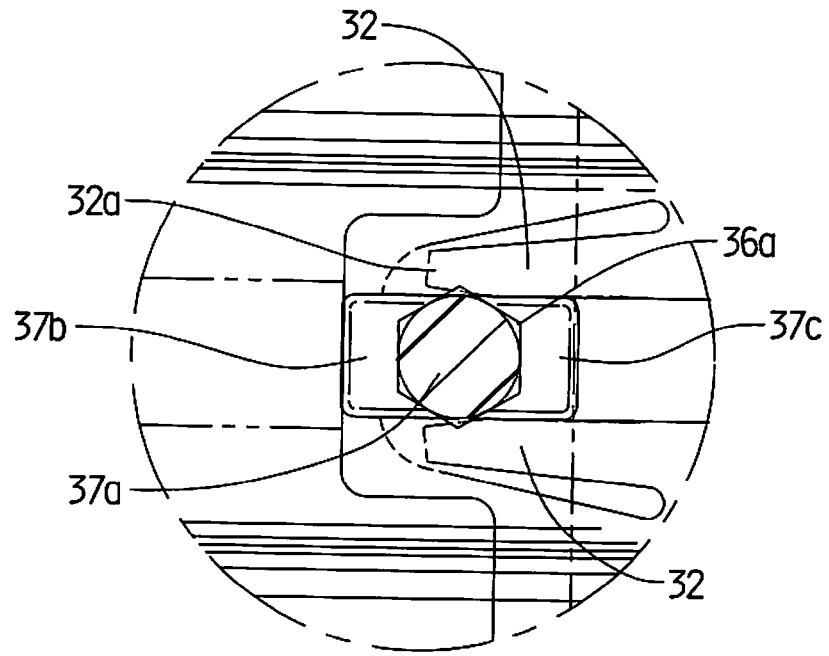
FIG_8B
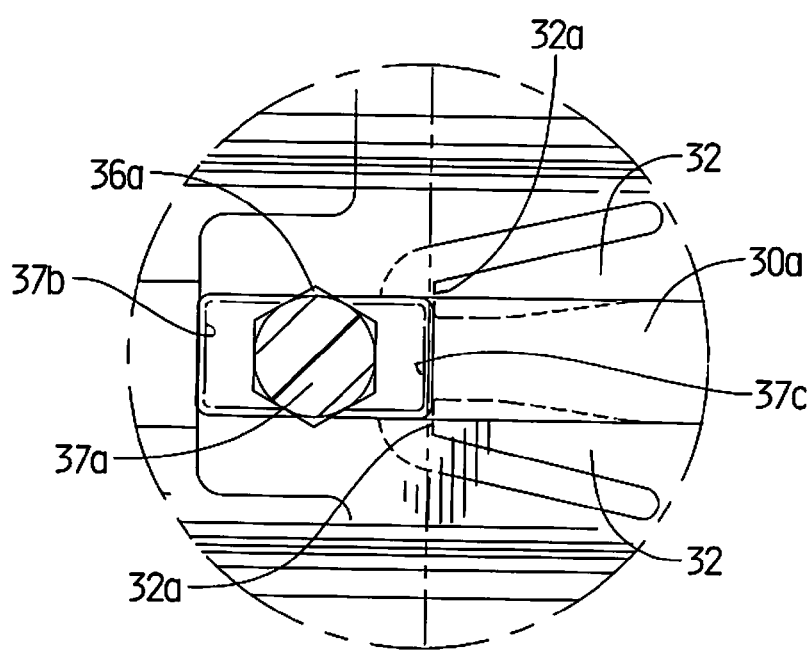
FIG_8C

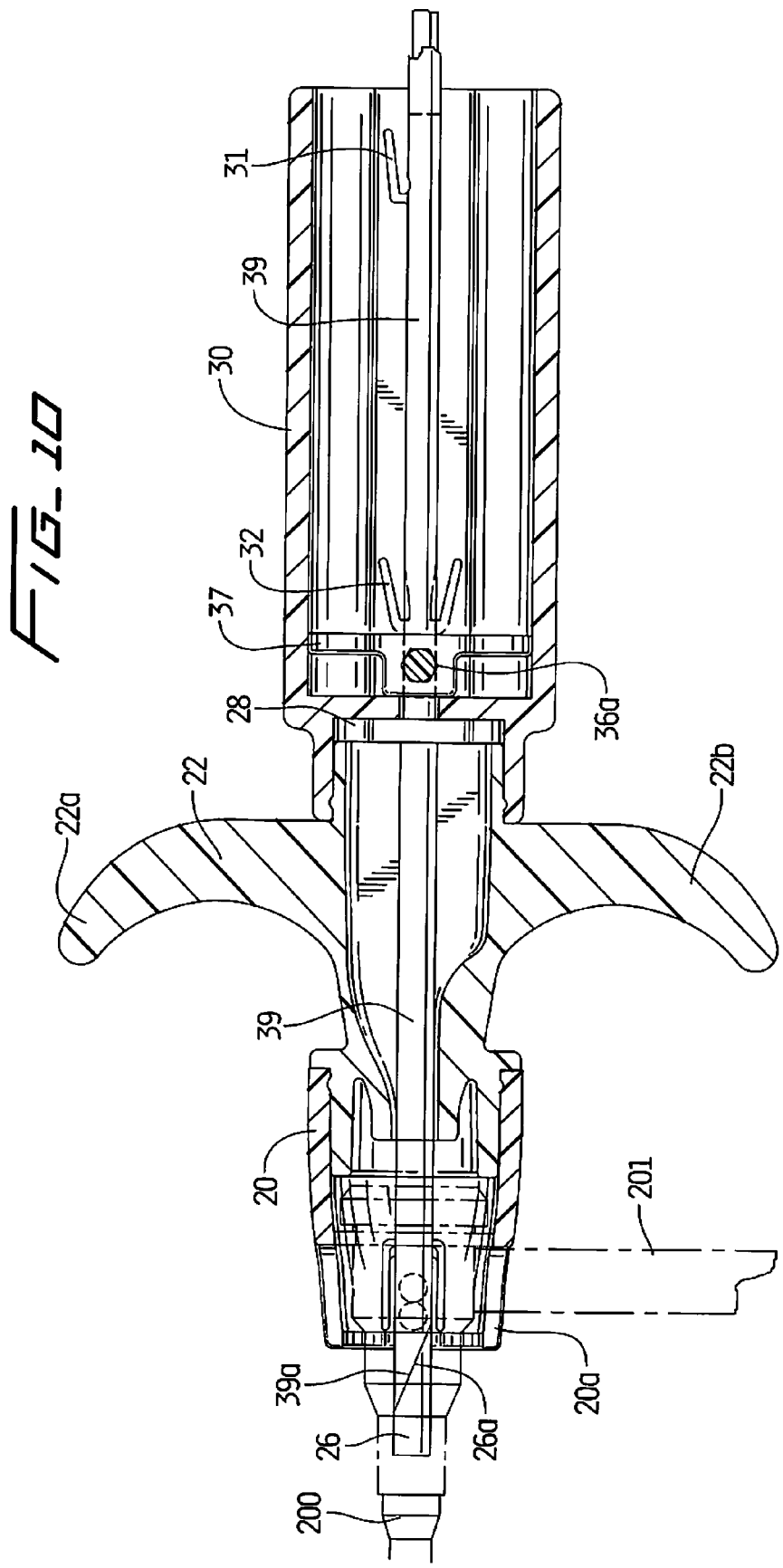

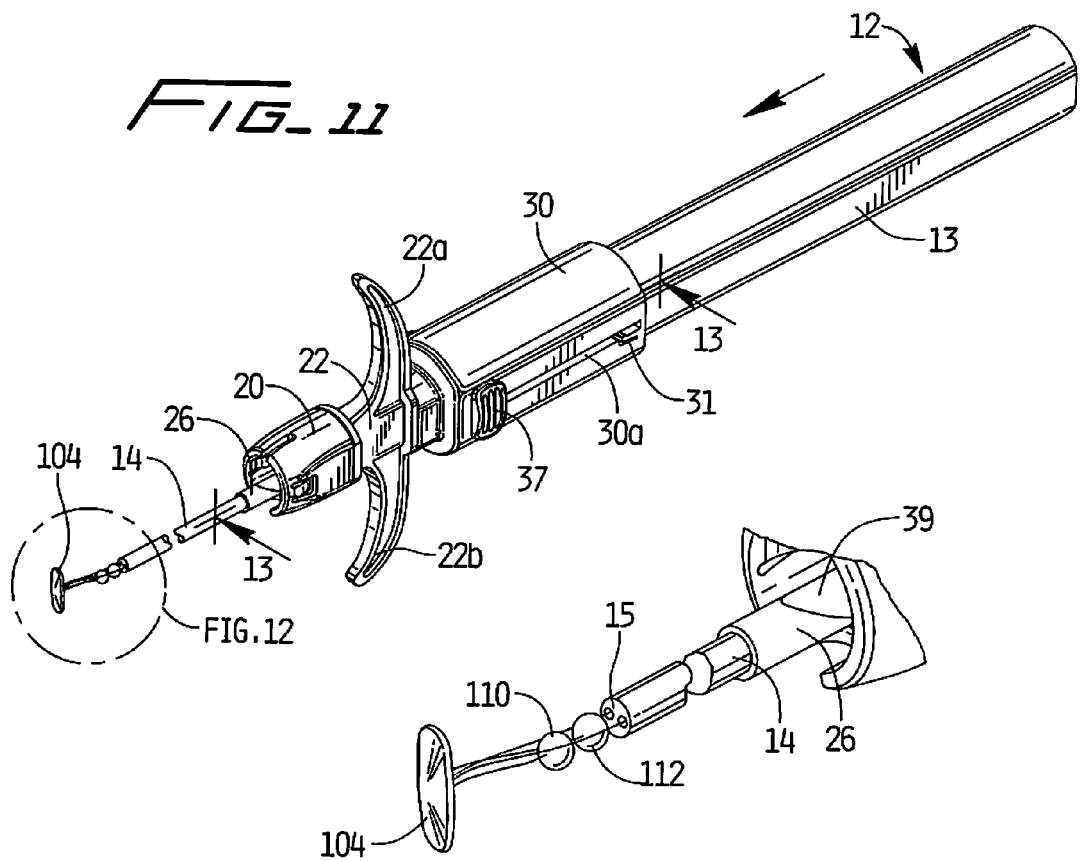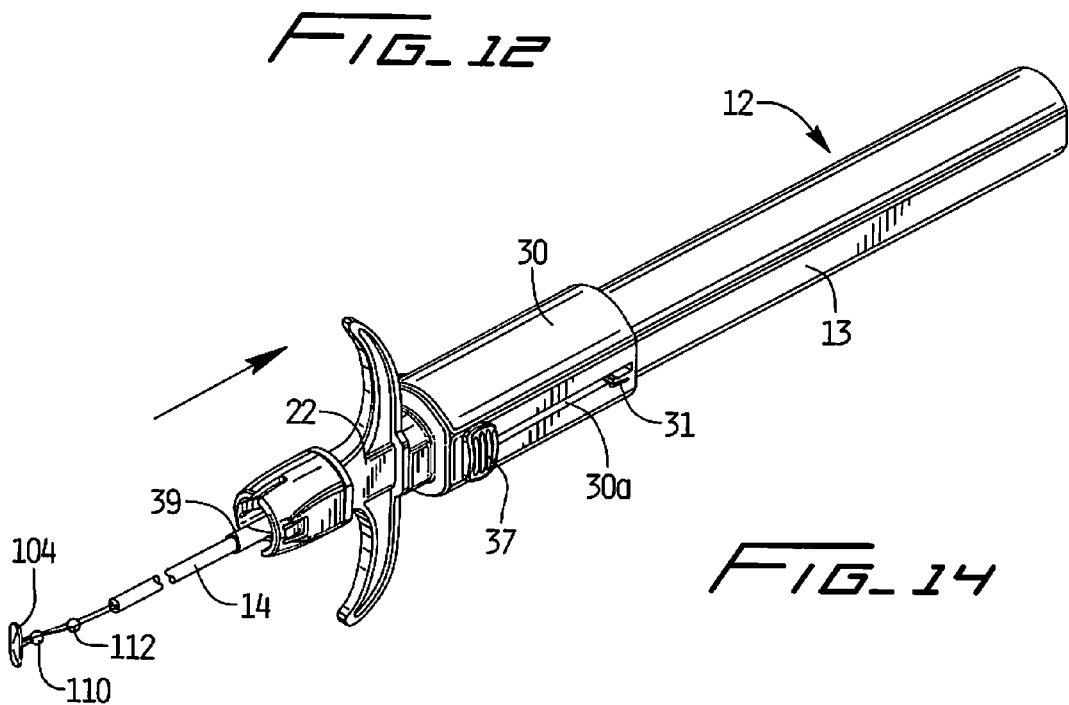

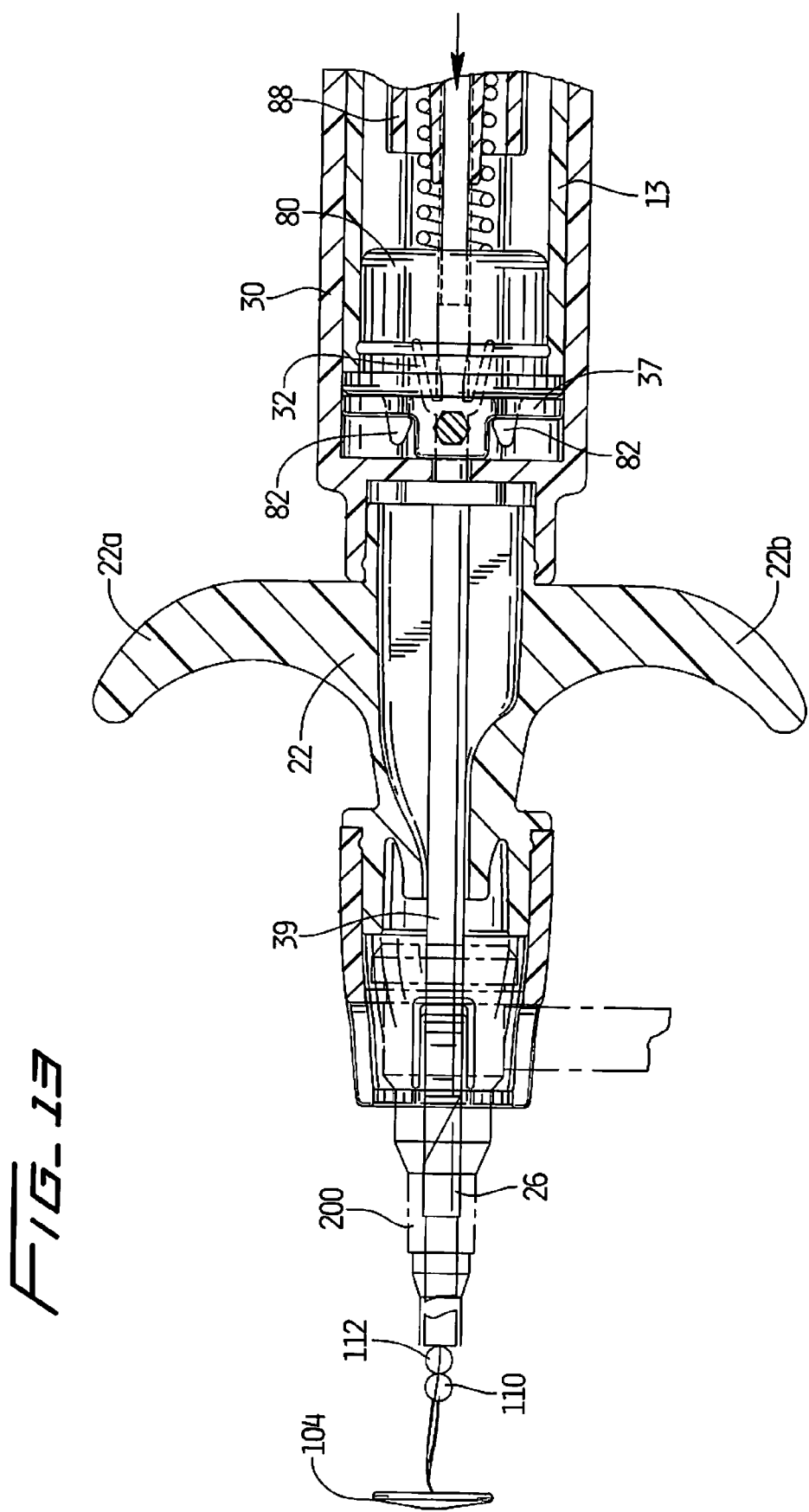
FIG_13

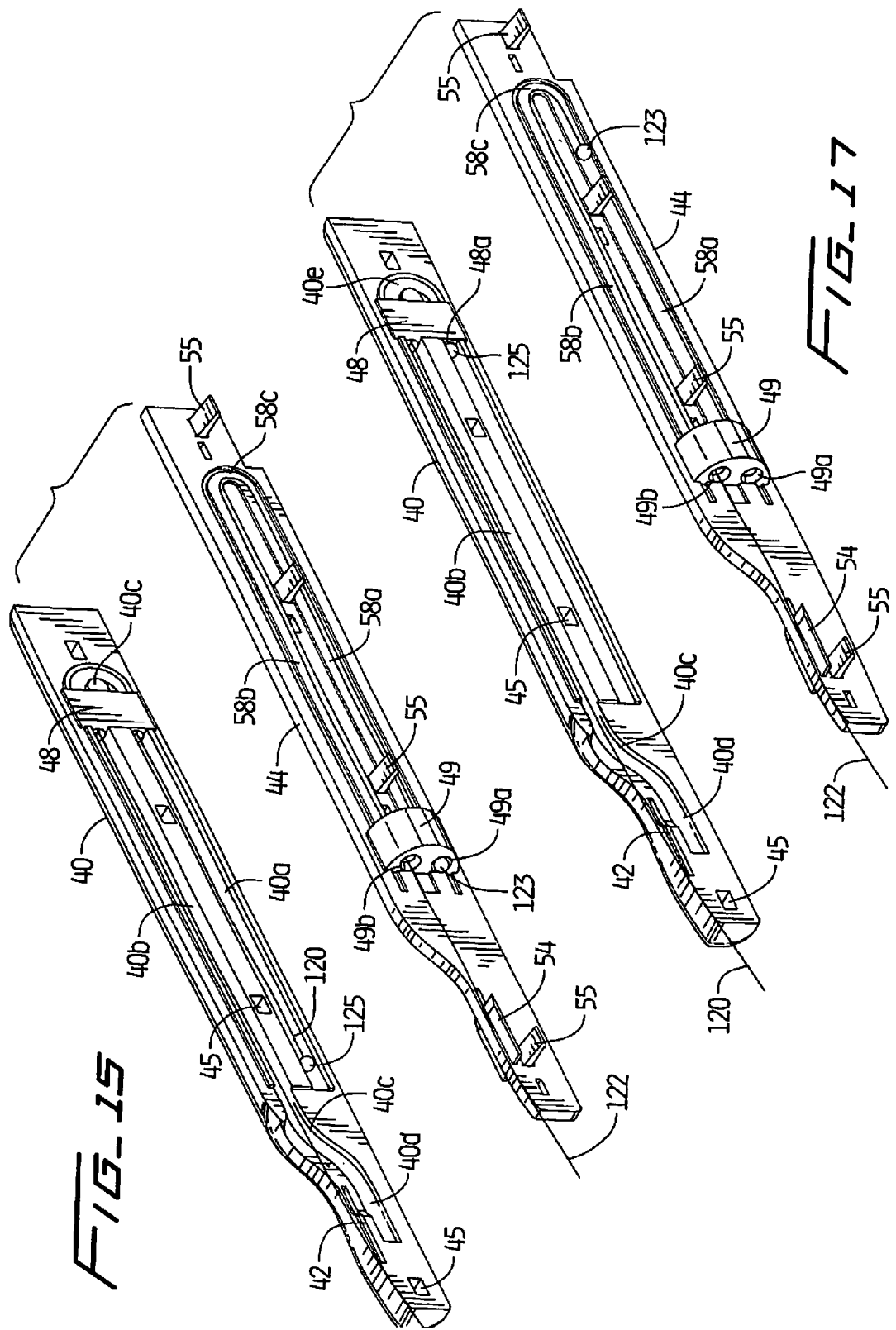

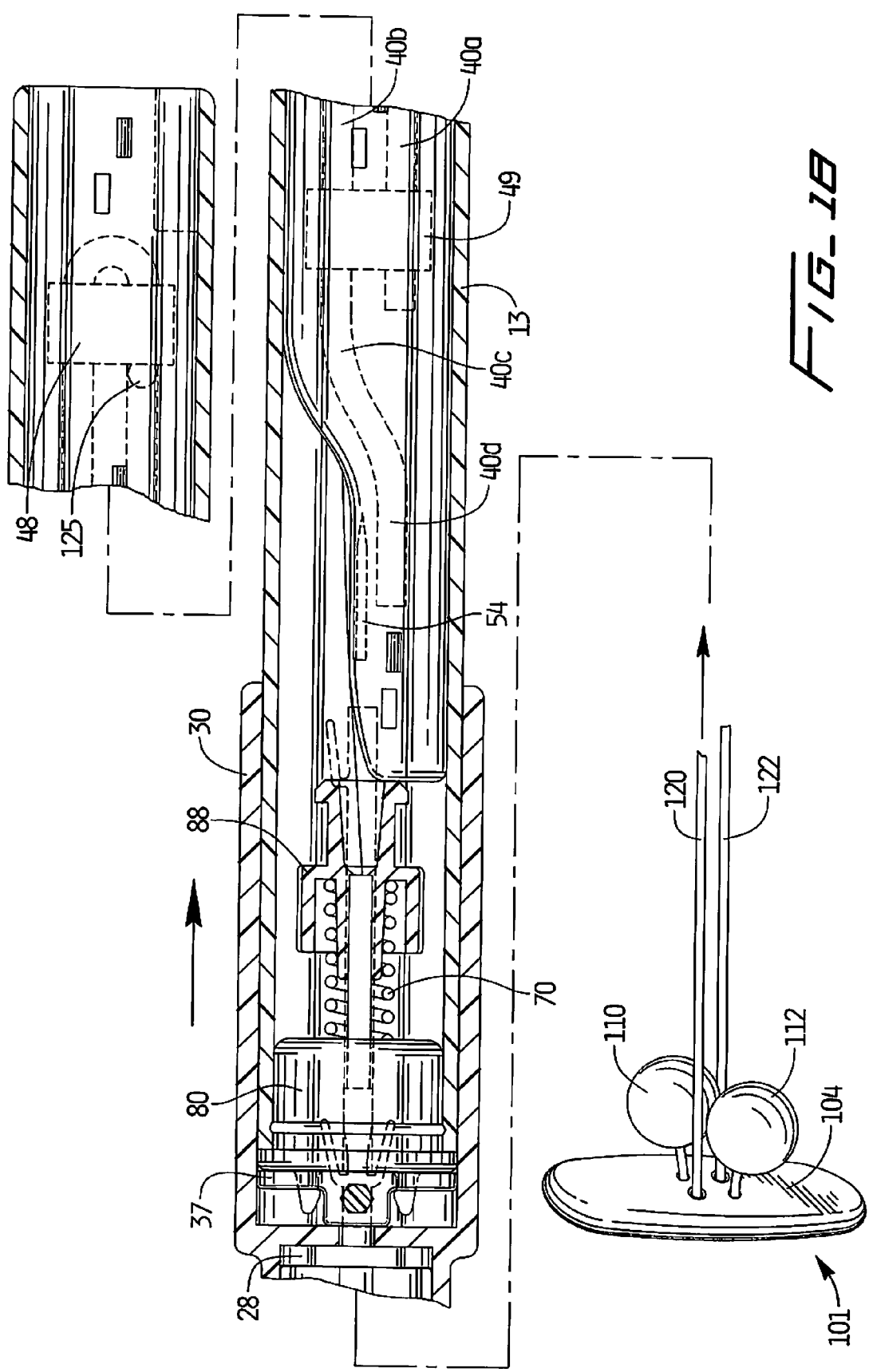

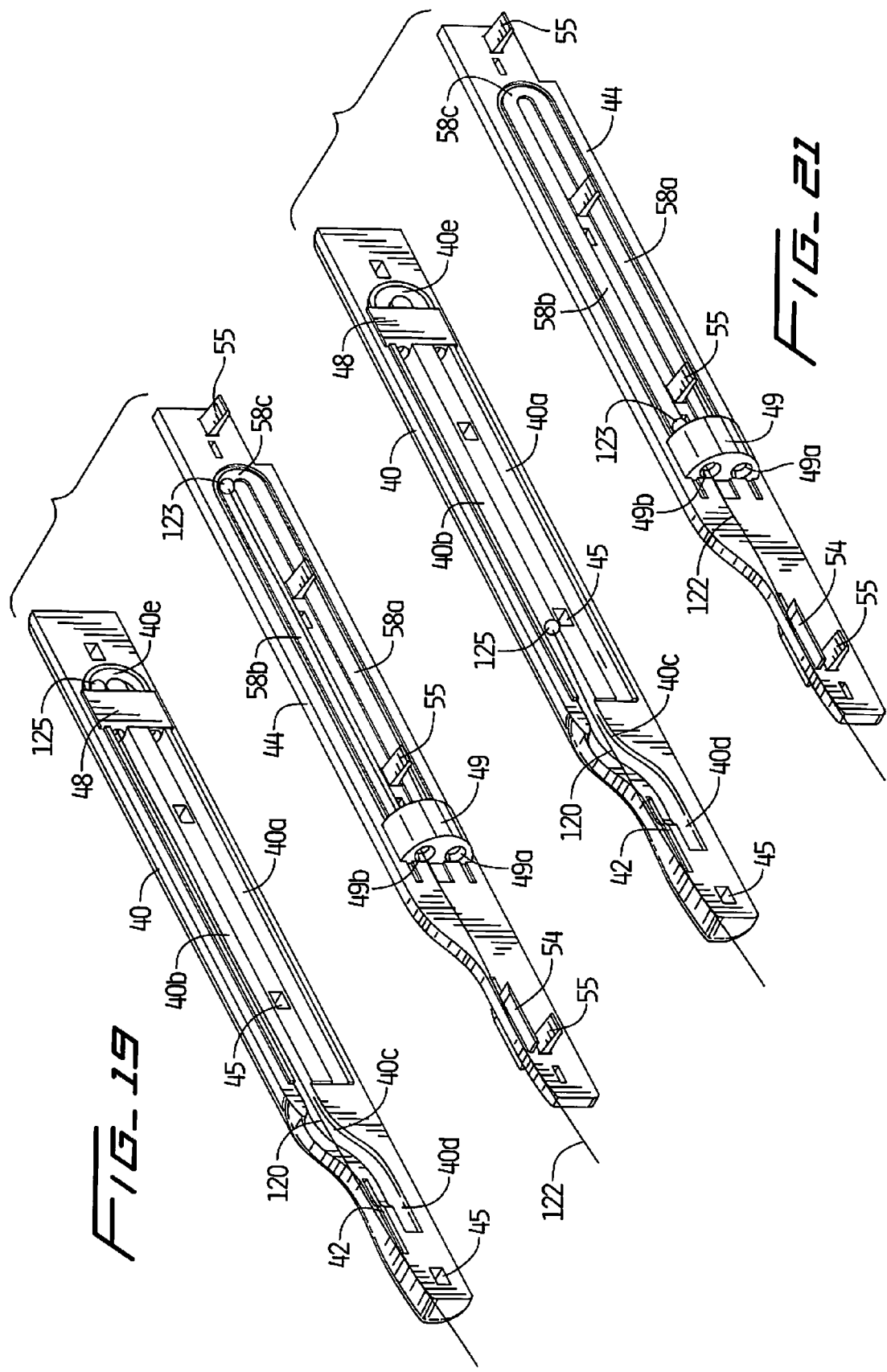

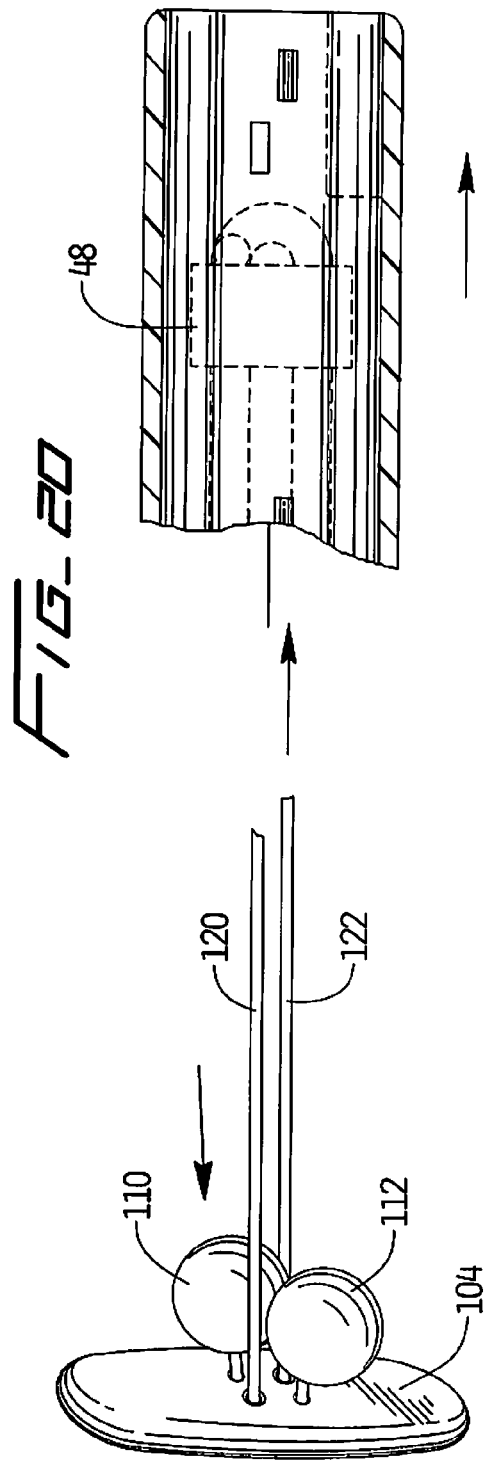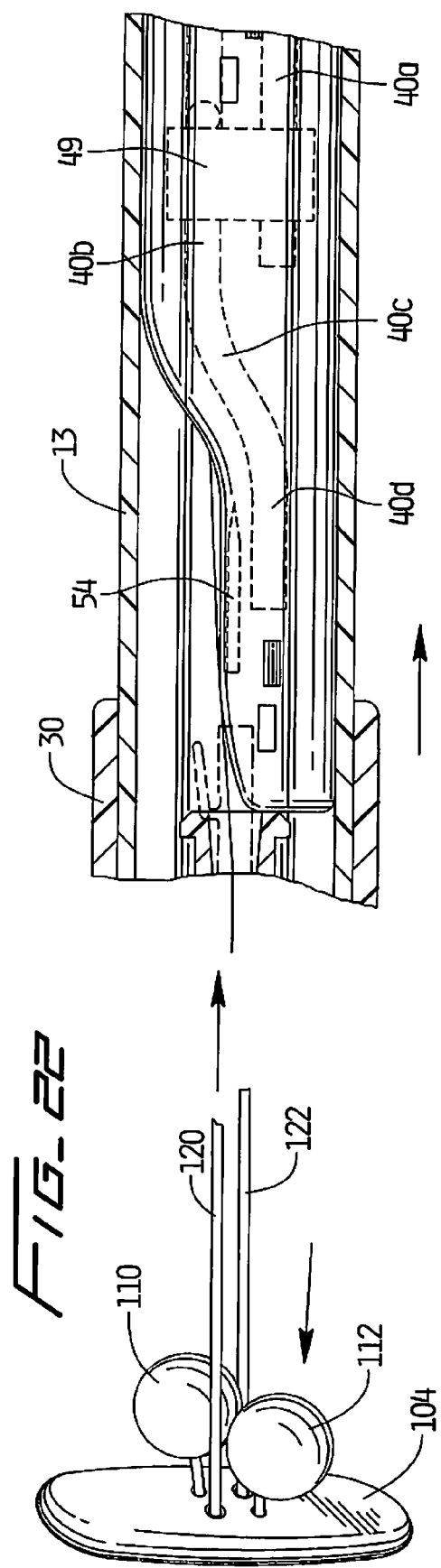

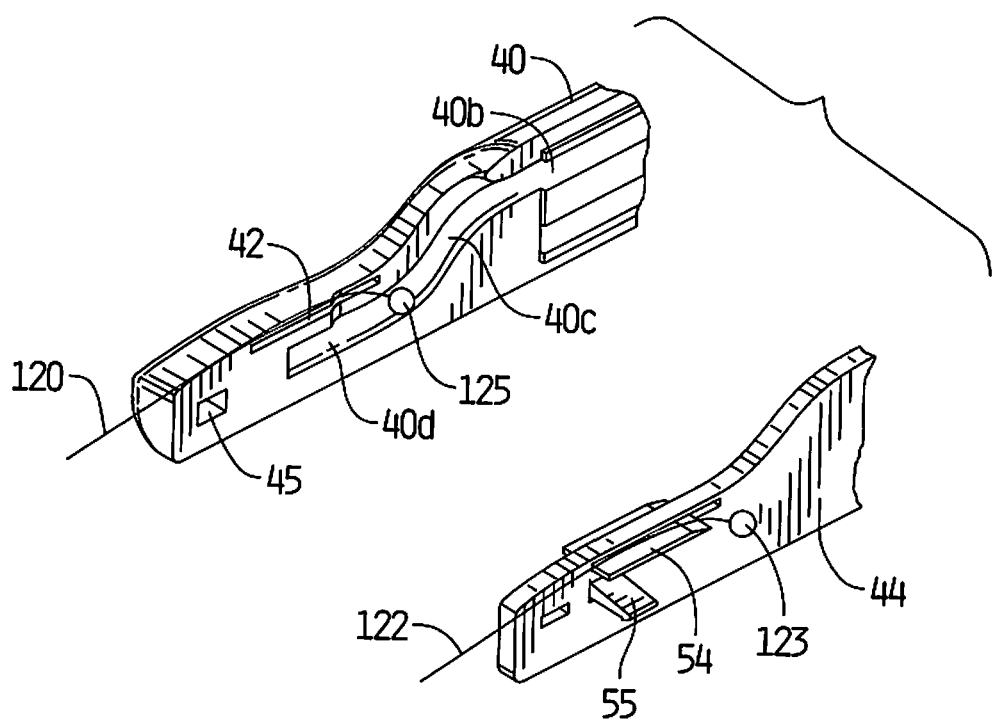
FIG_23
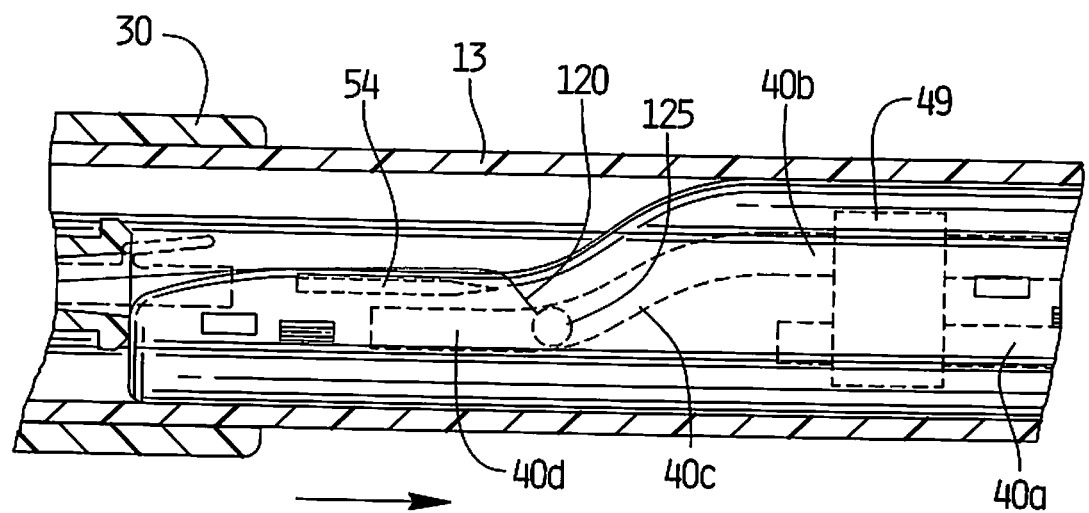
FIG_24

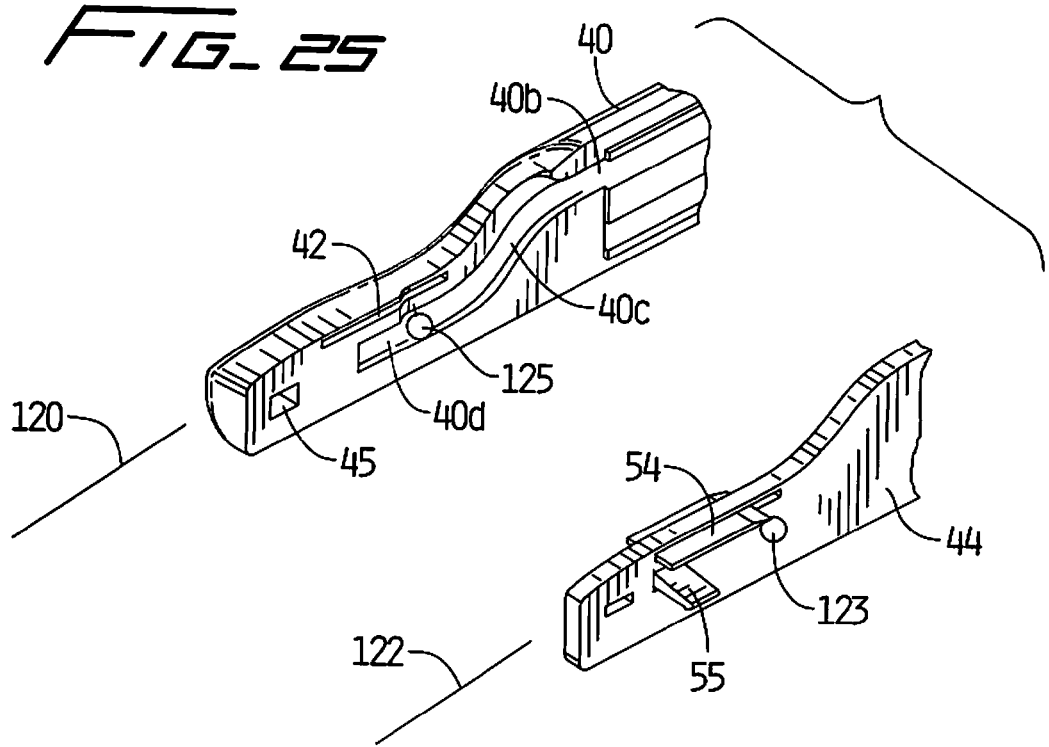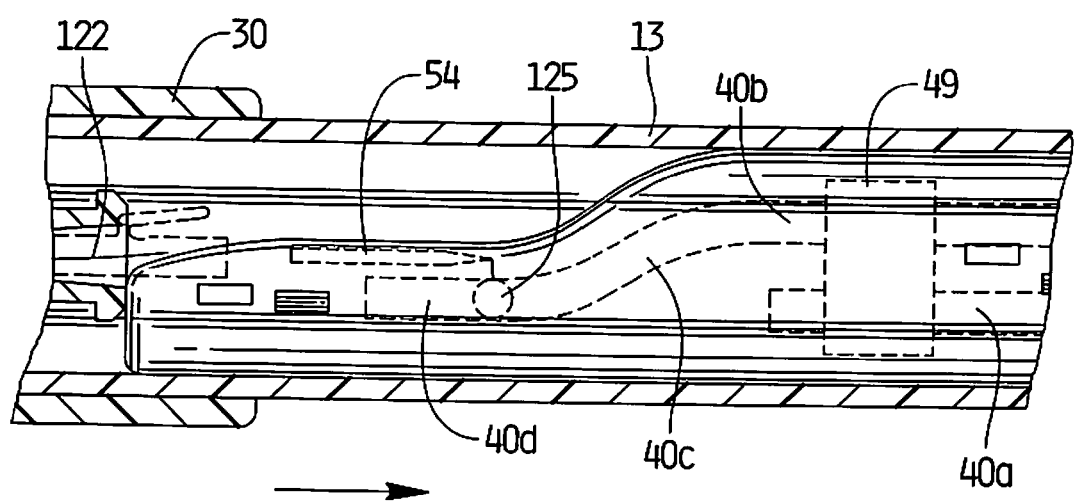

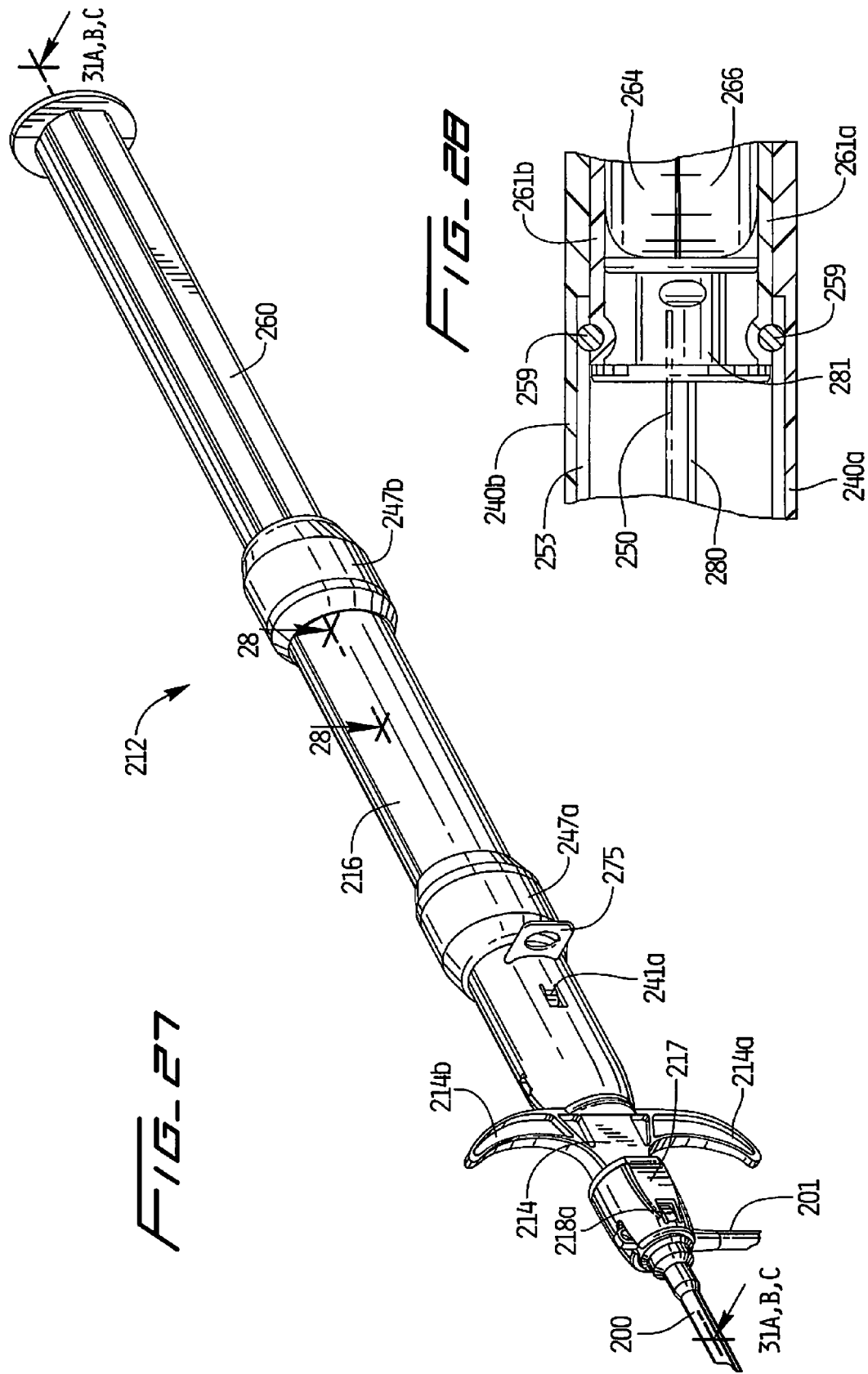

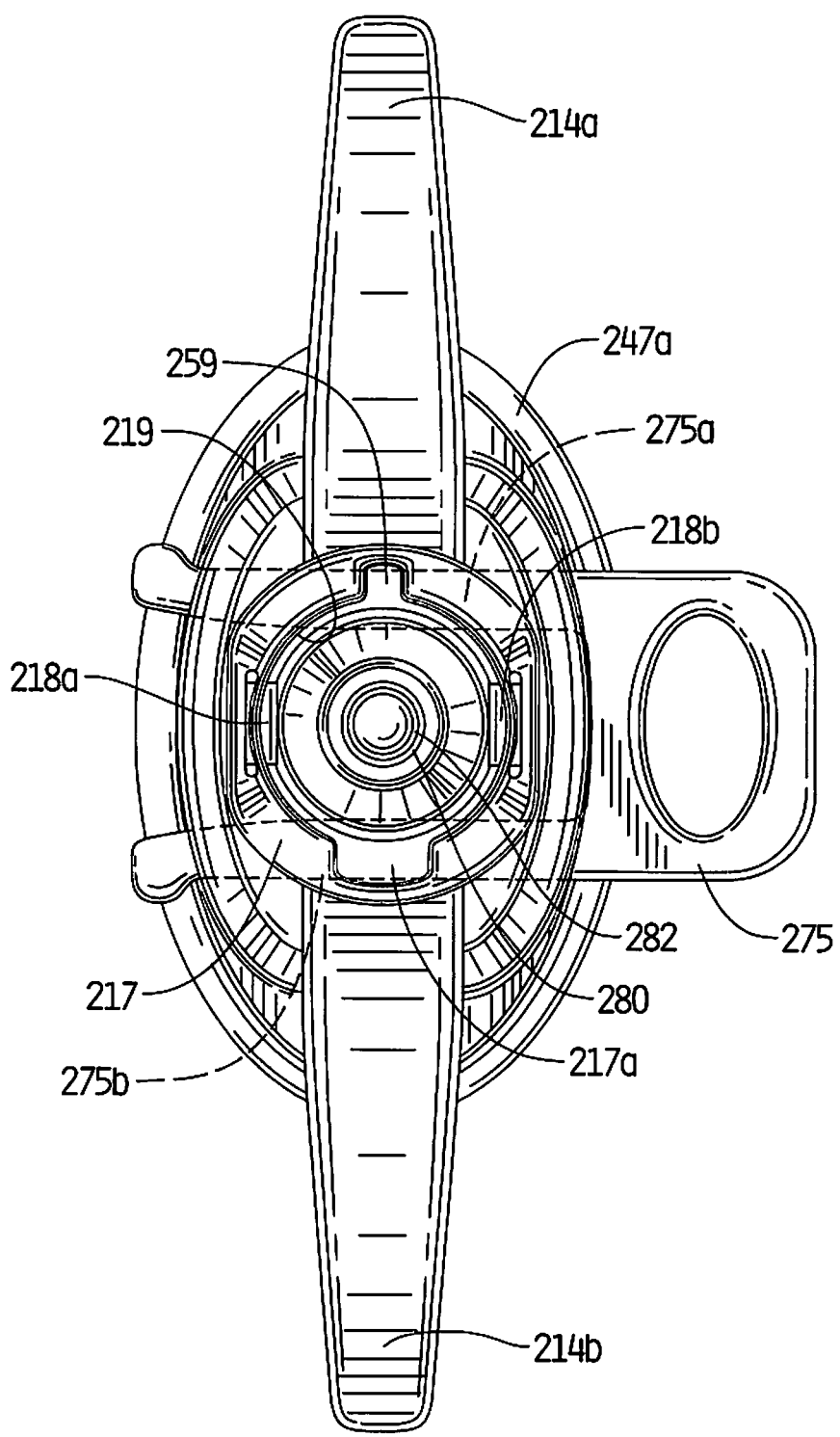
FIG_29

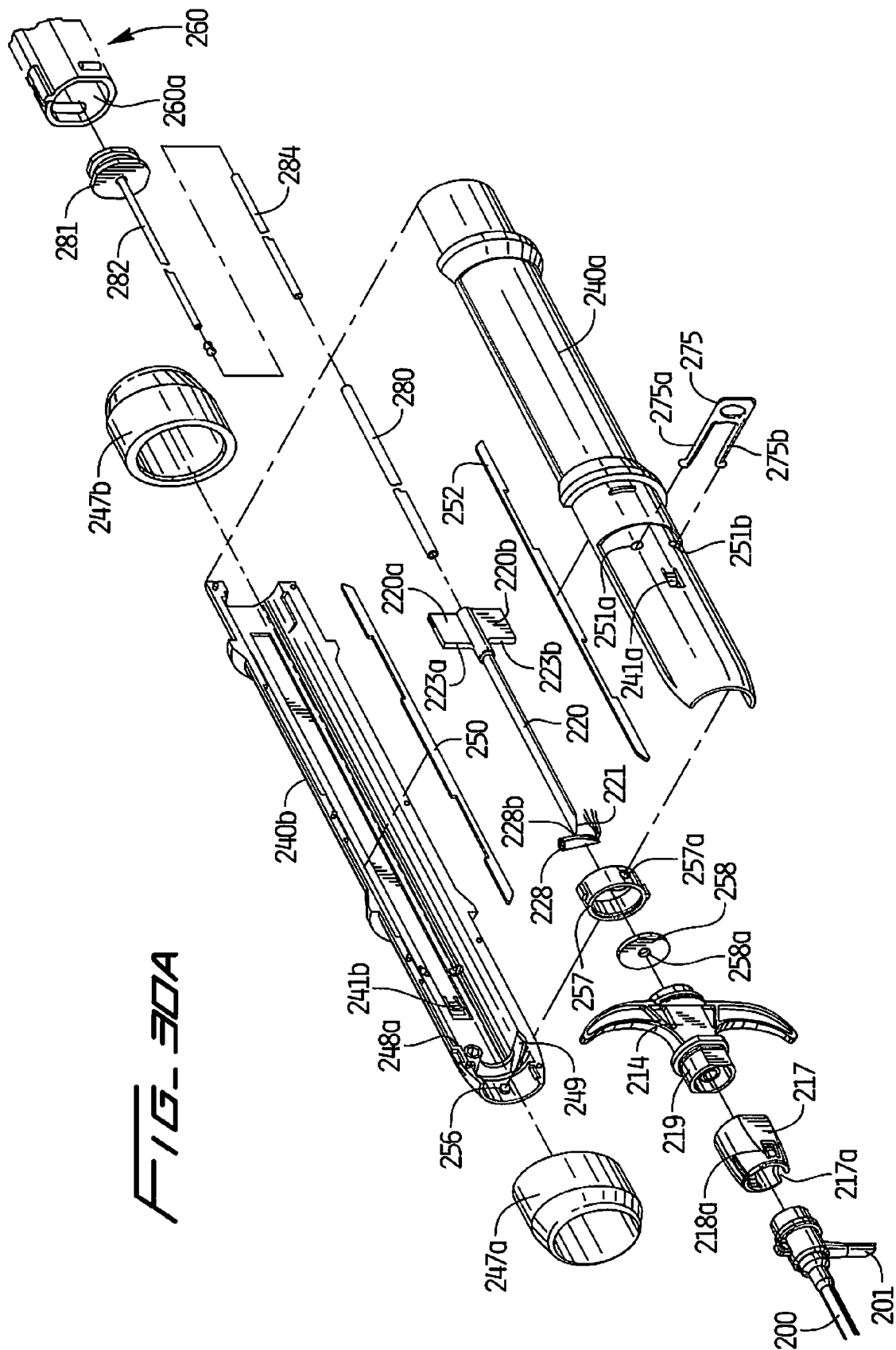

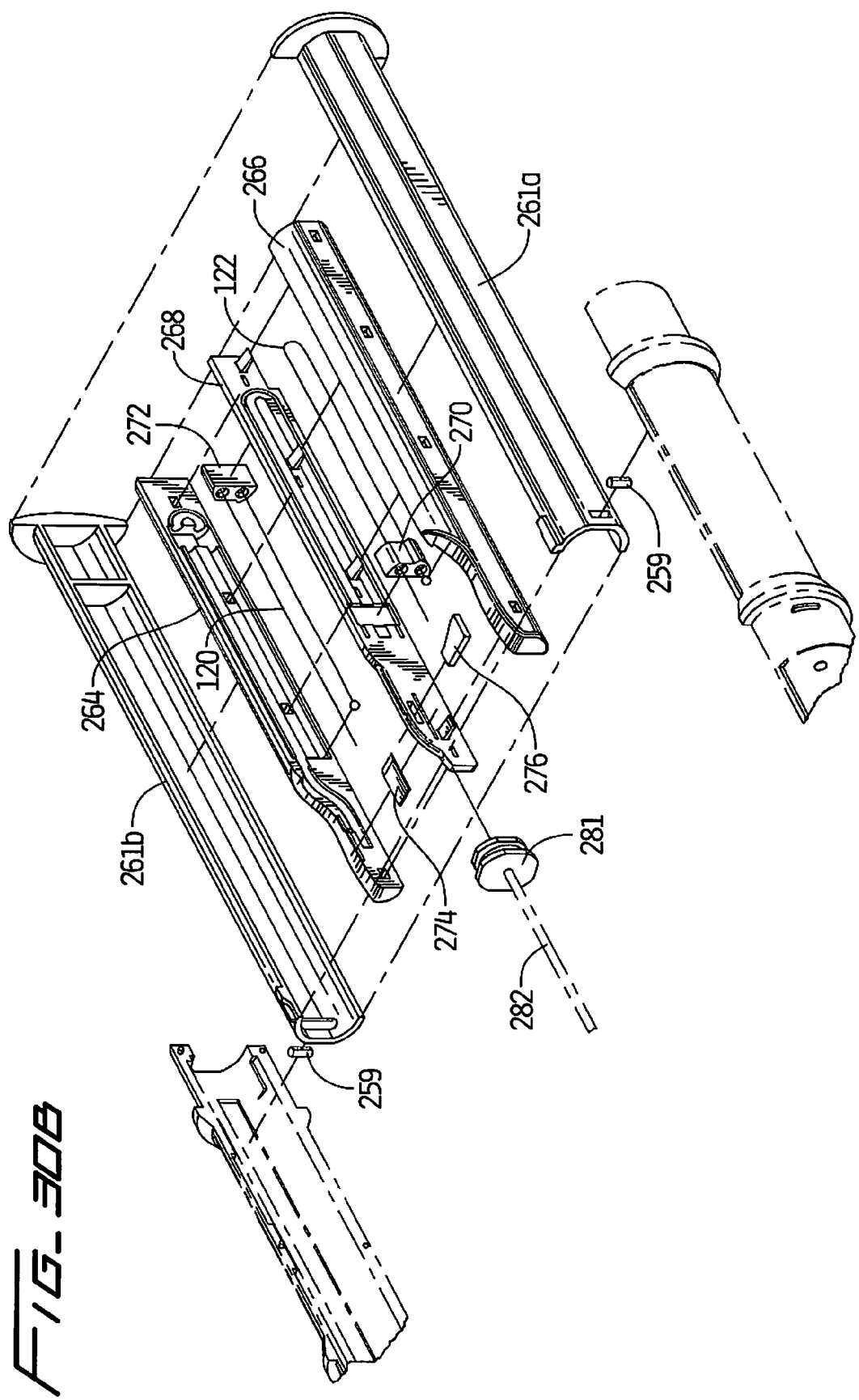

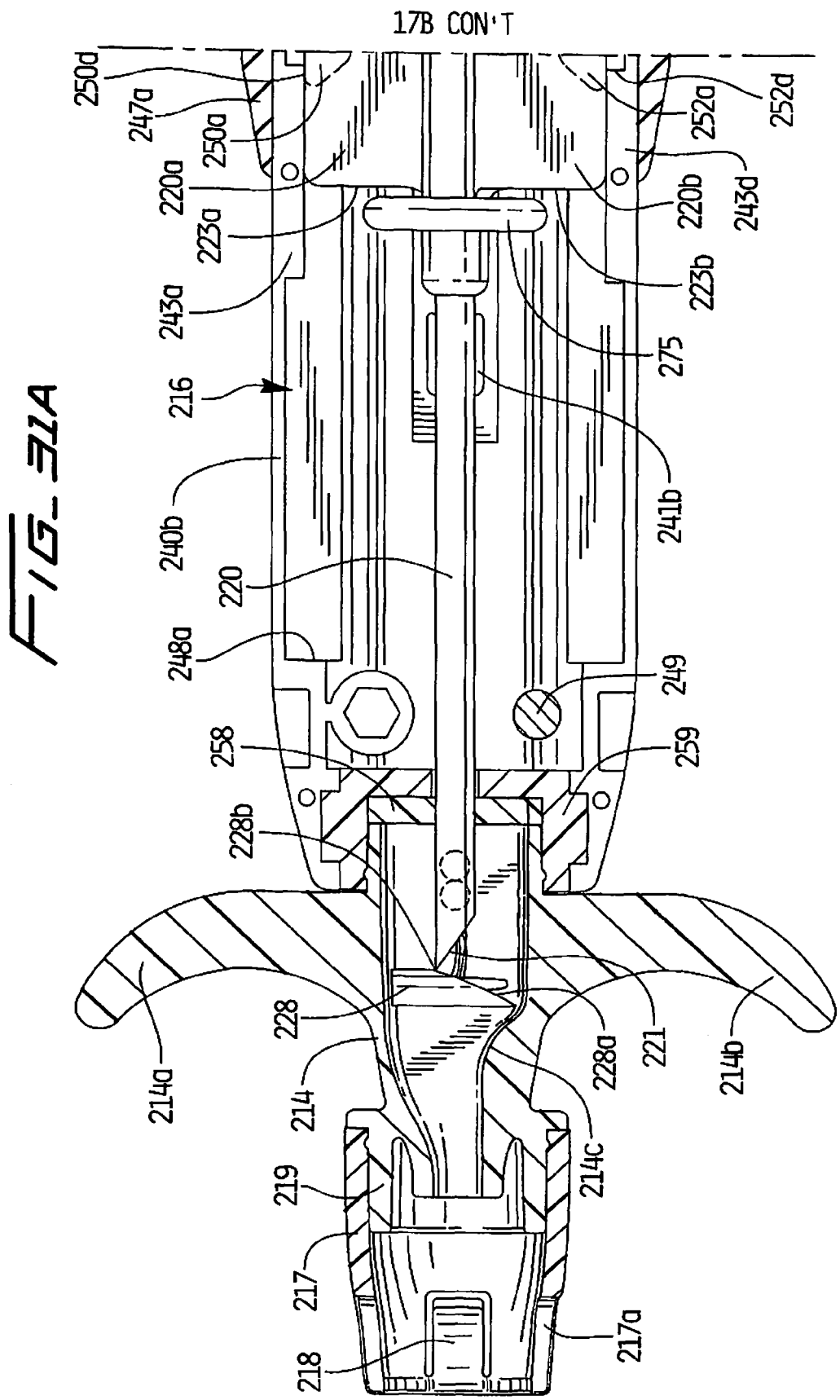

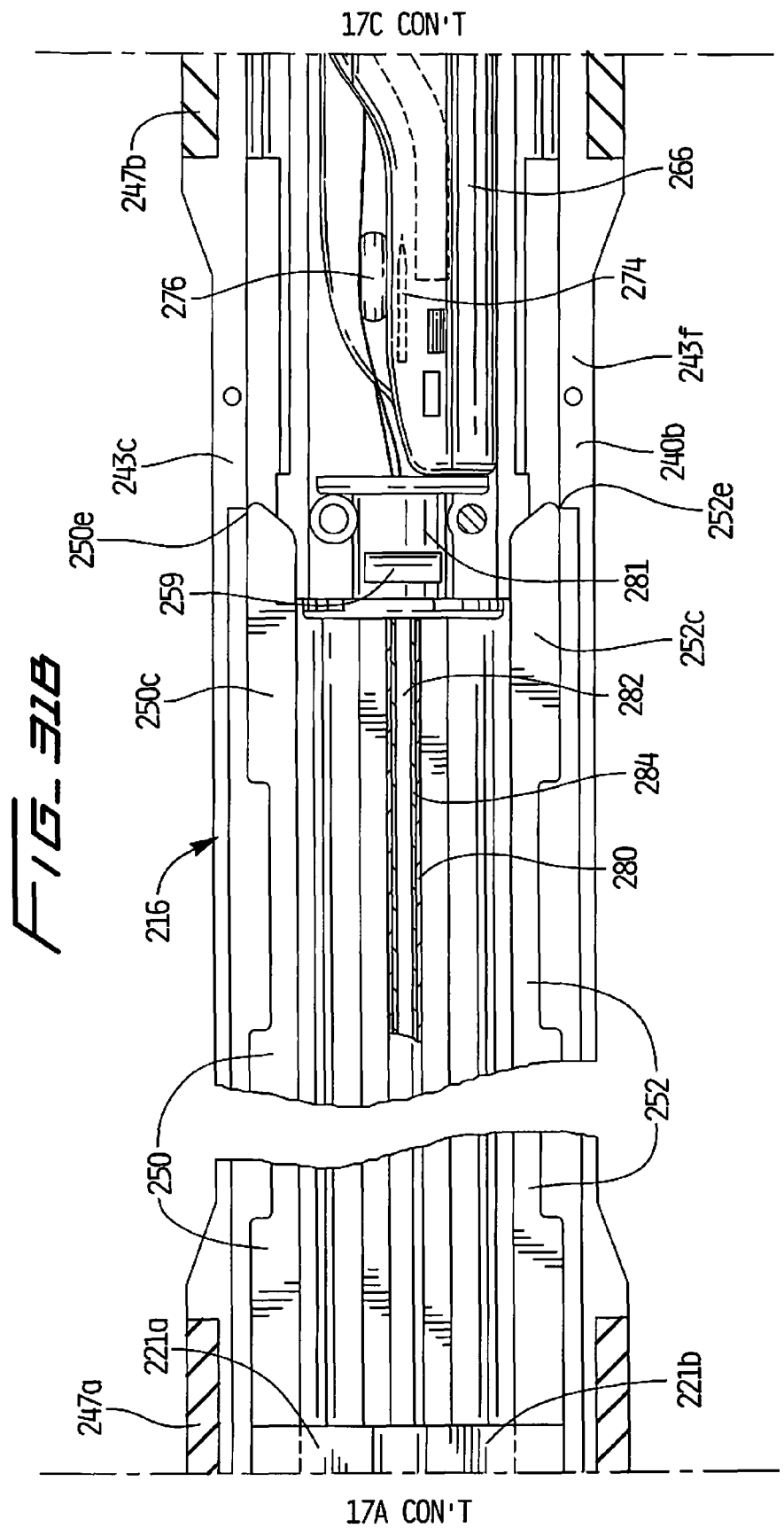

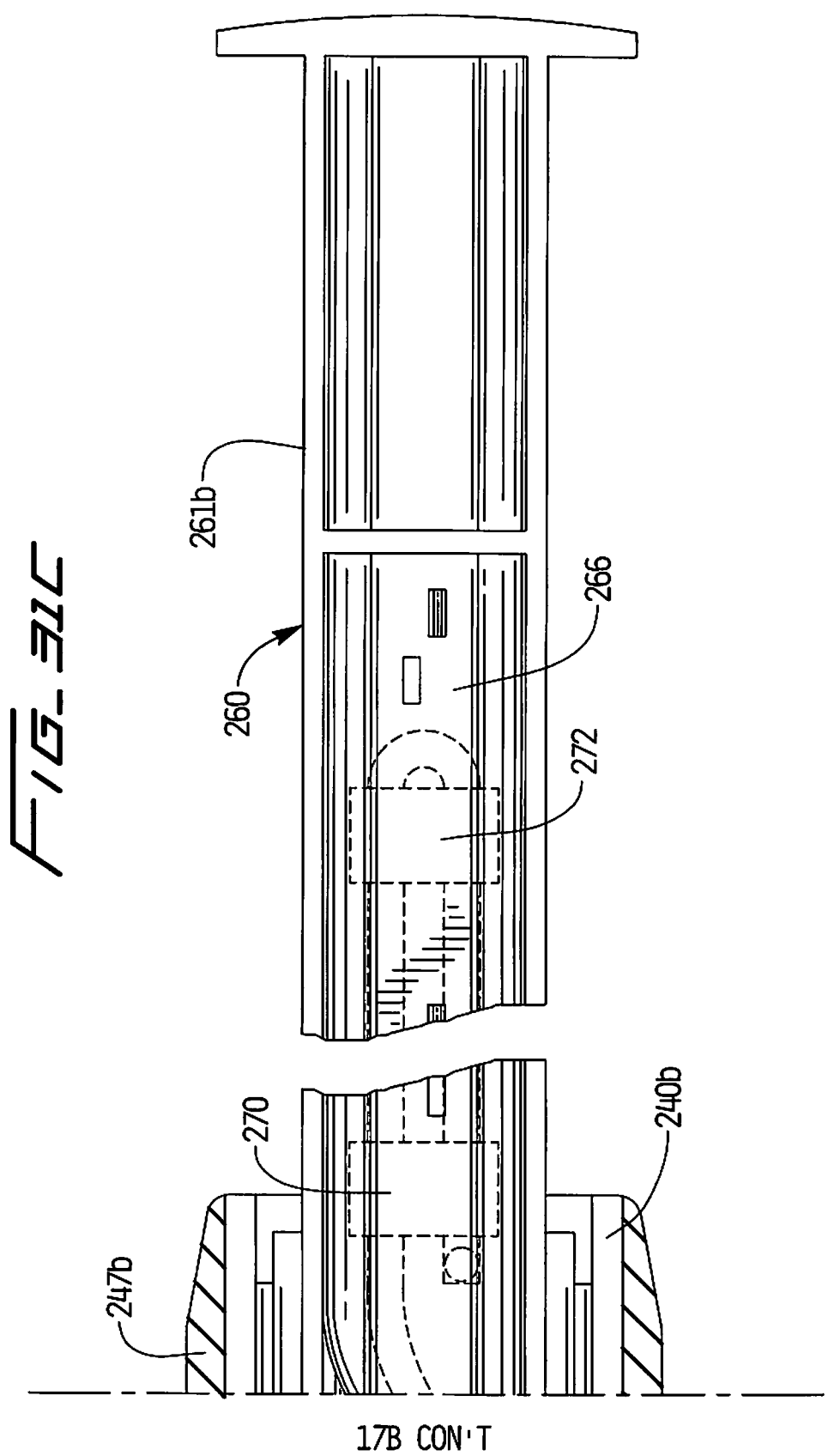

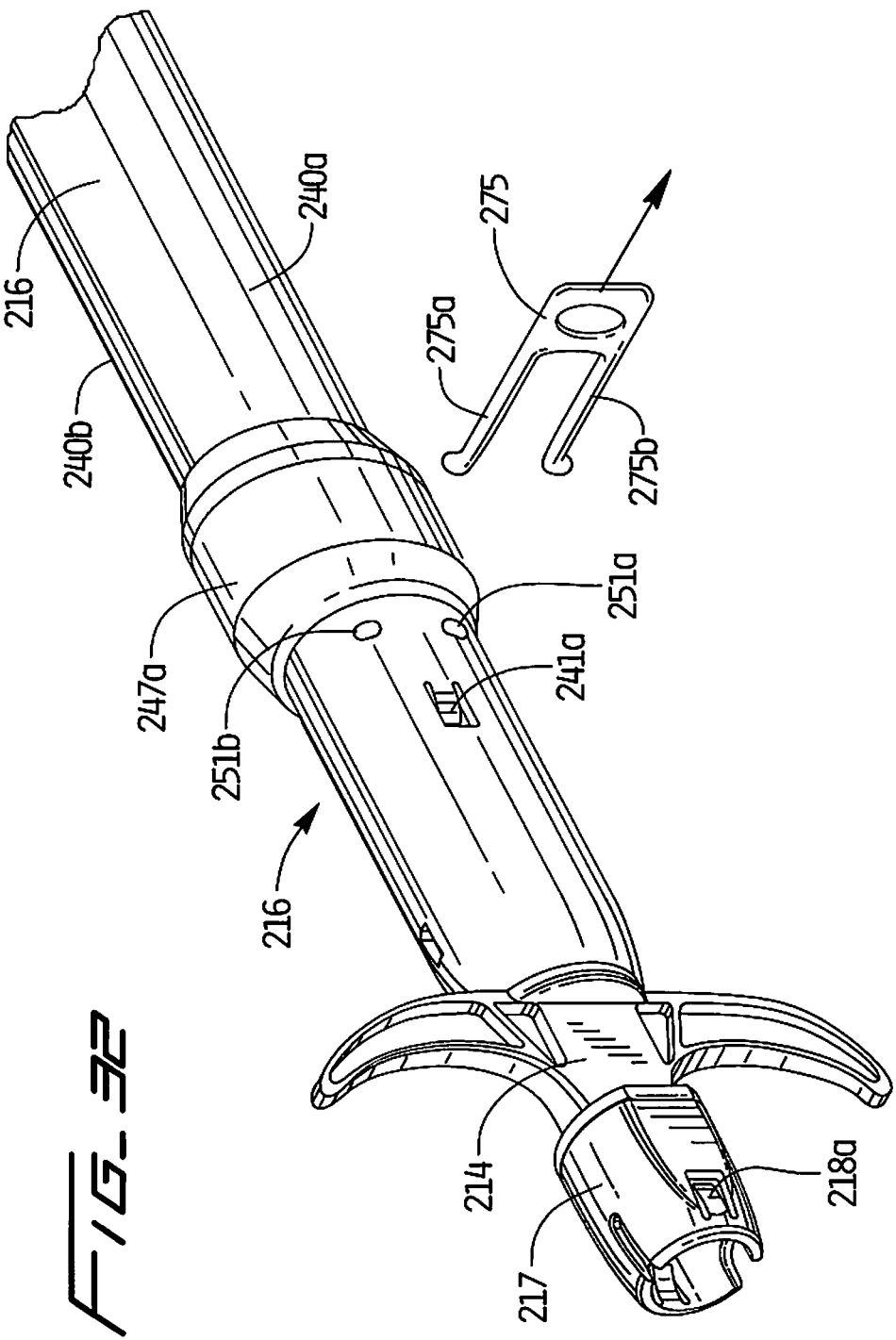

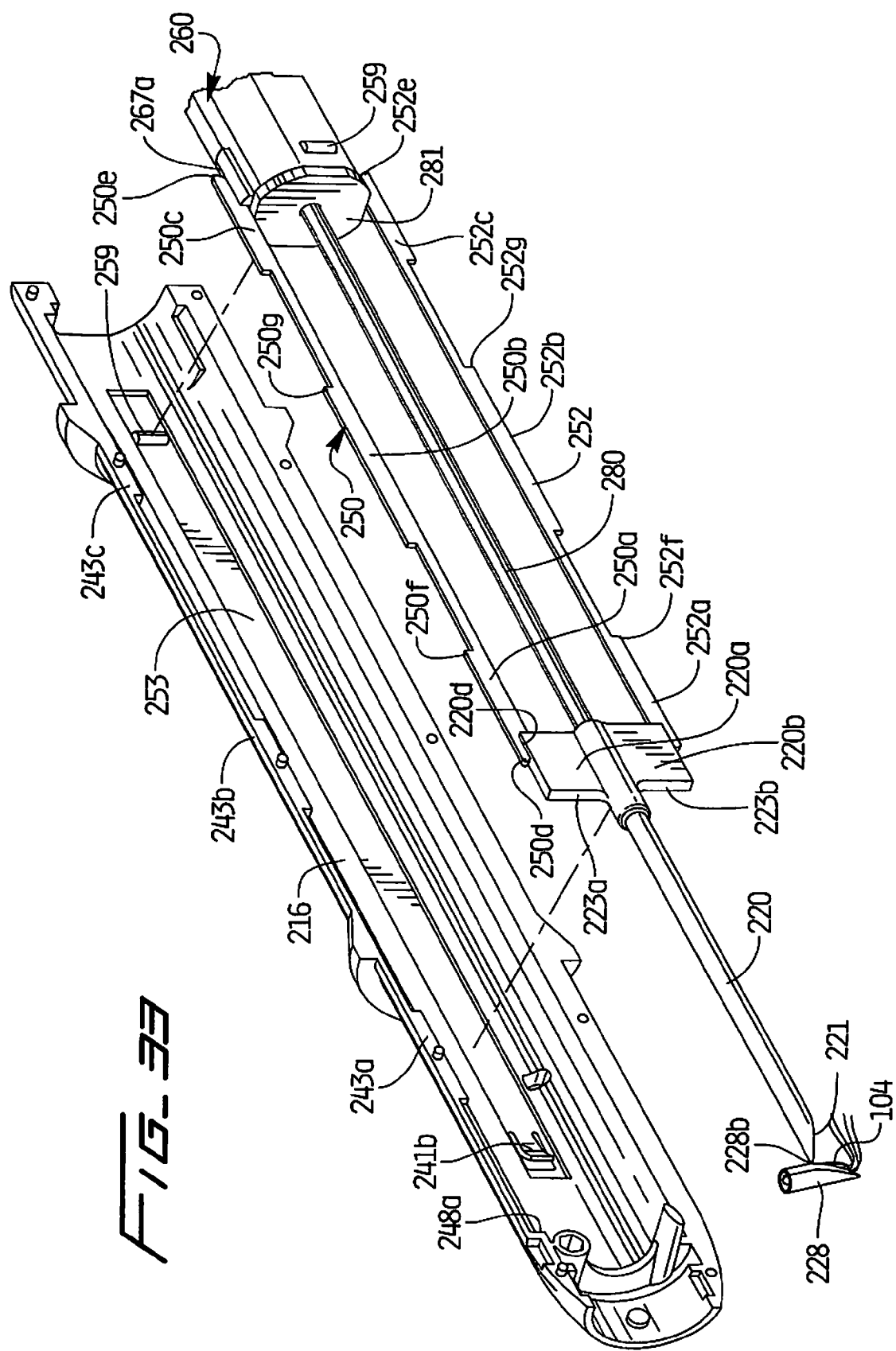

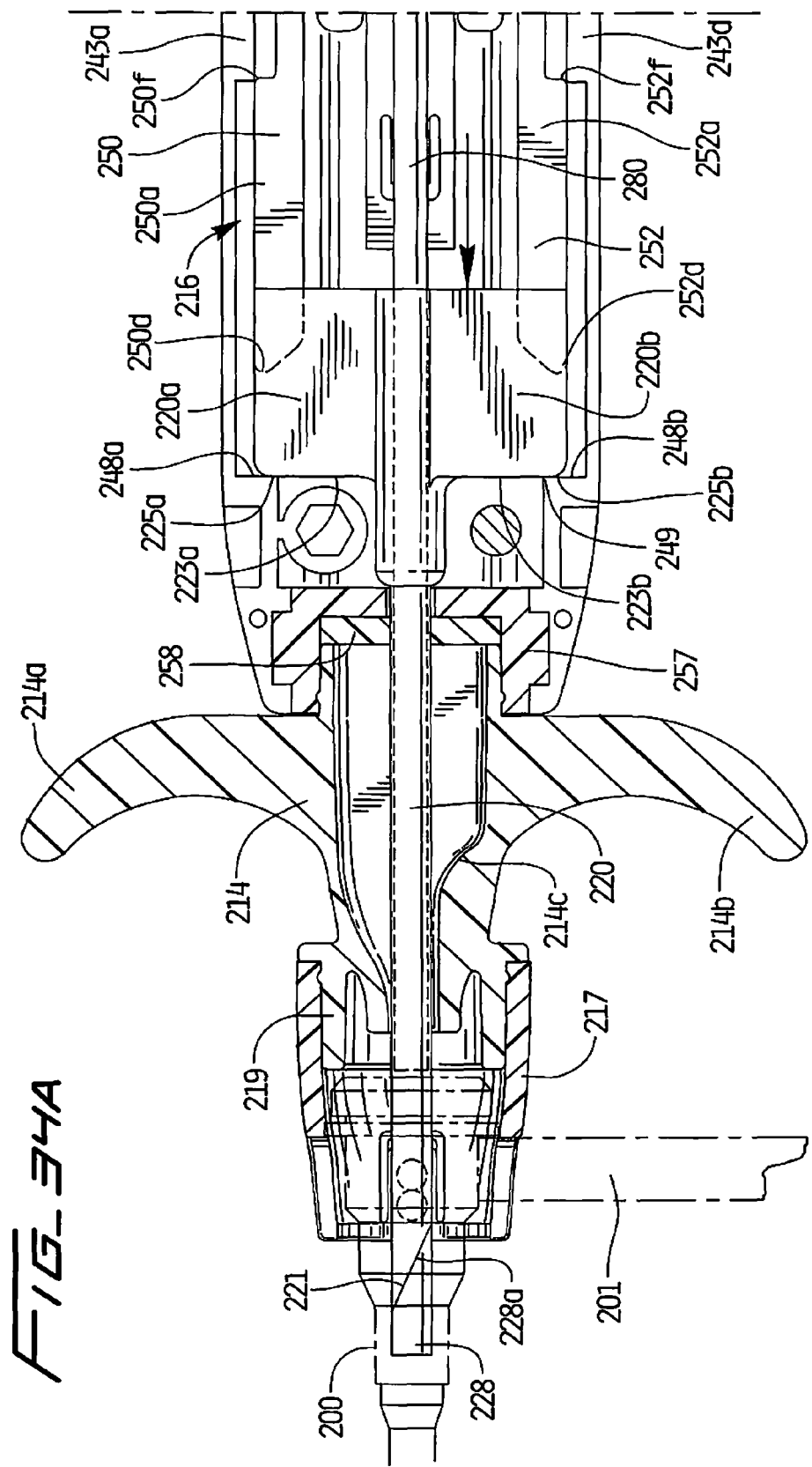

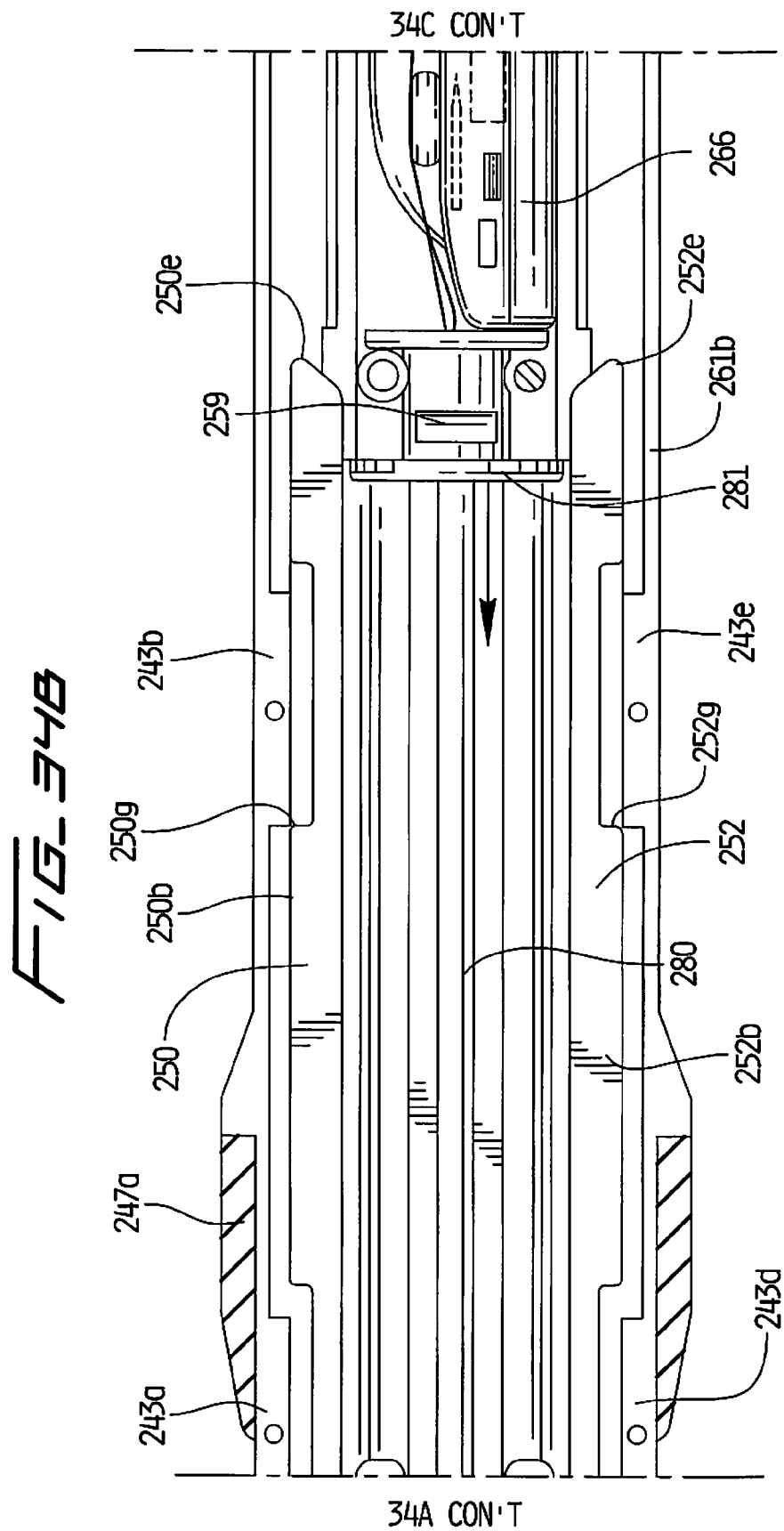

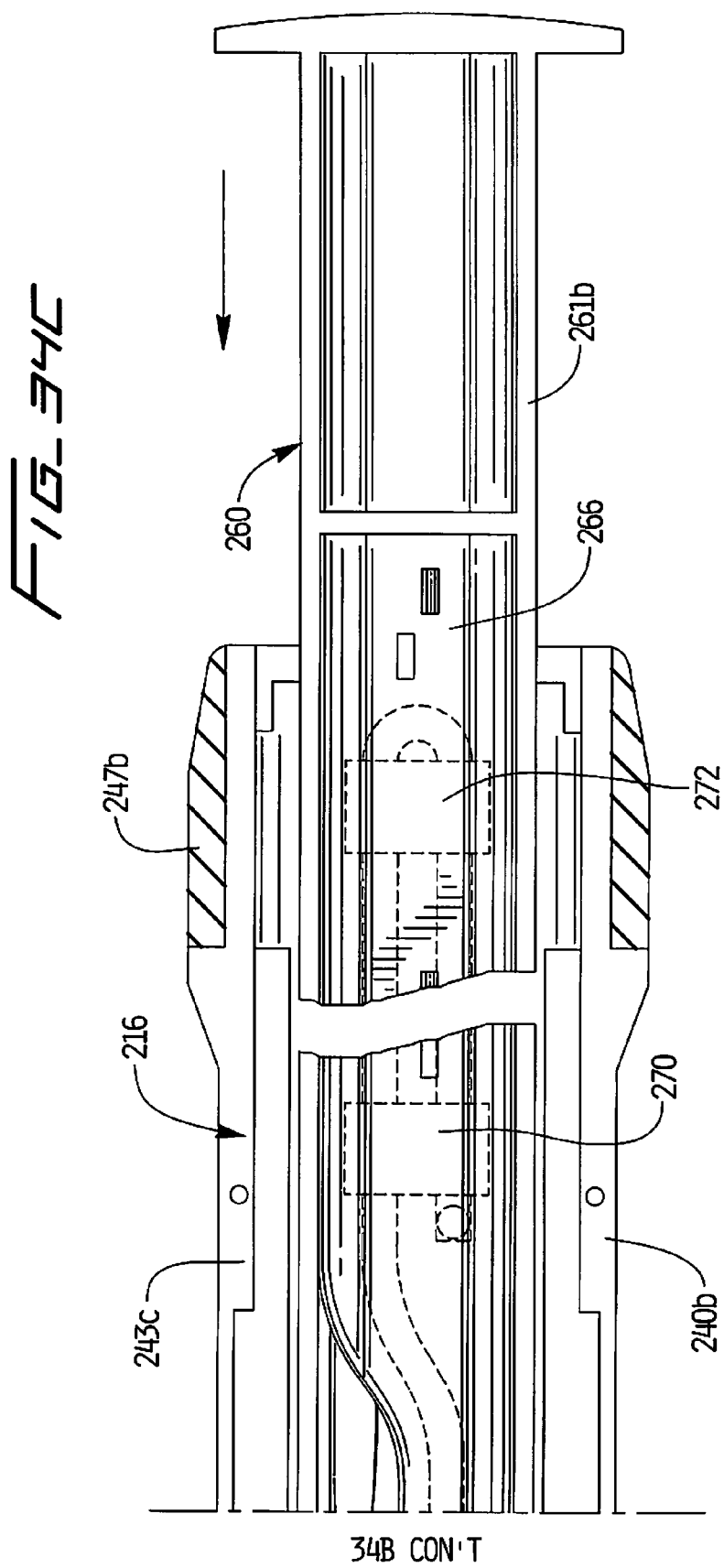

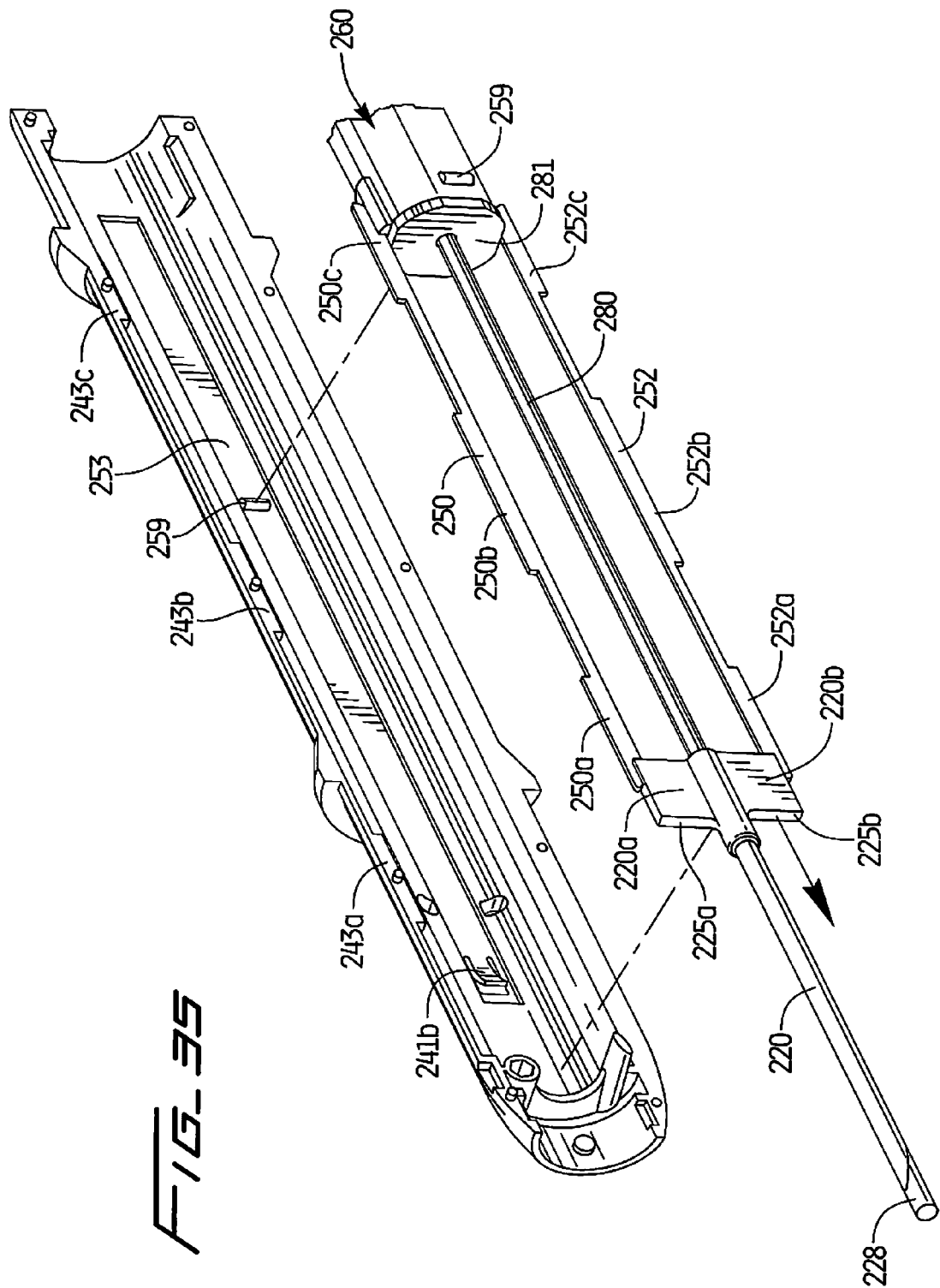

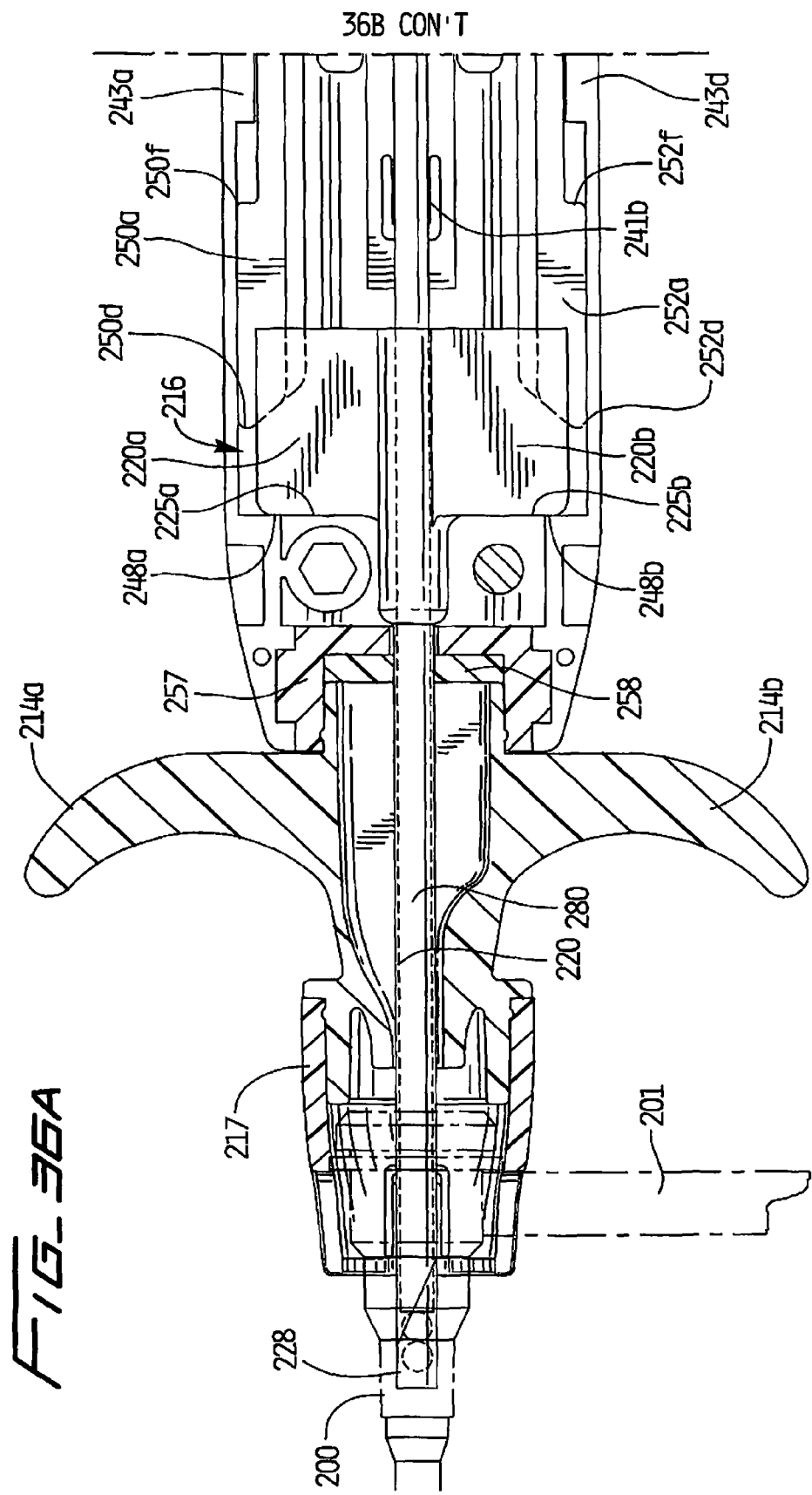

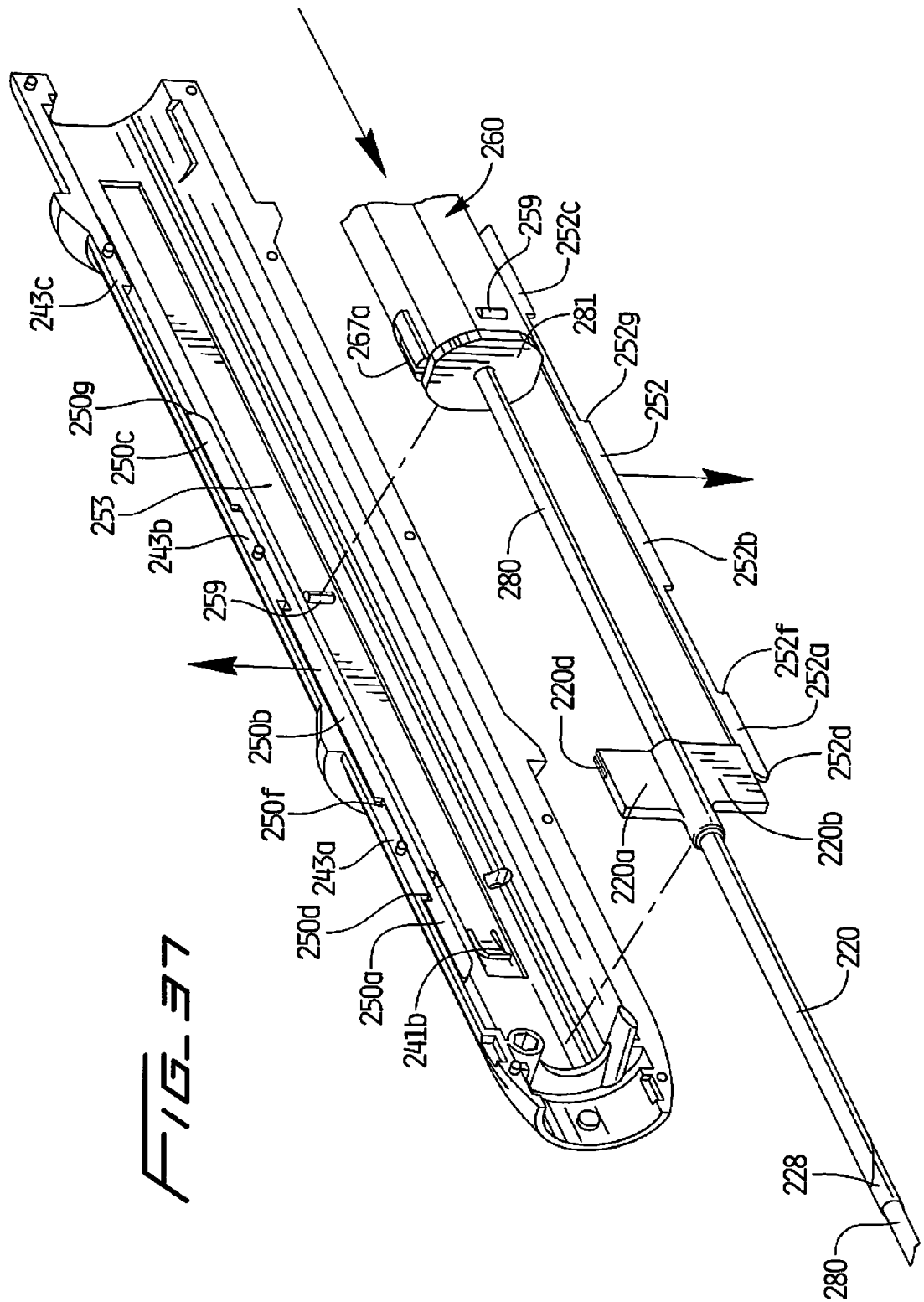

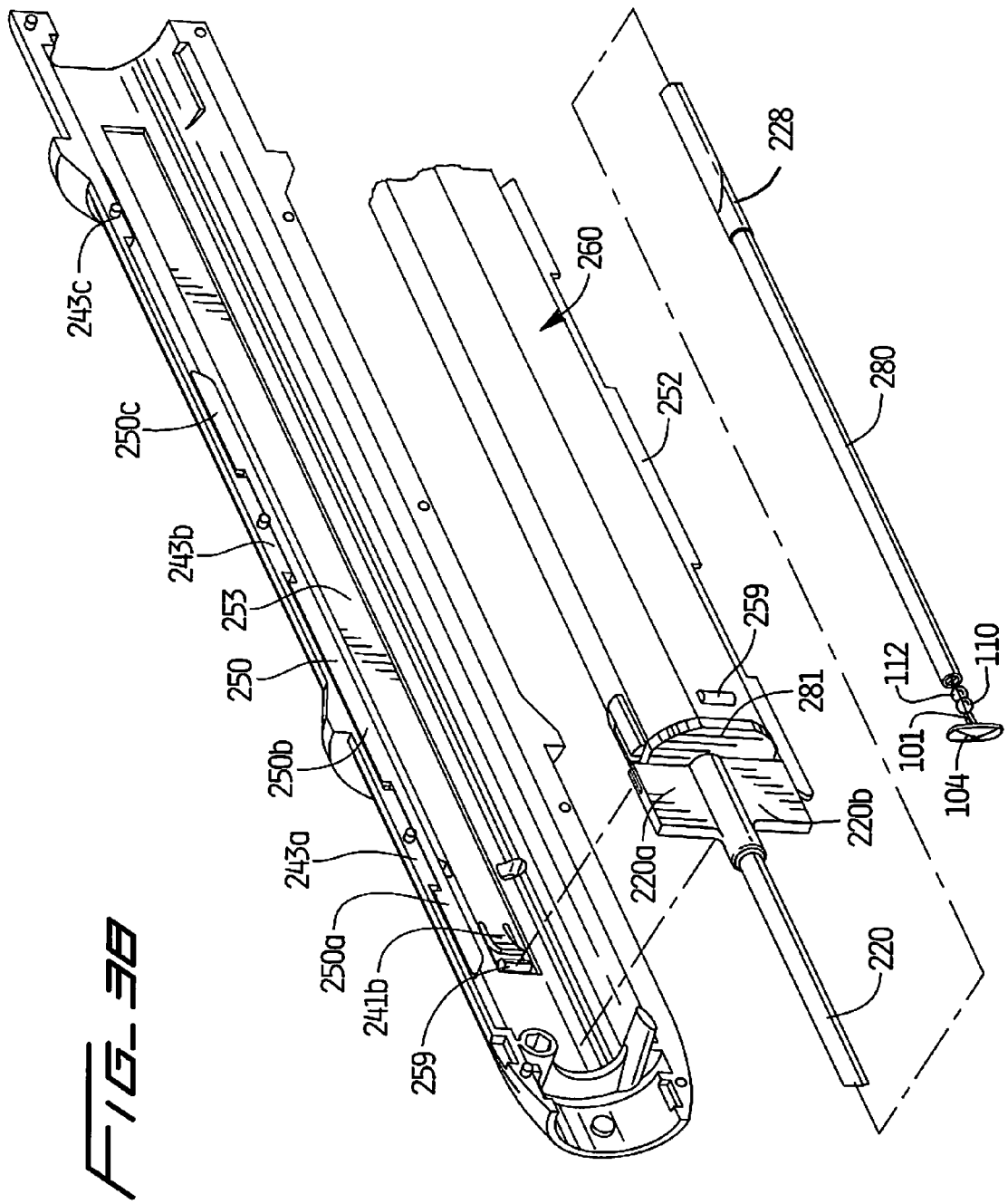

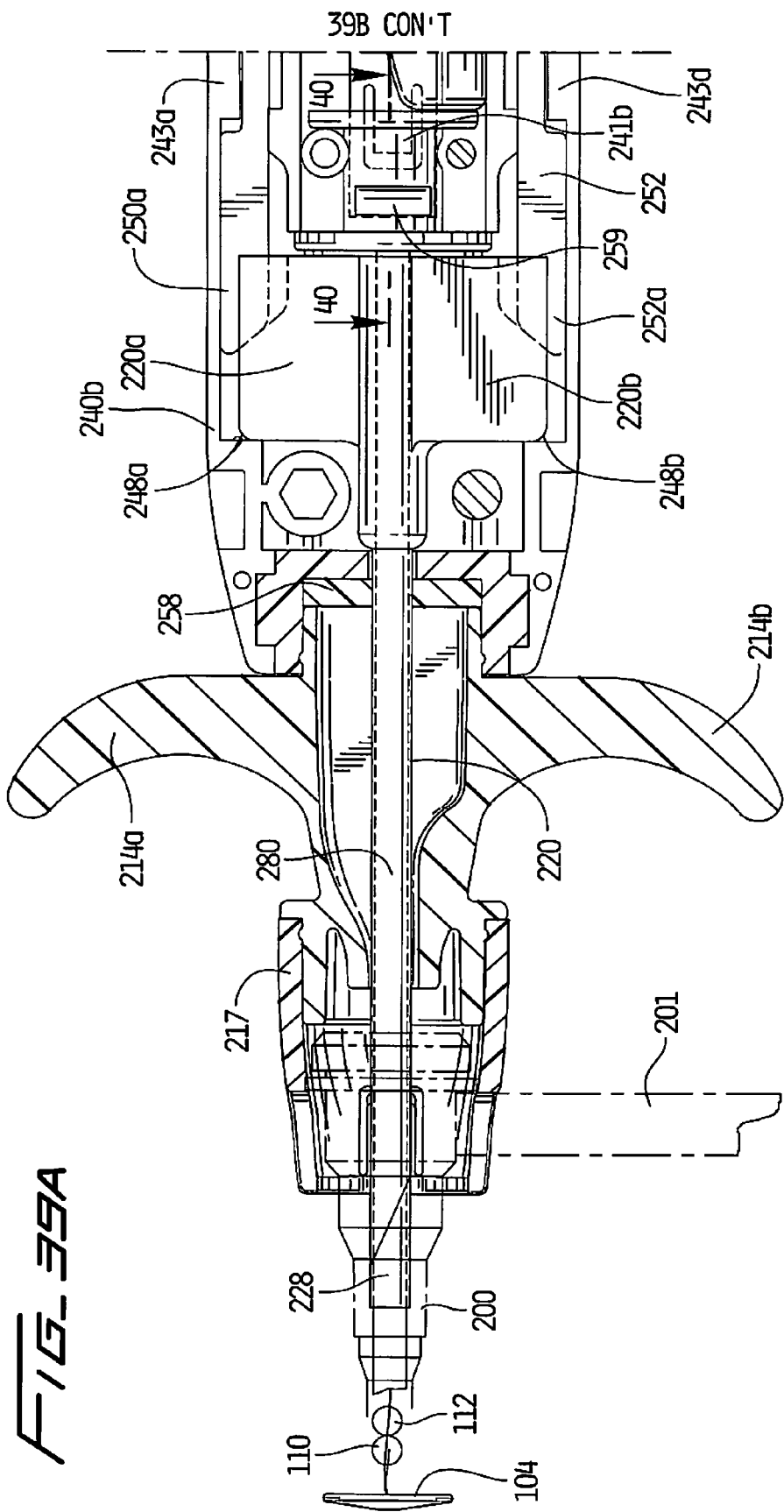

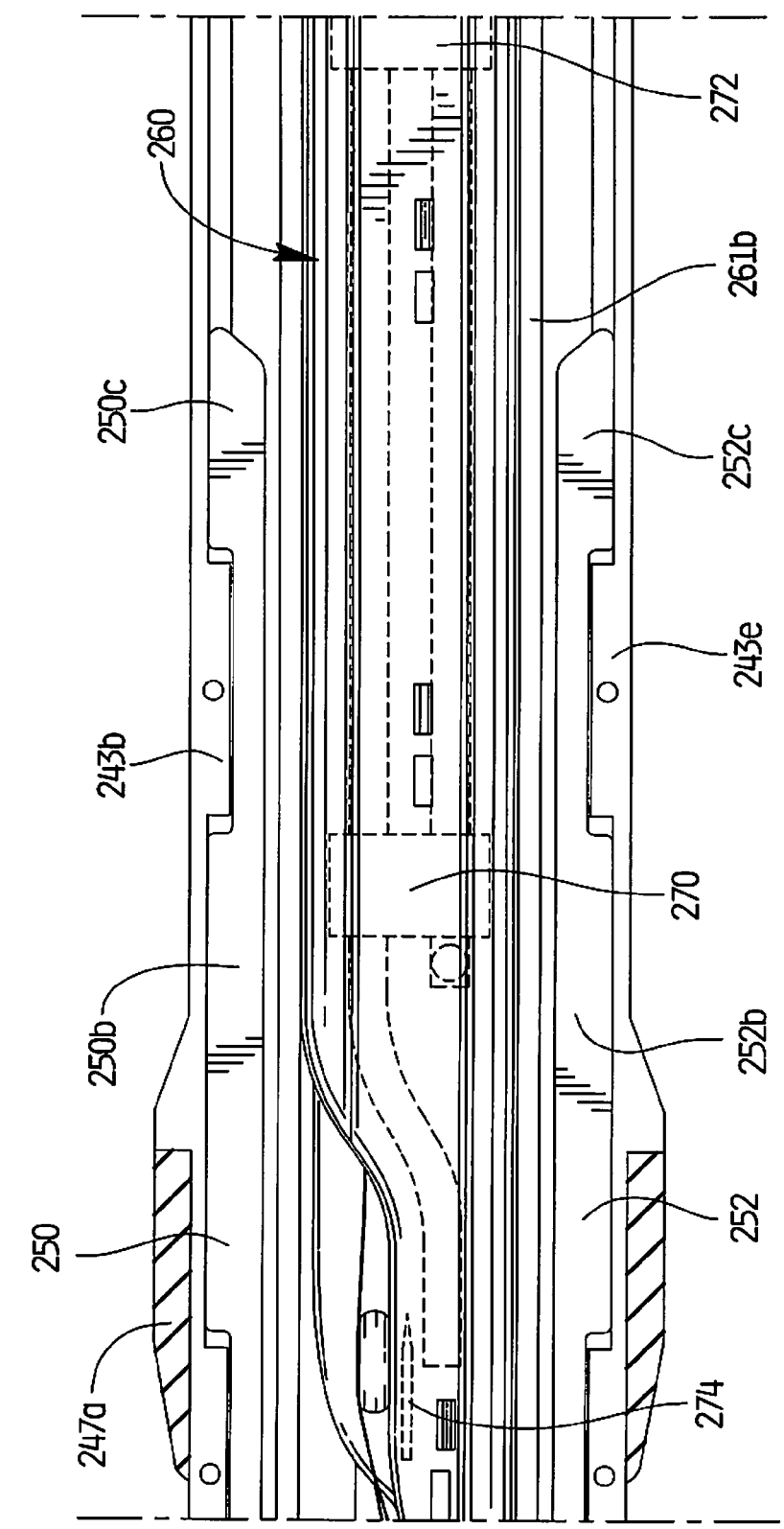

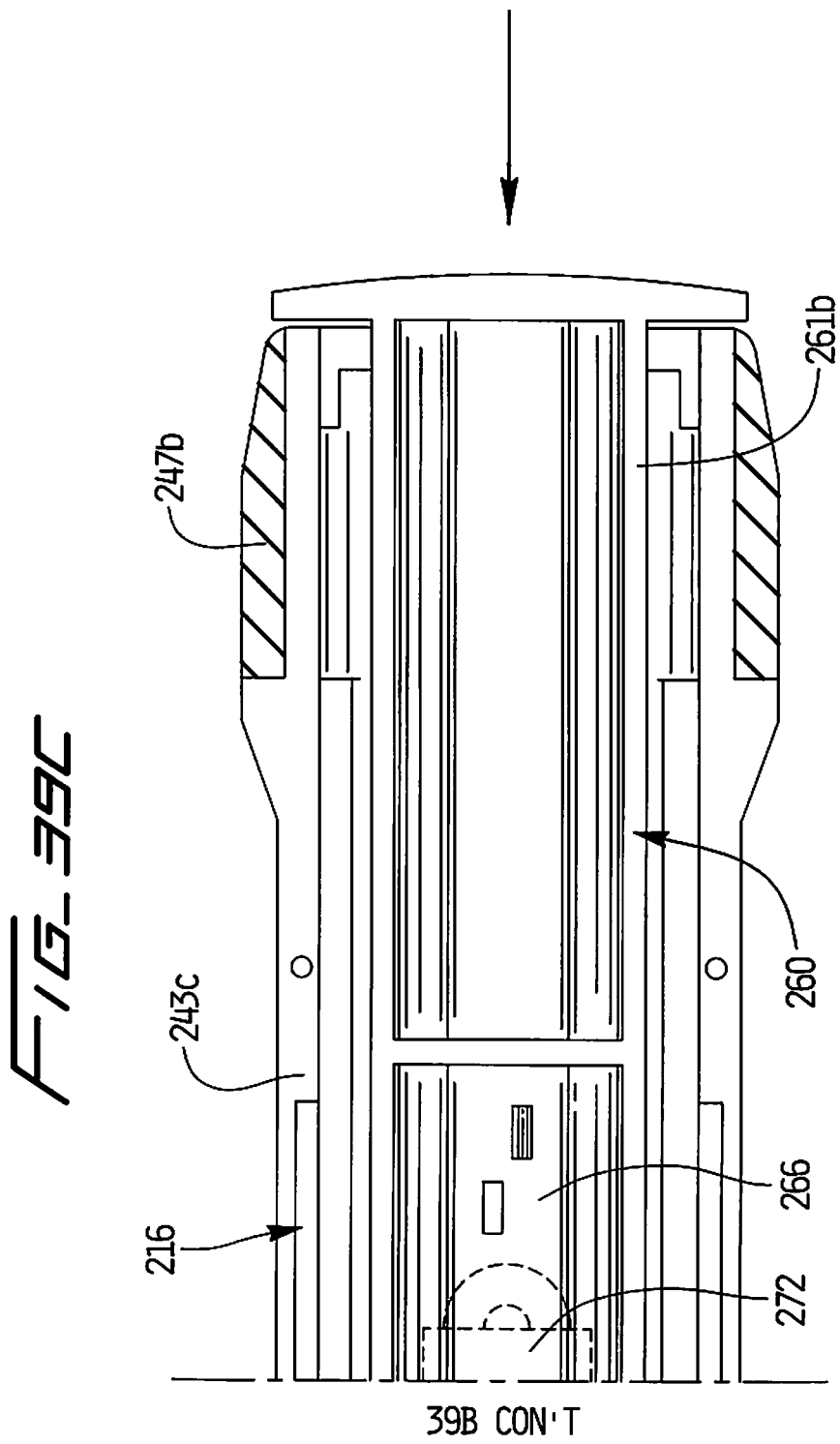

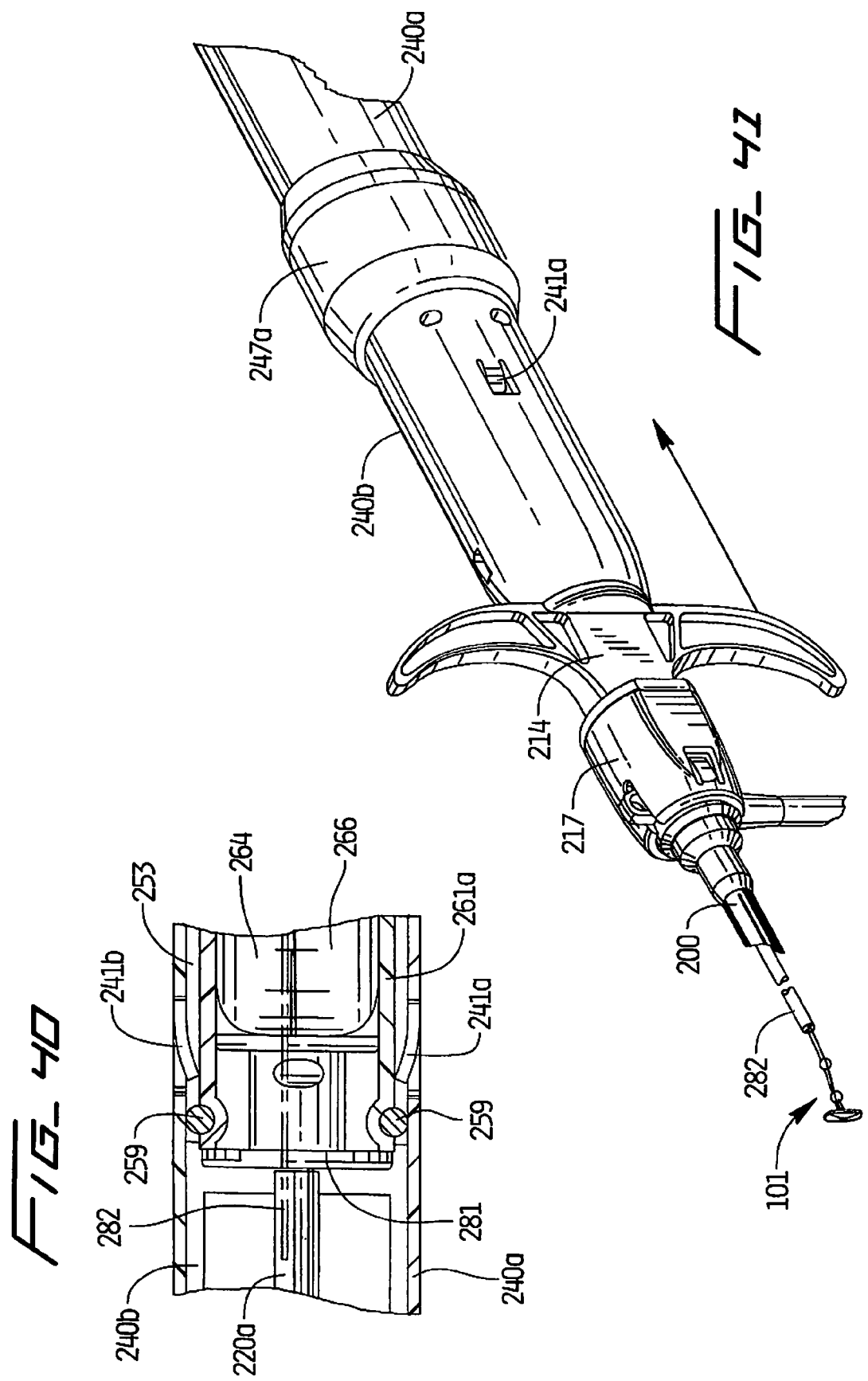

VASCULAR HOLE CLOSURE DELIVERY DEVICE

This application claims priority from provisional application Ser. No. 61/509,829, filed Jul. 20, 2011 and is a continuation in part of application Ser. No. 13/274,402, filed Oct. 17, 2011 now U.S. Pat No. 8,491,629, which claims priority from provisional application 61/409,599, filed Nov. 3, 2010 and is a continuation in part of application Ser. No. 12/854,988, filed Aug. 12, 2010, now abandoned which claims priority from provisional application No. 61/241,555, filed Sep. 11, 2009 and is a continuation in part of application Ser. No. 12/358,411, filed Jan. 23, 2009, now U.S. Pat. No. 8,070,772 which claims priority from provisional application Ser. No. 61/066,072, filed Feb. 15, 2008. The entire contents of each of these applications are incorporated herein by reference.

BACKGROUND

1. Technical Field

This application relates to a delivery device for a vascular device and more particularly to a delivery device for a vascular hole closure device.

2. Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, sold by Abbott, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned U.S. Pat. No. 7,662,161 discloses effective vascular hole closure devices which have the foregoing advantages. It would be further advantageous to provide a vascular hole closure device which is adjustable to accommodate different tissue thicknesses and applies a more constant clamping/retaining force between the intravascular and extravascular components of the device irrespective of tissue thickness. Such adjustability is achieved in copending commonly assigned application Ser. No. 12/854,988, filed Aug. 12, 2010, (hereinafter the '988 application), the entire contents of which are incorporated herein by reference.

The need exists for an effective delivery instrument to deliver the closure device of the '988 application to the target site to close the vascular access hole.

SUMMARY

The present disclosure in one aspect provides a surgical delivery instrument for delivering a vascular hole closure device having a hole covering member. The delivery instrument comprises a housing, a plunger and an advancer movable within the housing. The advancer has a first portion and a distal portion hingedly connected to the first portion and forming a casing for supporting the hole covering member, wherein distal movement of the advancer pivots the casing from an angled position to a more linear position to change the orientation of the covering member from an angled position to a more aligned position. The plunger is advanceable to advance the hole covering member into the vessel.

In some embodiments, the hole closure device includes first and second flexible members, the first flexible member having a first engagement member and the second flexible member having a second engagement member, wherein the plunger has first and second longitudinally extending openings and first and second engaging portions. In these embodiments, the first engaging portion limits movement of the first engagement member and the second engaging portion limits movement of the second engagement member, wherein the first engagement member is held by the first engaging portion until a predetermined force is applied to the first engagement member during placement of the closure device at a target site and the second engagement member is held by the second engaging portion until a predetermined force is applied to the second engagement member during placement of the closure device at the target site. In some embodiments, the first engaging portion comprises a first opening in a first grommet aligned with the first longitudinally extending opening in the plunger and the second engaging portion comprises a second opening in a second grommet aligned with the second longitudinally extending opening in the plunger.

The housing can include an angled inner surface engagable by the casing to pivot the casing to the more linear position.

In some embodiments, the plunger includes a tube and a handle portion positioned proximally of the tube, and movement of the handle portion distally advances the tube within a lumen of the advancer. The instrument can include a distal stop to limit distal movement of the advancer.

In some embodiments, the instrument includes a first actuator for moving the advancer distally which is movable independently of the plunger. In other embodiments, initial advancement of the plunger moves the advancer distally and subsequent advancement of the plunger advances the covering member into the vessel.

In accordance with another aspect of the present disclosure, a surgical delivery instrument is provided for delivering a vascular hole closure device having a hole covering member. The delivery instrument comprises a housing, an advancer movable within the housing, and a plunger. The advancer is movable to change the position of the covering member within the housing and the plunger is subsequently movable to advance the covering member from the housing into the vessel.

In some embodiments, movement of the plunger moves the advancer to change the position of the covering member. In other embodiments, a first actuator is provided for moving the advancer which is movable independently of the plunger.

The instrument can include a stop to limit movement of the advancer, wherein the plunger can be movable within the advancer when the advancer comes into contact with the stop.

In some embodiments, first and second rails operatively connect the advancer and the plunger. The first and second rails can be operatively dissociated from the plunger when the advancer is movable to a distal position into contact with the stop.

In accordance with another aspect of the present disclosure, a surgical delivery instrument is provided for delivering a vascular hole closure device having a first flexible member having a first engagement member extending therefrom and a second flexible member having a second engagement member extending therefrom. The delivery instrument comprises a housing having first and second longitudinally extending lumens and first and second members, the first member having a first opening aligned with the first lumen and the second member having a second opening aligned with the second lumen. The first engagement member passes through the first opening when a predetermined proximal force is applied and the second engagement member passes through the second opening when a predetermined proximal force is applied, wherein the first engagement member is held by the first member until the predetermined proximal force is applied to the first engagement member during placement of the closure device at a target site.

Preferably, the second engagement member is held by the second member until the predetermined proximal force is applied to the second engagement member during placement of the closure device at the target site.

In some embodiments, the first and second flexible members of the closure device are sutures, and the delivery instrument further includes a cutting member positioned within the housing for automatically severing the sutures.

In some embodiments, the first member has a third opening and the second member has a fourth opening, wherein the first engagement member is passable through the first opening when a first force is applied and subsequently passable through the third opening when a subsequent third force is applied. The second engagement member can be passable through the second opening when a second force is applied and subsequently passable through the fourth opening when a subsequent fourth force is applied. These forces in some embodiments may vary. The first and third forces can be substantially equal or substantially different. The second and fourth forces can be substantially equal or substantially different.

In some embodiments, the vascular hole closure device has a covering member at a distal end for positioning internal of a vessel and a first and second retainer for positioning external of the vessel, wherein the first flexible member extends between the covering member and the first retainer and the first engagement member is positioned at a proximal portion of the first flexible member, and the second flexible member extends between the covering member and the second retainer and the second engagement member can be positioned at a proximal portion of the second flexible member, wherein proximal movement of the delivery instrument advances the first retainer and the second retainer toward the covering member.

A method for delivering a vascular hole device using the aforedescribed instruments are also provided.

BRIEF DESCRIPTION OF THE DRAWINGS

Preferred embodiment(s) of the present disclosure are described herein with reference to the drawings wherein:

FIG. 1 is a perspective view of a first embodiment of the hole closure delivery instrument of the present disclosure;

FIG. 2 is an exploded view of the advancer portion of the delivery instrument of FIG. 1;

FIG. 2A is an exploded view of the handle (plunger) portion of the delivery instrument of FIG. 1;

FIG. 2B is an enlarged view of the area of detail of FIG. 2;

FIG. 3 is a longitudinal cross-sectional view taken along line 3-3 of FIG. 1 showing the advancer in the initial position;

FIG. 3A is a longitudinal cross-sectional view taken along line 3A-3A of FIG. 1 showing the handle portion in the initial position;

FIG. 3B is an enlarged view of the area of detail of FIG. 3;

FIG. 4 is a transverse cross-sectional view taken along line 4-4 of FIG. 3;

FIG. 5 is a transverse a cross-sectional view taken along line 5-5 of FIG. 3;

FIG. 6 is a transverse cross-sectional view taken along line 6-6 of FIG. 3A;

FIG. 7 is a perspective view of the advancer portion illustrating initial movement of the sliding tab;

FIG. 8 is a view similar to FIG. 3B showing initial movement of the sliding tab;

FIG. 8A is a longitudinal cross-sectional view similar to FIG. 3 showing initial movement of the sliding tab to advance the advancer tube and corresponding to the position of FIG. 7, and further showing the sheath connected to the instrument;

FIG. 8B illustrates the sliding tab adjacent the lockout;

FIG. 8C illustrates the sliding tab advanced past the lockout;

FIG. 9 is a perspective view similar to FIG. 7 showing the sliding tab in the distal position to fully advance the advancer tube;

FIG. 10 is a longitudinal cross-sectional view similar to FIG. 8A showing the sliding tab in the distal position to fully advance the advancer tube and corresponding to the position of FIG. 9;

FIG. 11 is a perspective view similar to FIG. 9 illustrating the sliding tab in the distal position and the handle portion advanced to the distal position to deploy the hole closure device in the vessel;

FIG. 12 is an enlarged view of the area of detail of FIG. 11;

FIG. 13 is a longitudinal cross-sectional view similar to FIG. 10 showing the sliding tab in the distal position and the handle portion advanced to the distal position, corresponding to the position of FIG. 11;

FIG. 14 is a perspective view illustrating initial retraction of the delivery instrument to further deploy the hole closure;

FIG. 15 is an exploded view of a portion of the handle portion (plunger) showing a first housing half section with initial movement of the second engagement member and the first engagement member engaged with the lower opening of the distal blocking element in the central housing;

FIG. 17 is an exploded view of a portion of the handle portion showing the first housing half section with further movement of the first engagement member in the lower channel of the central housing and the second engagement member engaged with the proximal blocking element in the lower channel of the first housing;

FIG. 18 is a longitudinal cross-sectional view of the handle portion of the delivery instrument corresponding to the position of FIG. 17 illustrating further proximal movement of the handle portion of the delivery instrument to advance the second retainer of the closure device toward the covering member;

FIG. 19 is a view similar to FIG. 15 illustrating the first engagement member in the curved channel of the central housing and the second engagement member engaged with the proximal blocking member at the upper opening;

FIG. 20 is a cross-sectional view of the proximal end of the handle portion of the delivery instrument corresponding to the position of FIG. 19 and showing further advancement of the second retainer of the closure device toward the covering member;

FIG. 21 is a view similar to FIG. 19 illustrating the first engagement member engaging an upper opening in the distal blocking member and the second engagement member in the upper channel of the central housing;

FIG. 22 is a cross-sectional view of the proximal end of the handle portion of the delivery instrument corresponding to the position of FIG. 21 and showing further proximal movement of the handle portion of the delivery instrument to further advance the first retainer of the closure device toward the covering member;

FIG. 23 is a perspective view of a region of the handle portion showing the sutures adjacent the cutting blade;

FIG. 24 is a cross-sectional view corresponding to the position of the second suture in FIG. 23;

FIG. 25 is a perspective view similar to FIG. 23 showing the sutures engaged with the cutting blade;

FIG. 26 is a cross-sectional view similar to FIG. 24 corresponding to the position of the second suture in FIG. 25;

FIG. 27 is a perspective view of a hole closure delivery instrument in accordance with an alternate embodiment of the present disclosure;

FIG. 28 is a cross-sectional view taken along line 28-28 of FIG. 27;

FIG. 29 is a front view of the delivery instrument of FIG. 27;

FIG. 30A is an exploded view of the advancer portion of the delivery instrument of FIG. 27;

FIG. 30B is an exploded view of the handle portion (plunger) of the delivery instrument of FIG. 27;

FIGS. 31A, 31B and 31C are longitudinal cross-sectional views taken along lines 31A-31A, 31B-31B and 31C-31C of FIG. 27 showing the delivery instrument (handle portion and advancer) in the initial position;

FIG. 32 is a perspective view of a section of the delivery instrument of FIG. 27 showing removal of the locking tab;

FIG. 33 is a partially exploded view of the advancer portion with the advancer in the initial position (only one of the housing halves is shown);

FIGS. 34A, 34B and 34C are longitudinal cross-sectional views similar to FIG. 31A, 31B, 31C showing initial distal movement of the handle portion (plunger) to move the advancer to the distal position to align the casing for the hole closure device and advance it into the sheath;

FIG. 35 is a partially exploded view similar to FIG. 33 corresponding to the position of the handle portion and advancer of FIGS. 34A-34C;

FIGS. 36A and 36B are longitudinal cross-sectional views similar to FIGS. 34A and 34B showing further distal movement of the handle portion to move the rails into the spaces in the housing;

FIG. 37 is a partially exploded view similar to FIG. 35 corresponding to the position of the handle portion and the advancer of FIGS. 36A and 36B;

FIG. 38 is a partially exploded view similar to FIG. 37 showing the handle portion fully advanced to the distal position;

FIGS. 39A, 39B and 39C are longitudinal cross-sectional views similar to FIGS. 34A, 34B and 34C showing full advancement of the handle portion to the distal position;

FIG. 40 is a cross-sectional view taken along line 40-40 of FIG. 39A; and

FIG. 41 is a perspective view showing retraction of the delivery instrument after full advancement of the handle portion to further deploy the hole closure device.

DETAILED DESCRIPTION OF PREFERRED EMBODIMENTS

Figure 16:
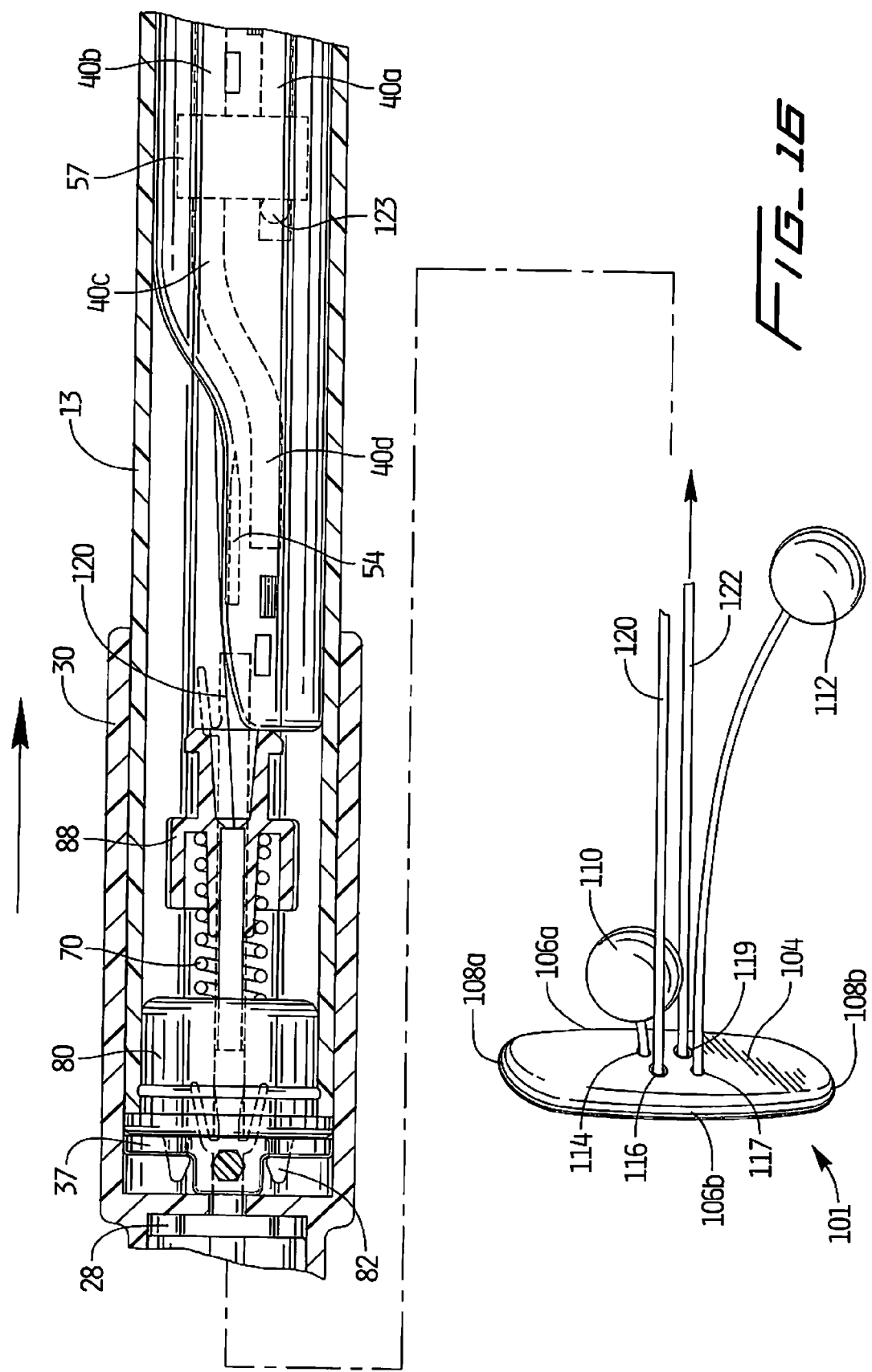
FIG. 16 is a longitudinal cross-sectional view of the handle portion of the delivery instrument corresponding to the position of FIG. 15 illustrating proximal movement of the handle portion of the delivery instrument to advance the first retainer of the closure device toward the covering member.

Referring now in detail to the drawings wherein like reference numerals identify similar or like components throughout the several views, the present application is directed to a delivery instrument for delivering a vascular hole (aperture) closure device. The closure device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure device of the present disclosure has an intravascular component to block blood flow and an extravascular component to retain the intravascular component.

The hole closure device 101 is illustrated in FIGS. 12, 16, 18, 20 and 22 in various stages of delivery and is described in more detail in patent application Ser. No. 12/854,988, filed Aug. 12, 2010, (hereinafter the '988 application), the entire contents of which are incorporated herein by reference. The closure device includes a covering member or patch 104 positioned within the vessel against the internal wall of the vessel to block blood flow through the vessel aperture and two retainers 110, 112 positioned external of the vessel wall to retain the covering member 104 in its blocking position. Each retainer 110, 112 is preferably spherical in configuration and is fixedly attached to a respective suture 122, 120, such that pulling of the respective suture advances the attached retainer toward the covering member 104 to ultimately position the retainers 110, 112 in a side by side relationship either against or adjacent the external surface of the vessel wall.

Covering member 104, preferably elongated in configuration as shown, is retained in a delivery sheath in a longitudinal position for delivery to the vessel, and then pivots to a transverse position within the vessel lumen (substantially perpendicular to an axis extending through the aperture) for orientation to cover (patch) the vessel aperture on the internal side. This movement is illustrated in FIGS. 37A-37D of U.S. Pat. No. 7,662,161, the entire contents of which are incorporated herein by reference (hereinafter the '161 patent).

The elongated covering member 104 functions to cover (patch) the internal opening in the vessel wall to prevent the egress of blood. The covering member 104 is preferably somewhat oval shaped with elongated substantially parallel side walls 106a, 106b, and end walls 108, 108b connecting the side walls 106a, 106b. Other shapes of the covering member are also contemplated. The end walls 106a, 106b can have substantially straight wall portions, or curved wall portions. Covering member 104 preferably has a thicker region in the central region than the first and second end regions. Other dimensions and configurations are also contemplated.

The longitudinal axis of covering member 104 defines a lengthwise dimension and transverse axes define a shorter widthwise dimensions. The widthwise dimension of the covering member 104 is preferably, for a 6 Fr device, in the range of about 2.5 mm to about 3.5 mm, and more preferably about 3.1 mm. Other dimensions are also contemplated. The width preferably is at least substantially equal to the dimension of the internal opening in the vessel wall to effectively cover the opening. In a preferred embodiment, the covering member 104 has a length in the range of about 7.5 mm to about 9 mm (in a 6 French system), and preferably about 8 mm.

It should be appreciated that alternatively the covering member could be provided with an enlarged width region as illustrated in the embodiment of FIG. 1 of the '161 patent. The covering member could also be configured asymmetrically so that the enlarged region is off-centered to accommodate widening of the aperture as the member is pulled at an angle. The covering member could also be configured in a paddle shaped with a narrowed region adjacent a wider region as in FIGS. 9B-9E of the '161 patent. Other covering member configurations including those disclosed in the '161 patent could be utilized with the retainers of this present application.

The elongated covering member can be composed of materials such as polycarbonate or polyurethane. Preferably it is composed of resorbable materials such as lactide/glycolide copolymers that after a period of time resorb in the body. If composed of resorbable material, the covering member could optionally have regions of varying resorbability. Varying degrees of resorbability can be achieved for example by utilizing different materials having differing resorbable characteristics or by varying the mass of the covering member (increased mass increases resorbtion time).

Spherical retainers 110, 112 are preferably composed of resorbable material. In a preferred embodiment, the diameter of each retainer 110, 112 is about 0.090 inches to about 0.095 inches, although other dimensions are contemplated. Although shown as spheres, other shapes including other rounded shapes are also contemplated. The retainers could alternatively be made of non-absorbable polymeric or metallic material.

When the retainers 110, 112 are released from the delivery instrument, they are spaced further from the covering member 104. They are then configured to be advanced toward the covering member 104. More specifically, each retainer 110, 112 is fixedly secured to a respective flexible connecting member such as suture 122, 120. Sutures 122, 120 are preferably made of polymeric material and are preferably resorbable, composed of a material such as polydioxanome. It is also contemplated that alternatively a metallic material could be utilized. The sutures, retainers and covering member can be made of the same or different resorbable material, and/or have the same or different resorption times.

Details of the hole closure device as well as various embodiments of the device are shown and described in the '988 patent application previously incorporated by reference herein.

Suture 120 has a second end 120a (FIG. 2A) and a first opposite end secured to retainer 112 by molding, gluing, forming a knot, or other methods. Similarly, suture 122 has a second end 122a and a first opposite end secured to retainer 110 in any of the foregoing manners. Various methods of attachment are shown in the '988 application.

To advance the retainers 110, 112 toward the vessel wall (and covering member), the ends 122a, 120a of each suture 122, 120 is pulled proximally, thereby moving the respective retainer in the opposite direction closer to the aperture and vessel wall. This is described in detail below in conjunction with the delivery instrument. Note that once the retainers 110, 112 are tightened against the tissue, a sufficient retention force is maintained, i.e. a proximal pulling force on the covering member 104 to pull it slightly proximally against the vessel wall. The retainers 110, 112 therefore help to prevent the covering member 104 from separating from the vessel wall (e.g. moving in the direction toward the opposing vessel wall) which could create an unwanted gap between the covering member 104 and the vessel opening to allow blood flow. The extent to which the retainers 110, 112 move toward the wall (and thus their distance from the vessel wall in their final placement position) will depend on the tissue thickness. Thus, the closure device can adjust for different tissue thicknesses and apply a constant retention force regardless of tissue thickness.

The covering member 104 as shown in FIG. 16 has a first pair of holes and a second pair of holes. The first pair of holes 116, 117 receive suture 120 and the second pair of holes 119, 114 receive suture 122. Holes 114, 117 have a smaller diameter than holes 116, 119. The larger hole 116 is dimensioned to receive suture 120 for free unrestricted movement of the suture 120 therethrough and therefore easier application of spherical retainer 112. Similarly, the larger hole 119 is dimensioned to receive suture 122 for free unrestricted movement of the suture 122 therethrough and therefore for easier application (movement) of spherical retainer 110. Smaller hole 114 is dimensioned to frictionally engage suture 122 so that tension is applied to the suture 122. It is dimensioned so that the suture 122 can be pulled through the hole 114 if sufficient force is applied by pulling on second end 122a, but if such predetermined force is not applied, the suture will remain frictionally engaged within the wall of the opening 114 and not move. In this manner, when tension on end 122a is terminated, the suture 122 and thus the spherical retaining ball 110 will remain in position. Suture 120 operates in a similar manner, with smaller opening 117 dimensioned to frictionally engage and resist movement of the suture 120 to retain spherical retaining ball 112. Preferably, each hole 114, 117 has an inwardly angled wall transitioning into a reduced diameter region and an outwardly angled wall transitioning back to a larger diameter. The angled walls facilitate movement of the suture when tension is applied, with the reduced diameter region frictionally securing the suture. Hole 117 has a similar configuration as hole 114 and thus also contains similar angled walls. In this manner, when tension on end 120a is terminated, the suture 120 and thus the spherical retaining ball 112 will remain in position.

As shown in FIGS. 16 and 18, retainer 110 is pulled towards the smaller hole 114 and retainer 112 is pulled toward the smaller hole 117. However, it is also contemplated, to facilitate manufacture, that the sutures could be reversed so the retainer 110 is pulled toward the larger hole 116 and the retainer 112 is pulled toward the larger hole 119.

A crimp or a bead can be attached to the suture, or a knot formed in the suture, creating a diameter larger than the diameter of portion within the retainer which forms a shoulder to block movement of the respective spherical retainer 110 or 112. Consequently, this frictional engagement prevents the respective retainer from sliding in the direction away from the covering member 104 while the shoulder prevents the retainer from sliding in the direction toward the covering member 104. The retainer 112 and suture 120 preferably have the same structure and engagement/retention as retainer 110 and suture 122.

Note that during delivery the covering member 104 emerges from the delivery sheath and moves from a tilted position, more aligned or in preferred embodiments substantially aligned with the longitudinal axis of the sheath, to a transverse position within the vessel. This is due to a preset in the sutures which maintains the covering member in the transverse position.

As can be appreciated, covering member 104 is pulled proximally to abut the internal opening on the internal side of the vessel to cover the opening and the sutures extend through the opening in the vessel wall. Note that in the delivery position, the retainers 110 and 112 are preferably in a stacked relationship within the delivery instrument to minimize the transverse dimension of the delivery system.

Then, to retain the covering member 104 in position against the vessel wall to block blood flow therethrough, sutures 120, 122 are pulled proximally from their ends 120a, 122a, thereby advancing the retainers 112, 110 toward the vessel wall and covering member 104. The retainers 112, 110 can be moved to a position contiguous to the vessel wall, or depending on tissue thickness, may be adjacent the wall with some tissue interposed between the retainers and vessel wall. The retainers 110, 112 in this position apply a proximal force on the elongated covering member 104 to limit movement of the covering member into the vessel. The retainers in this placement position are preferably in a substantially side by side relationship. The instrument for delivering these elements to the target site to close the vessel opening is described in detail below.

As shown in FIG. 22, in the side by side relationship, the retainers 110, 112 are alongside in a transverse orientation with respect to covering member 104. That is, they are positioned along the width of the covering member 104 However it is also contemplated that the retainers in the placement position can be in a lengthwise orientation (substantially parallel to the longitudinal axis of the covering member.) The retainers could also be in other side by side arrangements at angles to the longitudinal axis. Alternatively, the retainers can be partially stacked in the placement position.

Turning now to the delivery instrument of the present disclosure and with initial reference to FIGS. 1 and 2, the delivery instrument is designated generally by reference numeral 10 and includes a handle portion or handle housing 12, an elongated outer tube 14 extending distally from the handle portion 12, and an advancer portion 16. Handle portion 12, as shown in FIG. 2A, includes a first housing half 40, a second housing half 42 and a central housing support 44 which together form channels for passage of the sutures. Further details of the handle portion (plunger) 12 are described in detail below.

The delivery instrument 10 for inserting the closure device extends through an opening in the patient's skin, through the underlying tissue, through an external opening in the vessel wall, through the aperture in the vessel wall, and through an internal opening on the internal side of the vessel wall into the vessel lumen.

The delivery instrument 10 deploys the hole closure device 101 in a multiple step process. In the first step, the advancer portion 16 reorients the hole closure device 101 and advances the hole closure device from the delivery instrument 10, and into a proximal end of a sheath (FIG. 10). In the second step, the handle portion 12 is advanced with respect to the advancer portion 16 to advance the hole closure device 101 through the sheath 200 and into the vessel lumen of a patient. In the third step, the entire delivery instrument 10 is retracted proximally to move the retainers 110, 112 toward the covering member 104. This multiple step process is described in detail below.

Turning first to the advancer portion 16 of the delivery instrument, and with initial reference to FIGS. 2 and 3, advancer portion 16 includes a winged housing 22, a guide housing 30 and an advancer tube 39. Advancer tube 39 is slidably positioned within a lumen in guide housing 30. Winged housing 22 has radially extending wings 22a, 22b to be gripped by the user during use, e.g. to aid in retraction of the delivery instrument 10 after the hole closure device 101 is deployed in the vessel. Distal end 23a of winged housing 22 is dimensioned to receive cap 20 thereover, preferably connected by an interference fit, and proximal end 23b is dimensioned to be received within opening 35 of connector portion 34 of guide housing 30, also preferably providing an interference fit. Winged housing 22 can also be connected to connector portion 34 of housing 30 by groove/projection snap fit, a threaded engagement or any other method of attachment. Similarly, cap 20 and winged housing 22 can also be connected by groove/projection snap fit, a threaded engagement or any other method of attachment. Cap 20 has a pair of tabs 21, preferably formed by cutouts 20 in the housing, to engage a sheath 200 as shown in FIG. 8A to connect the sheath to the winged housing 22. Opening 20a in cap 20 allows for a side tube of the sheath 200, the side tube enabling fluid injection through the sheath 200.

Seal 28 is supported within an opening 35 of connector portion 34 of housing 30 to prevent ingress of fluids. Seal 28 has an opening 29 dimensioned and configured to receive advancer tube 39 therethrough.

Advancer tube 39 forms a cheater tube slidable within winged housing 22 and guide housing 30. Advancer tube 39 is in the form of a tube cut at the distal end to form a hinge 39b (FIG. 2). The cut portion forms a casing 26. Casing 26 is somewhat cylindrical shaped with a beveled end 26a formed by the cut in the tube. Casing 26 forms a support housing for the covering member 104 of hole closure device 101. The casing 26 is initially mounted within the lumen of winged housing 22 in a position substantially transverse to a longitudinal axis of the winged housing 22 as shown in FIG. 3. Distal movement of the advancer tube 39 pivots the casing 26 (FIG. 8A) about hinge 39b at it contacts curved wall 22c within winged housing 22 to a more linear position substantially aligned with the longitudinal axis of the winged housing 22 as shown in FIG. 10. This allows for pivoting movement of the elongated covering member 104 from a transverse position to reposition it to a more aligned position for advancement through the sheath 200. The deployment of the closure device 101 is described in more detail below. Casing 28 is pivoted and moved within the tubular channel 24 of winged housing 22, exiting opening 249. Note also that in the substantially aligned position of casing 26 of FIG. 10, the beveled distal end 39a of advancer tube 39 abuts the beveled end 26a of casing 26.

Guide housing 30 of advancer portion 16 has a pair of slots 30a formed in the outer wall and on opposing sides thereof. Slots 30a extend longitudinally along the housing 30 and are each configured and dimensioned to receive a sliding finger tab 37. More specifically and with reference to FIGS. 2 and 2B, each sliding tab 37 has a post 37a extending radially inwardly toward the longitudinal axis of the housing 30. Each post 37a extends through an opening 36a (preferably hexagonal although are shapes are contemplated) in proximal end cap 36 of advancer tube 39. In this manner, movement of the sliding tabs 37 within slots 30a causes sliding movement of the advancer tube 39 through guide housing 30. This is shown in FIGS. 7-10, wherein in FIGS. 7 and 8A, sliding tabs 37 have been moved slightly distally from their initial position of FIG. 1 causing slight distal movement of the advancer tube 39 from its initial position. As can be appreciated, in this position, casing 26 has begun to be pivoted about hinge 39b at the distal end of advancer tube 39. In FIGS. 9 and 10, sliding tabs 37 have been moved further distally to their distal position, causing further distal movement of advancer tube 39 to its distal position. This causes full rotation of casing 26 to its aligned position and movement of casing 26 into a proximal region of sheath 200.

Cap 36 of advancer tube 39 has a pair of openings 36b on opposing sides to receive tabs 82 of cap housing 80 (FIG. 2A) of handle portion 12 discussed below.

In the initial proximal position of sliding tabs 37, a stop 31 limits their distal movement. Stop 31 in is the form of a finger formed by a cutout in housing 30, and can be provided for each tab 37, or alternatively a single stop can be provided to engage one of the sliding tabs 37. The finger 31 projects into slot 30a providing a bump 31a to block movement of tab 37 as flat 37b (FIG. 2B) on the distal side of block 37d supporting post 37 abuts finger 31. That is, as flat 37b contacts finger (stop) 31, finger 31 prevents inadvertent movement of the sliding tabs 37, such as during shipping. In order to distally advance the tabs 37, sufficient force must be applied to override the stop 31, e.g. flex the finger 31 out of the path of the block 37d so block 37d of tab 37 can continue along slot 30a.

Lockout 32 is positioned distal of stop 31 and locks sliding tabs 37 in their distal position. A lockout 32 can be provided on each side of the housing 30 (at the distal end of each slot 30a) or alternatively only one lockout can be provided to lock one of the sliding tabs 37 which would effectively lock both tabs 37. More specifically, the lockout is in the form of two fingers 32 formed by cutouts in housing 30 which project into slot 30a, thereby narrowing the slot 30a at region 30b (FIG. 3). Upon distal movement of tabs 37, flat 37b forces fingers 32 out of the path to move past the fingers 32 as shown in FIGS. 8B and 8C. Flat 37c on the opposing side of flat 37b then engages edge 32a of fingers 32 to prevent retraction of tab 37, thereby locking tabs 37 and thus advancer tube 39 in the forward (distal) position.

Referring back to FIG. 2, an inner tube 15 is concentrically mounted within lumen 14c of outer tube 14. Outer tube 14 has a proximal end 14a extending from the handle housing 12 and connected within opening 84 to cap 80 (FIG. 2A) of housing 12. A distal end 14b of inner tube 14 extends into the guide housing 30 and is configured to abut the retainer of the hole closure device 101 to advance it through the sheath 200. Inner tube 15 has a proximal end 15a and a distal end 15b, with proximal end 15a connected to connector 88 (FIG. 2A). Inner tube 15 has first and second channels 17a, 17b to receive sutures 120, 122.

Turning now to the handle portion 12 which provides the second step in advancement of the hole closure device 101, and with initial reference to FIGS. 2A and 3A, handle portion 12 includes a housing or outer casing 13 containing a central housing 44 and first and second channel housing halves 40, 42, respectively, which are mirror images of each other. Central housing 44 is mounted between housing halves 40 and 42. Each of the housing halves 40, 42, 44 taper to a reduced diameter portion at the distal end.

Channel housing half 40 has a plurality of axially spaced openings 45 to receive radially extending tabs 56 of central housing 44. Similarly, channel housing half 42 has a plurality of axially spaced openings 51 to receive radially extending tabs 55 of central housing 44. This tab/opening engagement connects the housings 40, 42 and 44 together.

First channel housing 40 together with a first side of central housing 44 (e.g. the left side as viewed in FIG. 2A) together from a channel for passage of the suture 120 and engagement member 125 secured to the suture 120 in order to advance the retainer 112 toward the covering member 104 of hole closure device 101. Second channel housing 42 together with a second side of central housing 44 (e.g. the right side as viewed in FIG. 2A) together from a channel for passage of the suture 122 and engagement member 123 secured to the suture 122 in order to advance the retainer 110 toward the covering member 104 of hole closure device 101.

With continued reference to FIG. 2A, housing 40 has a lower channel 40a, an upper channel 40b, and a curved channel 40e joining channels 40a, 40b at their proximal end. At the distal end of upper channel 40b, the upper channel 40b transitions into an angled channel 40c and then into a longitudinally extending channel 40d extending substantially parallel to the longitudinal axis of the housing 40. The angled channel 40c facilitates severing of the suture 120 discussed in more detail below. Identical channel portions are on housing half 42. Thus, housing half 42 has an upper channel, a lower channel, a curved channel joining the upper and lower channels at a proximal end, an angled channel and a longitudinally extending channel.

The central support 44 has a channel on each of its sides to cooperate with the channel in the housing halves 40, 42, thereby together forming the channel (passage) for the respective suture 120, 122 and engagement member 125, 123. This can be best understood in FIG. 2A wherein central housing 44 has a lower channel 58a, an upper channel 58b and a curved channel 58c at the proximal end joining lower channel 58a and upper channel 58b. Central support 44 has the identical channel configuration on the opposing side, except as noted below. Thus, on the opposing side, the upper, lower and curved channels of central housing 44 cooperate with the channels 40a, 40b and 40e of first housing 42. On the side shown in FIG. 2A, the channels 58a, 58b and 58c of housing 44 cooperate with the upper, lower and curved channels of housing 42.

The only difference in the channels on opposing sides of central housing 44 is the recess to receive the respective grommet 48, 49. More specifically, central housing 44 has a distal recess or groove 57 cooperating with a recess on housing 42 for mounting of distal grommet 49. A proximal recess or groove is formed on the opposing side of central housing 44, cooperating with the proximal recess 47 of housing 40 to provide a recess or groove to receive proximal grommet 48.

Distal grommet 49 is illustratively semi-circular in cross-section and has a flat surface for positioning within recess 57 of central housing 44. Other geometries are also contemplated to key the grommets such as the asymmetric configuration shown in FIG. 30B for example. Grommet 49 forms an abutment member or blocking member for engagement member 123 attached to the end of suture 122. Grommet 49 has a lower opening 49a aligned with lower channel 58a (and corresponding lower channel on housing half 42) and an upper opening 49b aligned with upper channel 58b (and corresponding upper channel on housing half 42). Preferably, upper opening 49b is smaller than lower opening 49a to provide an increased frictional force for passage of engagement member 123 therethrough.

Proximal grommet 48 is illustratively semi-circular in cross-section and has a flat surface 48d for positioning within a recess of central housing 44. As with grommet 49, other geometries are also contemplated, such as that shown in FIG. 30B. Grommet 48 forms an abutment or blocking member for engagement member 125 attached to the end of suture 120. Grommet 48 has a lower opening 48a aligned with lower channel 40a (and corresponding lower channel on central housing 44) and an upper opening 48b aligned with upper channel 40b (and corresponding upper channel on central housing 44). Preferably upper opening 48b is smaller than lower opening 48a to provide an increased frictional force for passage of engagement member 125 therethrough.

An elongated knife slot 41 is formed in housing 40 and an identical knife slot is formed in housing 42. These knife slots extend substantially parallel to a longitudinal axis of the housings 40, 42. The knife slots are aligned with knife slot 52 in central housing 44 to receive knife 54. Knife 54 has a substantially planar surface 54a and a proximally directed sharp edge 54b to sever sutures 120, 122 as described in detail below.

At the distal end of casing 13 is a cap 80 having a central opening 84 to receive outer tube 14 and concentric inner tube 15. A pair of finger tabs 82 extending distally from a distal surface 80a snap into openings 36b of cap 36 of advancer tube 39 (FIG. 2) when the handle housing 12 is advanced to its distalmost position (see e.g. FIG. 13). Connector 88 has an opening 87a in tubular portion 87 to receive outer tube 14 and concentric inner tube 15. A spring 70 can also be provided to act as a spacer.

After the advancer tube 39 is advanced by tabs 37 in the manner described above, the handle housing 12 is advanced distally, preferably in increments, causing outer tube 15 to contact the proximally positioned retainer 112 of hole closure device 101 and advance it through the sheath 200 and out the distal end thereof. This is shown in FIG. 11, wherein the sheath has been removed for clarity. The handle housing 12 is advanced until tabs 82 of cap 80 lockingly engage advancer tube cap 36 as the tabs 82 extend through openings 36b and snap fit therein as shown in FIG. 13. After such full advancement of housing 12, the covering member 104 and retainers 110, 112 are positioned in the vessel, with the retainer 104 moving to a transverse position due to the pre-set of the sutures 120, 122. That is, the sutures 120, 122 are preset at an angle of about 90 degrees such that when the covering member 104 is free of the confines of the sheath 200, it automatically pivots to the transverse position of FIGS. 11 and 12.

Once the handle portion 12 is advanced and locked to the advancer portion 16, the delivery instrument 10 is then retracted in the direction of the arrow of FIG. 14. Retraction of the handle housing 12 moves the sutures 120, 122 and engagement members 125, 123 through the channels in the housings 40, 42, 44 as described in detail below. Thus, as can be appreciated, in use, in this multiple step process, first the advancer tube 39 is advanced to rotate the casing 26 to the position shown in FIG. 10 and to move it into the proximal region of the sheath 200. Next, the handle portion 12 is advanced relative to the fixed (locked) advancer portion 16 to advance the hole closure device 101 through the sheath 200 and out the distal end thereof. Once the handle portion 12 has completed its distal travel and interlocked with advancer portion 16, the handle portion 12 (and the entire delivery instrument 10) is retracted thereby securing the patch 104 by movement of the retainers 110, 112 in sequence towards the covering member 104.

The engagement members 123, 125 move within the channels and interact with the grommets 48, 49. The grommets 48, 49 have openings providing engaging portions or abutment or blocking members which provide resistance to movement of the sutures 120, 122. This resistance is achieved by the provision of engagement members 123, 125 on the ends of suture 120 and suture 122. More specifically, an engagement member 125, illustratively substantially spherical in configuration, although other shapes are contemplated, is positioned at the end 120a of suture 120. Similarly, an engagement member 123, illustratively substantially spherical, although other shapes are contemplated, is positioned at the end 122a of suture 122. Engagement members 125, 123 can be attached by methods such as crimping, tying a knot, overmolding, etc. and are configured to engage respective grommets 48, 49 to provide resistance to suture movement.

The use of the delivery device 10 to deliver hole closure device 101 will now be described. Note delivery instrument is connected to a delivery sheath 200. The delivery sheath 200 is inserted through the skin, the tissue puncture tract extending to the vessel wall, and through the vessel wall into the vessel lumen. In the initial position, the retainers 110 and 112 are positioned within advancer tube 39 within winged housing 22 as shown in FIG. 3. Covering member 104 is maintained in a transverse position within casing 26. In this initial position, engagement members 125 and 123 of sutures 120, 122, respectively, are out of engagement with the respective grommets 48, 49 of the handle housing 12.

To deploy the closure device 100, the advancer tube 39 is advanced distally by finger tabs 37 to pivot casing 36 from the initial position of FIG. 3, through the position of FIG. 8A, to the position of FIG. 10 (due to curved wall 22c), thereby aligning the covering member 104 longitudinally for passage through the winged housing 22 and sheath 200, and moving the casing 36 into the proximal region of the sheath 200. Note the tabs 37 of advancer portion 16 are locked in their distal position by locking fingers 32 of guide housing 30.

Next, handle housing 12 is moved distally relative to the fixed advancer portion 16 such that outer tube 15 advances through fixed advancer tube 39 to contact retainer 112 to advance the hole closure device 101 through the sheath 200 and out the distal end of the sheath as shown in FIG. 13 (see also FIGS. 11 and 12). Note that handle housing 12 in its distal position interlocks with the advancer portion 16 due to the engagement of tabs 82 of cap 80 with openings 36b in advancer tube end cap 36. Once the covering member 104 is exposed, it pivots within the vessel lumen from a first delivery position more aligned with the longitudinal axis of the delivery sheath to a transverse placement position as shown in FIGS. 11-13.

The delivery instrument 10 is then retracted proximally in the direction of the arrow of FIG. 14 to place the covering member 104 against the internal side of the opening in the vessel wall to patch or cover the vessel wall opening. FIGS. 11 and 12 show the initial position of the retainers 110, 112 when the closure device 101 is initially inserted into the vessel lumen.

When the delivery instrument 10 is retracted further such that the covering member 104 abuts the internal vessel wall, further retraction of the delivery instrument 10 will deploy the retainers 110, 112 as follows. In the initial position of FIG. 3, engagement member 125 is within lower channel 40a of housing 40 (FIG. 2A) and engagement member 123 is in lower channel 58a of central housing 44 slightly distal of lower opening 49a of proximal grommet 49 (FIG. 3A). It should be appreciated that as discussed herein, the channels of housing 42 cooperate with the channels on one side of central housing 44 and the channels of housing 40 cooperate with the channels on the opposing side of central housing 44. Thus, for brevity, only one of the cooperating channels is mentioned, it being understood that the channels are formed by cooperation of these components.

Upon further proximal retraction of the handle housing 12, suture 122 is pulled proximally such that engagement member 123 of suture 122 is pulled against an engaging portion of grommet 49, i.e., opening 49a in grommet 49, as shown in FIGS. 15 and 16. (Note the force of covering member 104 against the vessel wall provides a counter force such that proximal movement of the delivery instrument 10 and sutures 120, 122 cause distal movement of the retainers 110, 112 attached to the sutures 122, 120). The pulling (tensioning) of the suture 122 causes retainer 110, attached to the opposing end of suture 122, to move toward the covering member 104 as shown in FIG. 16. Note that the engagement member 125 of suture 120 is not yet engaged with proximal grommet 48. In this position, distal grommet 49 provides a stop to restrict movement of the suture 122. This engagement also provides a tactile feel to the user to indicate that retainer 110 has moved a substantial distance toward covering member 104.

When delivery instrument 10 is pulled further proximally with respect to the delivery sheath 200 it pulls (tensions) suture 120 proximally to move retainer 112 toward covering member 104 as shown in FIG. 18. Such movement continues until engagement member 125 abuts/engages an engaging portion of proximal grommet 48, i.e., at lower opening 48a of proximal grommet 48, as shown in FIGS. 17 and 18. Grommet 48 thereby provides a stop to limit movement of the suture 120. Grommet 48 also provides a tactile feel to the user to indicate that retainer 112 has moved a substantial distance toward covering member 104. Note that engagement member 123 has already overcome distal grommet 49, and passed through its lower opening 49a, and is no longer in tension. As can be appreciated, retainers 110 and 112 have now been moved adjacent the covering member 104 but not yet in their fully distal securement position. Note this delivery method distributes the force, e.g. reduces the load on the patch.

Continued proximal movement of delivery instrument 10 applies sufficient tension on suture 120 so engagement member 125 passes through lower opening 48a of grommet 48 and continues its travel around curved channel 40e until it engages grommet 48 at upper opening 48b. This position is shown in FIGS. 19 and 20. This moves retainer 112 further distally toward covering member 104 to tighten retainer 112 with respect to covering member 104. Note engagement member 123 continues its movement along upper channel 58b (after passing around proximal curved channel 58c) toward upper opening 49b of distal grommet 49.

Continued proximal movement as shown in FIGS. 21 and 22 pulls suture 122 proximally, moving engagement member 123 into engagement with upper opening 49b. Engagement member 125 has overcome engagement with proximal grommet 48. Further movement of suture 122 moves retainer 110 further distally toward covering member 14, thereby tightening retainer 110 with respect to covering member 104, securing the covering member 104 in position. Note the extent of movement of the retainers 110, 112 toward the covering member 104, i.e. the final distance between the retainers 110 and 112 and covering member 104, will depend on the thickness of the patient's tissue.

With placement of the retainers 110 and 112 within the tissue tract leading to the vessel opening (but outside the vessel opening), the sutures 122, 120 are now severed automatically by the cutting blade 54 of delivery instrument 10. This is illustrated in FIGS. 23-26.

As the delivery instrument 10 is pulled further proximally, engagement members 125, 123 and sutures 120, 122 enter angled channel 40c on channel housing half 40 and an identical angled channel on the opposing channel housing half 42. As delivery instrument 10 is retracted further and sutures 120 and 122 are retracted further, engagement members 123, 125 move within longitudinal channel 40d on housing 40 (FIGS. 23 and 24) and an identical longitudinal channel on housing 42, with the sutures 120, 122 remaining above these longitudinal channels to contact cutting edge 54a of knife 54 (FIGS. 25 and 26) to sever the sutures 120, 122 as shown in FIG. 26. Note engagement members 123, 125 can float inside the channel because they are no longer in tension. The sutures 120, 122 can be further tightened and then trimmed by the surgeon to be flush with the patient's skin.

An alternate embodiment of the hole closure delivery instrument is illustrated in FIGS. 27-41. In this embodiment, the handle portion performs the multiple steps of advancing the advancer (cheater) tube to rotate the hinged casing at the end of advancer tube containing the covering member 104 of the hole closure device 101 as well as advances the hole closure device 101 through the sheath for delivery to the vessel. After delivery, the instrument is retracted and the retainers 110, 112 are advanced toward the covering member 104 in the same way as in the embodiment of FIGS. 1-26.

Turning first to FIGS. 27 and 30A, delivery instrument is designated generally by reference numeral 212 and has a winged housing 214, a plunger guide housing 216 formed by housing halves 240a, 240b and a handle portion or pusher (plunger) 260. Plunger 260 is slidably received within guide housing 216.

Winged housing 214 is connected to end cap 217, preferably by an interference or snap fit as distal end 219 is dimensioned to receive end cap 217 thereover. End cap 217 has locking tabs 218a, 218b (FIG. 29) on opposing sides to engage sheath 200 in the same manner as locking tabs 21 of end cap 20 of the embodiment of FIG. 1.

Winged housing 214 has a pair of wings 214a, 214b extending radially therefrom for grasping by the user to facilitate movement of the plunger 260 and to aid in retraction of the delivery instrument 212 after the hole closure device 101 is delivered to the vessel lumen. Cap 217 has an opening 217a through which side arm 201 of sheath 200 can extend as in opening 20a of end cap 20. Side arm 201 provides for delivery of fluids through the sheath 200.

Supported within a distal end of guide housing 216 is an advancer 220. Advancer is in the form of a tube 220 which forms a cheater tube slidable within guide housing 216 and winged housing 214. Advancer tube 220, like advancer tube 39 of the embodiment of FIG. 1, is in the form of a tube cut at the distal end to form a hinge 228b. The cut portion forms a casing 228. Casing 228 is somewhat cylindrical shaped with a beveled end 228a formed by the cut in the tube as shown in FIG. 31A. Casing 228 forms a support housing for the covering member 104 of hole closure device 101. The casing 228 is initially mounted within the winged housing 214 in a position substantially transverse to a longitudinal axis of the winged housing 214 as shown in FIG. 31A. Distal movement of the advancer tube 220 pivots the casing 228 (in the same manner as casing 28 of FIG. 8A) about hinge 228b as it contacts curved surface 214c within winged housing 214 to a more linear position substantially aligned with the longitudinal axis of the winged housing 214 in the same manner as casing 28 shown in FIG. 10. That is, casing 228 is pivoted from the initial transverse position of FIGS. 31A and 33 to the aligned position of FIGS. 34A and 35). This allows for pivoting movement of the elongated covering member 104 to reposition it to a more aligned position for advancement through the sheath 200. Note also that in the alignment position of casing 228, the beveled distal end 221 of advancer tube 220 abuts the beveled end 228a of casing 228 (as in casing 28 of FIG. 10).

With reference to FIG. 30A, advancer tube 220 has offset wings 220a, 220b. One of the wings, e.g. wing 220a, can have indicia to indicate alignment of the casing 228. A clip 275 (see also FIG. 29) provides a stop to prevent inadvertent movement of the advancer tube 220, e.g. during shipping. That is, distal edges 223a, 223b of wings 220a, 220b abut the legs 275a, 275b, respectively, of clip 275, thus preventing distal movement of advancer tube 220 unless the clip 275 is removed. Thus, clip 275 also provides a shipping lock. The upper edge 225a (as viewed in the orientation of FIG. 34A) of edge 223a and a lower edge 225b of edge 223b abut internal wall 248a and 248b, respectively, of guide housing 216, to prevent further distal movement of advancer 220 as described in more detail below. That is, when advancer 220 is moved distally to the position of FIG. 34A, walls 248a, 248b block further distal movement. Note the internal walls 248a, and 248b are formed by the two housing halves 240a, 240b.

A seal 258, with an opening 258a for receiving outer tube 280, prevents the ingress of fluids. The seal 258 is mounted in the distal portion of guide housing 216 within an opening in cap 257 which is fixed to housing 216 by a pair of transverse pins 256 extending into a pair of side openings 257a of cap 257.

First and second rails 250, 252, extend between plunger 260 and wings 220a, 220b. More specifically, upper rail 250 (as viewed in the orientation of FIGS. 30A and 31A-31C) extends within guide housing 216 between the plunger 260 and wing 220a of advancer tube 220. A lower rail 252 (as viewed in the orientation of FIGS. 30A and 31-31C), positioned within guide housing 216 on a different plane than rail 250, extends between plunger 260 and wing 220b of advancer tube 220. As shown in FIG. 33, rail 250 has a distal finger 250a, an intermediate finger 250b, and a proximal finger 250c extending upwardly to engage internal walls of the guide housing 216 discussed in detail below. Similarly, rail 252 has a distal finger 252a, an intermediate finger 252b, and a proximal finger 252c extending downwardly to engage internal walls of the guide housing 216 also discussed in detail below.

The distal edges 250d, 252d of distal fingers 250a, 252a abut inwardly extending walls 243a, 243d of guide housing 216 (FIG. 31A), and the proximal edges 250e, 252e, of proximal fingers 250c, 252c, abut inwardly extending walls 243c, 243f of guide housing 216 (FIG. 31B) in the initial position.

The distal end of finger 250a of rail 250 is received in slot 220d of winged housing 220a; the distal end of finger 252b of rail 252 is similarly received in a slot in winged housing 220b (see FIGS. 33 and 37). The proximal finger 250c of rail 250 is received in slot 267a in plunger housing 260; proximal finger 252c of rail 252 is similarly received in a slot on the opposing side of plunger housing 260. Rails 250, 252 function to initially advance advancer tube 220 when plunger 260 is advanced, and then are moved out of operative engagement with wings 220a, 220b so the plunger 260 advances while the advancer tube 220 remains stationary as the outer tube 280 is advanced within advancer tube 220.

With reference to FIG. 30B, plunger 260 includes housing halves 261a, 261b. Contained within the housing halves 261a, 261b are first channel housing 264, second channel housing 266 and central housing 268. These channel housings are identical to housings 40, 42, and 44 of FIGS. 1-26 to provide movement of the sutures 120, 122 of the hole closure device 101 and their respective engagement members to advance the retainers 110, 112 of the hole closure device 101 and therefore for brevity are not further described herein or further labeled in the drawings. Knife 274 is supported in the slots in the channel housings 264, 266 and 268. Knife 274 is identical in structure and function to knife 54 of FIG. 2A. A shroud 276 is positioned above the knife 274 (as viewed in the orientation of FIG. 30B) to prevent inadvertent contact of the sutures 120, 122 with the knife 274 which can cause premature severing of the sutures 120, 122 of the hole closure device 101. (A shroud can also be provided above knife 54 in the embodiment of FIG. 1). Grommets 270, 272, having engaging portions to form blocking or abutment members for the engagement members 125, 123 on the end of the sutures 120, 122 of the hole closure device 101, are identical to grommets 49, 48, respectively, of FIG. 2A and therefore for brevity are not discussed in detail below since the description of the function of grommets 48, 49, and the passage of engagement members 125, 123 are fully applicable to this embodiment of FIG. 30B. Consequently, when device 212 is retracted after delivery of the hole closure device 101 to the vessel, the sutures and engagement members pass through the channels in housing 264, 266 and 268 in the same manner as in the embodiment of FIGS. 1-26 to advance the retainers toward the covering member to secure the hole closure device and to sever the sutures.

With reference to FIG. 30A, end cap 281 of inner tube 282 is secured within opening 260a of plunger 260 by a snap or friction fit. Inner tube 282 is received in the lumen of outer tube 280. A reinforcing tube 284, preferably composed of stiffer material, is concentrically interposed between the inner tube 282 and outer tube 280. Outer tube 280 is attached to the end cap 281 of plunger 260 so that distal movement of plunger 260 advances the outer tube 280 through the lumen in advancer tube 220 to contact spherical retainer 110 of the closure device 101 to advance the closure device 101 through the sheath 200 and into the vessel. The inner tube 282 has a pair of lumens to receive respective sutures 120, 122.

Proximal and distal sleeves 247b, 247a surround the housing halves 240a, 240b of the guide housing 216 to secure them together.

In use, in the initial position of FIGS. 31a-31c (and FIG. 33), plunger 260 is in its proximalmost position and advancer tube 220 is in the proximalmost position as edges 223a, 223b of wings 220a, 220b, respectively, abut clip 275. Thus, in this initial position, with the locking clip 275 in place, distal movement of the plunger 260 is blocked. Note in this position, casing 228 (and hole covering member 104 contained therein) are in the transverse position. Rails 250, 252 which extend between plunger 260 and wings 220a, 220b, are positioned such that edge 250e of proximal finger 250c of rail 250 is in contact with the edge of proximal radially inwardly extending internal wall 243c of housing 216 and edge 252e of proximal finger 252c of rail 252 is in contact with the edge of proximal radially inwardly extending wall 243f of housing 216, best shown in FIG. 31B. Additionally, edge 250d of distal finger 250a is in contact with the edge of distal radially inwardly extending internal wall 243a of housing 216 and edge 252d of distal finger 252a is in contact with the edge of distal radially inwardly extending wall 243d of housing 216. Thus, the fingers 250a, 250b, 250c of rail 250 are spaced from the spaces between walls 243a, 243b and 243c, and the fingers 252a, 252b and 252c of rail 252 are spaced from the spaces between walls 243d, 243e and 243f.

To actuate the delivery instrument 212 to advance the plunger 260 to move the advancer tube 220 distally in the first stage of operation, clip 275 is manually removed from the openings 251a, 251b of guide housing 216 (FIG. 32) and plunger 260 is advanced distally. Such distal advancement advances the advancer tube 220 due to the engagement of rails 250, 252 with wings 220a, 220b of advancer tube 220. Advancement of the advancer tube 220 causes casing 228 to pivot from its transverse position to the longitudinally aligned position of FIGS. 34A and 35 as the casing 228 is forced against internal curved wall 214c. The plunger 260 is advanced so that aligned casing 228 is moved through winged housing 214 and into a proximal region of sheath 200. Note that the longitudinal alignment of casing 228 pivots covering member 104 of hole closure device 101 to a more aligned position for delivery through the sheath 200 to the vessel lumen. Note that roller pins 259 (FIGS. 34B and 35) on opposing sides of plunger 260 ride within longitudinal track 253 of housing 240b and a similar longitudinal track in housing 240a, thereby acting as low friction bearings within the tracks in housing halves 240a, 240b for smoother motion of the plunger 260 within guide housing 216. This advanced position of tube 220 and intermediate position of plunger 260 are shown in FIGS. 34A-34C and 35.

Figure 36B:
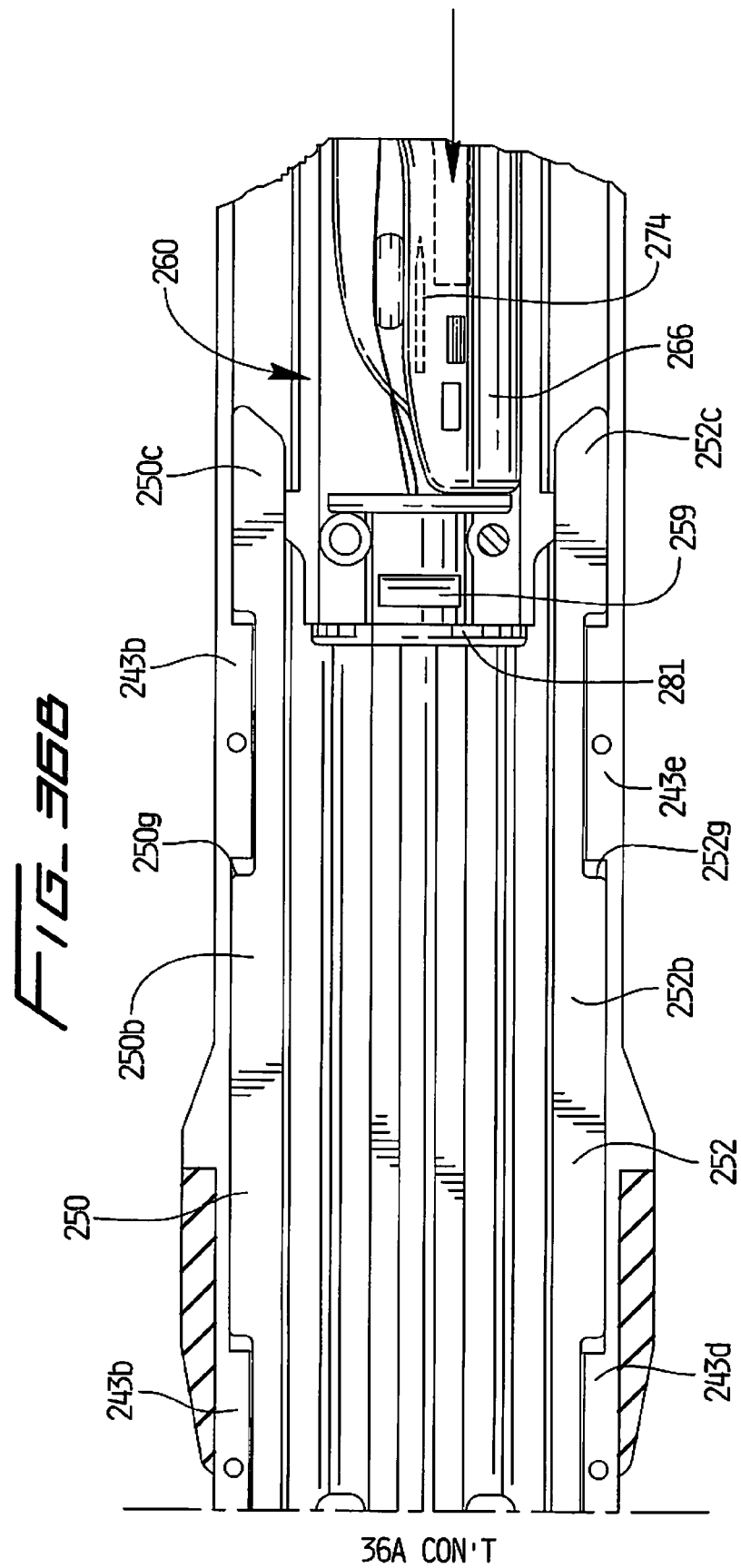

Note that plunger 260 advances advancer tube 220 until the distal edges 225a, 225b of wings 220a, 220b abut edges 248a, 248b of housing 216 as shown in FIG. 34A. In this position, plunger 260 has advanced to an intermediate region of guide housing 216. As the advancer tube 220 is thus blocked against further distal movement by edges 248a, 248b, further distal movement of plunger 260 does not advance advancer tube 220. Instead, as plunger 260 is advanced, distal edges 250d and 252d of rails 250, 252, respectively, and 250g of rail 250 have moved past the distal edges of respective distal radially extending walls 243a and 243d and proximal edges 250e, 252e of rails 250, 252 respectively, have moved past the distal edges of the respectively radially extending proximal walls 243c, 243f. However, proximal edge 250f of distal finger 250a and proximal edge 252f of distal finger 252 remain engaged with walls 243a, 243d. Further, proximal edges 250g, 252g of intermediate fingers 250b, 252b, respectively, are engaged with distal edges of walls 243b, 243e (FIG. 34B). Upon further distal movement of plunger 260, proximal, intermediate and distal fingers 250a, 250b and 250c of rail 250 extend into the respective spaces between walls 243a, 243b and 243c and the proximal, intermediate, and distal fingers 252a, 252b and 252c of rail 252 extend into the respective spaces between the walls 243d, 243e and 243f as shown in FIGS. 36A, 36B and 37 as edges 250f, 252f and 250g, 252g clear the respective walls. When this occurs, rail 250 comes out of the slot 220d in wings 220a and rail 252 comes out of the slot in wing 220b so the rails 250, 252 are disengaged from wings 220a, 220b and thus the advancer 220 is no longer in operative engagement with plunger 260. Note rails 250, 252 ride within ramps in the wings 220, 220b. That is, in this position of rails 250, 252, advancement of plunger 260 no longer advances advancer 220 and instead, advancement of plunger 260 moves the outer tube 280 with respect to the advancer 220 which is now stationary.

Upon further distal advancement of plunger 260 to its distalmost position as shown in FIGS. 39A-39C and 38, outer tube 280 moves within stationary advancer tube 220 as the wings 220a, 220b are blocked by walls 248a, 248b from further advancement, and the rails 250, 252 are no longer in operative engagement with the wings 220a, 220b. As outer tube 280 is advanced through winged housing 214 and into the sheath 200, it continues to advance the hole closure device 101 through the sheath 200 and into the vessel as it engages retainer 110. That is, full distal advancement of plunger 260 advances the hole closure device 101 from the distal end of the sheath 200. This position is shown in FIG. 35. In this distalmost position, pins 259 are locked by locking tabs 241a, 241b to prevent proximal movement thereof. That is, when plunger 260 has completed its stroke, pins 259 have bypassed locking tabs 241a, 241b and are now blocked from proximal movement by these tabs 241a, 241b.

Once the plunger 260 is fully advanced and locked in its distal position, i.e., blocked from proximal movement, the delivery instrument 212 is retracted in the same manner as delivery instrument 100 of FIGS. 1-26 to advance the retainers 110, 112 toward covering member 104 and to automatically sever the sutures 120, 122 by knife 274 as the sutures 120, 122 and engagements members slide within the channels in the housings of FIG. 30B.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical delivery instrument for delivering a vascular hole closure device having a hole covering member, the delivery instrument comprising a housing, a plunger and an advancer movable within the housing, the advancer having a first portion and a distal portion hingedly connected to the first portion and forming a casing for supporting the hole covering member, wherein distal movement of the advancer pivots the casing from an angled position to a more linear position to change the orientation of the covering member from an angled position to a more aligned position, the plunger advanceable to advance the covering member into the vessel, the hole closure device includes first and second flexible members, the first flexible member having a first engagement member and the second flexible member having a second engagement member, wherein the plunger has first and second longitudinally extending openings and first and second engaging portions, the first engaging portion limiting movement of the first engagement member and the second engaging portion limiting movement of the second engagement member, wherein the first engagement member is held by the first engaging portion until a predetermined force is applied to the first engagement member during placement of the hole closure device at a target site and the second engagement member is held by the second engaging portion until a predetermined force is applied to the second engagement member during placement of the hole closure device at the target site.

2. The surgical delivery instrument of claim 1, wherein the first engaging portion comprises a first opening in a first grommet aligned with the first longitudinally extending opening and the second engaging portion comprises a second opening in a second grommet aligned with the second longitudinally extending opening.

3. The surgical delivery instrument of claim 1, wherein the housing includes an angled inner surface engagable by the casing to pivot the casing to the more linear position.

4. The surgical delivery instrument of claim 1, wherein the plunger includes a tube and a handle portion positioned proximally of the tube, and movement of the handle portion distally advances the tube within a lumen of the advancer.

5. The surgical delivery instrument of claim 1, further comprising a distal stop to limit distal movement of the advancer.

6. The surgical delivery instrument of claim 1, further comprising a first actuator for moving the advancer distally, the first actuator movable independently of the plunger.

7. The surgical delivery instrument of claim 1, wherein initial advancement of the plunger moves the advancer distally and subsequent advancement of the plunger advances the covering member into the vessel.

8. The surgical delivery instrument of claim 1, further comprising first and second rails operatively connecting the advancer and the plunger.

9. The surgical delivery instrument of claim 8, wherein the first and second rails are operatively dissociated from the plunger when the advancer is moved to a distal position into contact with the stop.

10. A surgical delivery instrument for delivering into a vessel a vascular hole closure device having a hole covering member, the delivery instrument comprising a housing, an advancer movable within the housing, and a plunger, the advancer movable to change the position of the covering member within the housing and the plunger subsequently movable to advance the covering member from the housing into the vessel, and first and second rails operatively connecting the advancer and the plunger.

11. The surgical delivery instrument of claim 10, wherein the hole closure device includes first and second flexible members, the first flexible member having a first engagement member and the second flexible member having a second engagement member, wherein the plunger has first and second longitudinally extending openings and first and second engaging portions, the first engaging portion limiting movement of the first engagement member and the second engaging portion limiting movement of the second engagement member, wherein the first engagement member is held by the first engaging portion until a predetermined force is applied to the first engagement member during placement of the hole closure device at a target site and the second engagement member is held by the second engaging portion until a predetermined force is applied to the second engagement member during placement of the hole closure device at the target site.

12. The surgical delivery instrument of claim 10, wherein movement of the plunger moves the advancer to change the position of the covering member.

13. The surgical delivery instrument of claim 10, further comprising a first actuator for moving the advancer, the first actuator movable independently of the plunger.

14. The surgical delivery instrument of claim 10, further comprising a stop to limit movement of the advancer, wherein the plunger is movable within the advancer when the advancer comes into contact with the stop.

15. A surgical delivery instrument for delivering a vascular hole closure device having a first flexible member having a first engagement member extending therefrom and a second flexible member having a second engagement member extending therefrom, the delivery instrument comprising a housing having first and second longitudinally extending lumens and first and second members, the first member having a first opening aligned with the first lumen, the second member having a second opening aligned with the second lumen, the first engagement member passing through the first opening when a predetermined proximal force is applied and the second engagement member passing through the second opening when a predetermined proximal force is applied, wherein the first engagement member is held by the first member until the predetermined proximal force is applied to the first engagement member during placement of the closure device at a target site.

16. The surgical delivery instrument of claim 15, wherein the second engagement member is held by the second member until the predetermined proximal force is applied to the second engagement member during placement of the closure device at the target site.

17. The surgical delivery instrument of claim 16, wherein the first flexible member is a suture and the second flexible member is a suture, and the delivery instrument further comprises a cutting member positioned within the housing for automatically severing the sutures.

18. The surgical delivery instrument of claim 15, wherein the first member has a third opening and the second member has a fourth opening, wherein the first engagement member is passable through the first opening when a first force is applied and subsequently passable through the third opening when a subsequent force is applied.

19. The surgical delivery instrument of claim 18, wherein the second engagement member is passable through the second opening when a second force is applied and subsequently passable through the fourth opening when a subsequent force is applied.

20. The surgical delivery instrument of claim 15, wherein the vascular hole closure device has a covering member at a distal end for positioning internal of a vessel and a first and a second retainer for positioning external of the vessel, the first flexible member extending between the covering member and the first retainer and the first engagement member positioned at a proximal portion of the first flexible member, and the second flexible member extending between the covering member and the second retainer and the second engagement member positioned at a proximal portion of the second flexible member, wherein proximal movement of the delivery instrument advances the first retainer and the second retainer toward the covering member.

* * * * *